US007517520B2

(12) United States Patent
Manolova et al.

(10) Patent No.: US 7,517,520 B2
(45) Date of Patent: *Apr. 14, 2009

(54) PACKAGING OF IMMUNOSTIMULATORY OLIGONUCLEOTIDES INTO VIRUS-LIKE PARTICLES: METHOD OF PREPARATION AND USE

(75) Inventors: Vania Manolova, Zürich (CH); Martin F. Bachmann, Seuzach (CH); Andreas Cornelius, Regensdorf (CH); Patrik Maurer, Zürich (CH); Edwin Meijerink, Zürich (CH); Karl G. Proba, Zürich (CH); Katrin Schwarz, Schlieren (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 90 days.

This patent is subject to a terminal disclaimer.

(21) Appl. No.: 10/550,518

(22) PCT Filed: Mar. 25, 2004

(86) PCT No.: PCT/EP2004/003165

§ 371 (c)(1),
(2), (4) Date: Sep. 23, 2005

(87) PCT Pub. No.: WO2004/084940

PCT Pub. Date: Oct. 7, 2004

(65) Prior Publication Data

US 2006/0251677 A1  Nov. 9, 2006

Related U.S. Application Data

(60) Provisional application No. 60/457,348, filed on Mar. 26, 2003, now abandoned.

(51) Int. Cl.
*A01N 63/00* (2006.01)
*C12N 7/00* (2006.01)
*C12N 1/20* (2006.01)

(52) U.S. Cl. .................. 424/93.2; 435/235.1; 435/252.1
(58) Field of Classification Search ...................... None
See application file for complete search history.

(56) References Cited

U.S. PATENT DOCUMENTS

| 4,722,840 | A | 2/1988 | Valenzuela et al. |
| 4,918,166 | A | 4/1990 | Kingsman et al. |
| 4,959,314 | A | 9/1990 | Mark et al. |
| 5,057,540 | A | 10/1991 | Kensil et al. |
| 5,071,651 | A | 12/1991 | Sabara et al. |
| 5,143,726 | A | 9/1992 | Thornton et al. |
| 5,334,394 | A | 8/1994 | Kossovsky et al. |
| 5,374,426 | A | 12/1994 | Sabara et al. |
| 5,565,548 | A | 10/1996 | Neurath et al. |
| 5,698,424 | A | 12/1997 | Mastico et al. |
| 5,780,448 | A | 7/1998 | Davis |
| 5,844,075 | A | 12/1998 | Kawakami et al. |
| 5,871,747 | A | 2/1999 | Gengoux-Sedlik et al. |
| 5,874,560 | A | 2/1999 | Kawakami et al. |
| 5,935,821 | A | 8/1999 | Chatterjee et al. |
| 5,939,598 | A | 8/1999 | Kucherlapati et al. |
| 5,962,636 | A | 10/1999 | Bachmaier et al. |
| 5,989,868 | A | 11/1999 | Harrison et al. |
| 5,994,523 | A | 11/1999 | Kawakami et al. |
| 6,025,470 | A | 2/2000 | Valmori et al. |
| 6,231,864 | B1 | 5/2001 | Birkett |
| 6,270,778 | B1 | 8/2001 | Kawakami et al. |
| 6,277,956 | B1 | 8/2001 | Valmori et al. |
| 6,326,200 | B1 | 12/2001 | Valmori et al. |
| 6,368,857 | B1 | 4/2002 | Valmori et al. |
| 6,380,364 | B1 | 4/2002 | Mueller et al. |
| 6,384,190 | B1 | 5/2002 | Valmori et al. |
| 6,537,560 | B1 | 3/2003 | Kawakami et al. |
| 6,949,520 | B1 * | 9/2005 | Hartmann et al. ............. 514/44 |

(Continued)

FOREIGN PATENT DOCUMENTS

EP  0 038 154 B1  10/1981

(Continued)

OTHER PUBLICATIONS

Storni et al, J Immunol 2004;172:1777-85.*
Adams, S.E., et al., "The expression of hybrid HIV: Ty virus-like particles in yeast," *Nature* 329:68-70, Nature Publishing Group (1987).
Addo, M.M., et al., "Comprehensive Epitope Analysis of Human Immunodeficiency Virus Type 1 (HIV-1)-Specific T-Cell Responses Directed against the Entire Expressed HIV-1 Genome Demonstrate Broadly Directed Responses, but no Correlation to Viral Load," *J. Virol.* 77:2081-2092, American Society for Microbiology (2003).
Allen, T.M., et al., "Induction of AIDS Virus-Specific CTL Activity in Fresh, Unstimulated Peripheral Blood Lymphocytes from *Rhesus macaques* Vaccinated with a DNA Prime/Modified Vaccinia Virus Ankara Boost Regimen," *J. Immunol.* 164:4968-4978, The American Association of Immunologists (2000).

(Continued)

*Primary Examiner*—Q. Janice Li
(74) *Attorney, Agent, or Firm*—Sterne, Kessler, Goldstein & Fox PLLC

(57) ABSTRACT

The invention relates to the finding that virus like particles (VLPs) can be loaded with immunostimulatory substances, in particular with DNA oligonucleotides containing non-methylated C and G (CpGs). Such CpG-VLPs are dramatically more immunogenic than their CpG-free counterparts and induce enhanced B and T cell responses. The immune response against antigens optionally coupled, fused or attached otherwise to the VLPs is similarly enhanced as the immune response against the VLP itself. In addition, the T cell responses against both the VLPs and antigens are especially directed to the Th1 type. Antigens attached to CpG-loaded VLPs may therefore be ideal vaccines for prophylactic or therapeutic vaccination against allergies, tumors and other self-molecules and chronic viral diseases.

50 Claims, 6 Drawing Sheets

U.S. PATENT DOCUMENTS

Figure 1:
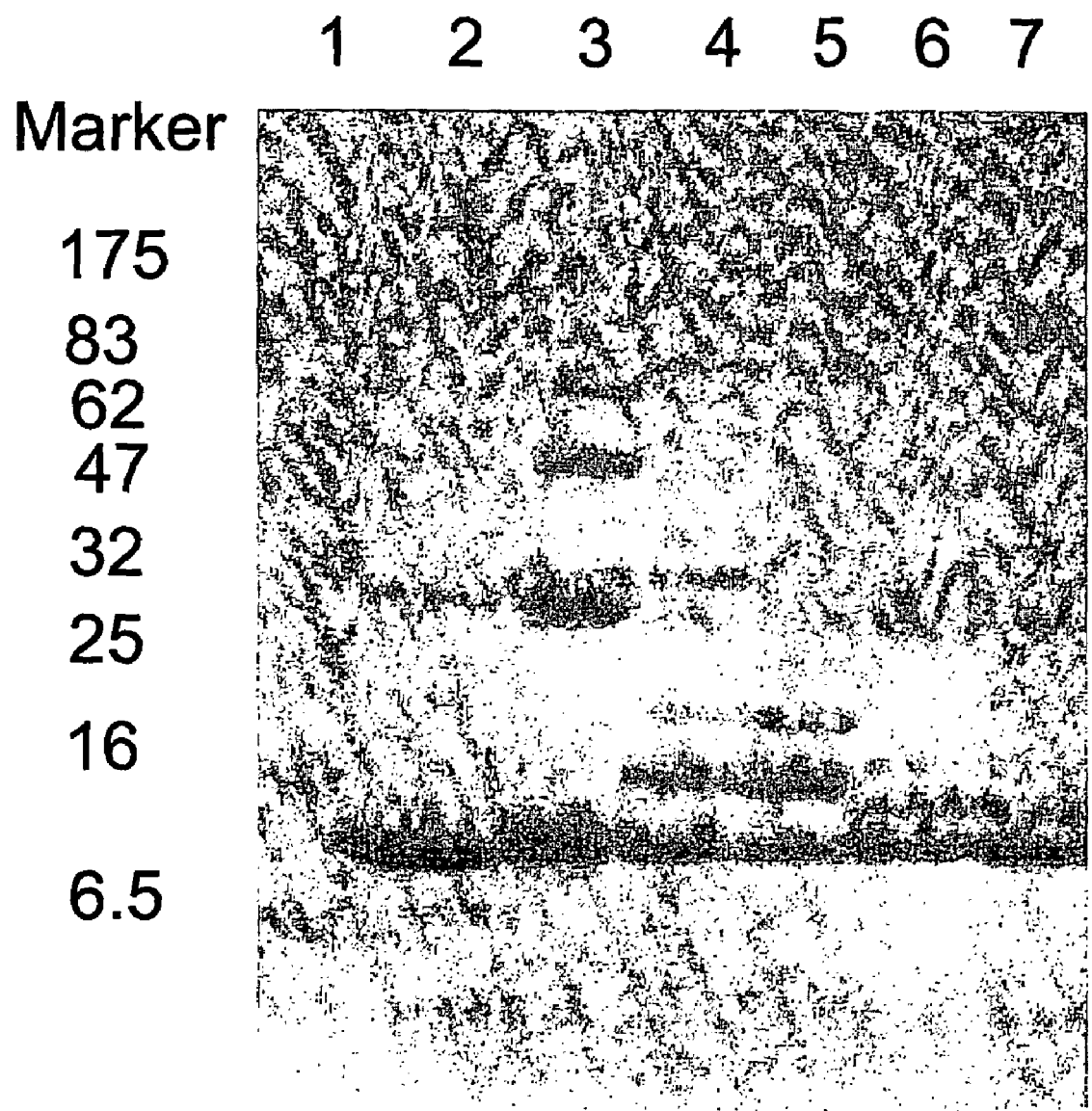

| | | |
|---|---|---|
| 2001/0044416 A1 | 11/2001 | McCluskie et al. |
| 2002/0064533 A1 | 5/2002 | Murray |
| 2002/0081295 A1 | 6/2002 | Schiller et al. |
| 2003/0050263 A1 | 3/2003 | Krieg et al. |
| 2003/0050268 A1 | 3/2003 | Krieg et al. |
| 2003/0060440 A1 | 3/2003 | Klinman et al. |
| 2003/0082804 A1 | 5/2003 | Valmori et al. |
| 2003/0087848 A1 | 5/2003 | Bratzler et al. |
| 2003/0099668 A1 | 5/2003 | Bachmann et al. |
| 2003/0144482 A1 | 7/2003 | Kawakami et al. |
| 2004/0005338 A1 | 1/2004 | Bachmann et al. |
| 2005/0101557 A1 | 5/2005 | Krieg et al. |
| 2005/0169888 A1 | 8/2005 | Hartmann et al. |
| 2006/0286070 A1 | 12/2006 | Hartmann et al. |

FOREIGN PATENT DOCUMENTS

| | | | |
|---|---|---|---|
| EP | 0 201 416 A1 | 11/1986 | |
| EP | 0 421 635 A1 | 4/1990 | |
| EP | 0 385 610 B1 | 9/1990 | |
| EP | 0 468 520 A2 | 1/1992 | |
| EP | 0 578 293 A1 | 1/1994 | |
| EP | 0 677 111 B1 | 10/1995 | |
| EP | 0 772 619 B1 | 5/1997 | |
| EP | 0 855 184 A1 | 7/1998 | |
| WO | WO 92/13081 A1 | 8/1992 | |
| WO | WO 94/02499 A1 | 2/1994 | |
| WO | WO 94/15585 | 7/1994 | |
| WO | WO 95/26204 A1 | 10/1995 | |
| WO | WO 95/29193 A2 | 11/1995 | |
| WO | WO 96/02555 A1 | 2/1996 | |
| WO | WO 96/30523 A2 | 10/1996 | |
| WO | WO 97/28259 A1 | 8/1997 | |
| WO | WO 98/18810 A1 | 5/1998 | |
| WO | WO 98/33517 A1 | 8/1998 | |
| WO | WO 98/40100 A1 | 9/1998 | |
| WO | WO 98/49195 A1 | 11/1998 | |
| WO | WO 98/50071 A1 | 11/1998 | |
| WO | WO 98/52581 A1 | 11/1998 | |
| WO | WO 98/55495 A2 | 12/1998 | |
| WO | WO 98/58751 A1 | 12/1998 | |
| WO | WO 99/11275 A2 | 3/1999 | |
| WO | WO 99/28478 A1 | 6/1999 | |
| WO | WO 99/29723 A1 | 6/1999 | |
| WO | WO 99/40934 A1 | 8/1999 | |
| WO | WO 99/51259 A2 | 10/1999 | |
| WO | WO 99/57289 A2 | 11/1999 | |
| WO | WO 00/00462 A1 | 1/2000 | |
| WO | WO 00/06588 A1 | 2/2000 | |
| WO | WO 00/14217 A2 | 3/2000 | |
| WO | WO 00/23955 A1 | 4/2000 | |
| WO | WO 00/32227 A2 | 6/2000 | |
| WO | WO 00/37610 A2 | 6/2000 | |
| WO | WO 00/39304 A2 | 7/2000 | |
| WO | WO 00/50461 A1 | 8/2000 | |
| WO | WO 00/62800 A2 | 10/2000 | |
| WO | WO 01/16320 A1 | 3/2001 | |
| WO | WO 01/22972 A2 | 4/2001 | |
| WO | WO 01/22990 A2 | 4/2001 | |
| WO | WO 01/56603 A1 | 8/2001 | |
| WO | WO 01/58478 A1 | 8/2001 | |
| WO | WO 01/77158 A1 | 10/2001 | |
| WO | WO 01/85208 A2 | 11/2001 | |
| WO | WO 01/98333 A2 | 12/2001 | |
| WO | WO 02/10416 A1 | 2/2002 | |
| WO | WO 02/14478 A2 | 2/2002 | |
| WO | WO 02/053141 A2 | 7/2002 | |
| WO | WO 02/056905 A2 | 7/2002 | |
| WO | WO 02/056907 A2 | 7/2002 | |
| WO | WO 03/024480 A2 | 3/2003 | |
| WO | WO 03/024481 A2 | 3/2003 | |
| WO | WO 03/030656 A2 | 4/2003 | |
| WO | WO 03/031466 A2 | 4/2003 | |
| WO | WO 03/039225 A2 | 5/2003 | |
| WO | WO 03/040164 A2 | 5/2003 | |
| WO | WO 03/040308 A2 | 5/2003 | |
| WO | WO 03/045431 A2 | 6/2003 | |
| WO | WO 03/059386 A2 | 7/2003 | |
| WO | WO 2004/000351 A1 | 12/2003 | |
| WO | WO 2004/007538 A2 | 1/2004 | |
| WO | WO 2004/009124 A2 | 1/2004 | |
| WO | WO 2004/016282 A1 | 2/2004 | |
| WO | WO 2004/071493 A1 | 8/2004 | |
| WO | WO 2005/004907 A1 | 1/2005 | |
| WO | WO 2005/014110 A1 | 2/2005 | |
| WO | WO 2005/042018 A2 | 5/2005 | |
| WO | WO 2006/032674 A1 | 3/2006 | |

OTHER PUBLICATIONS

Altschul, S.F., et al., "Basic Local Alignment Search Tool," *J. Mol. Biol.* 215:403-410, Academic Press Limited (1990).

Altschul, S.F., et al., "Issues in searching molecular sequence databases," *Nature Genet.* 6:119-129, Nature Publishing Group (1994).

Bachmann, M.F., and Zinkernagel, R.M., "Neutralizing Antiviral B Cell Responses," *Ann. Rev. Immunol.* 15:235-270, Annual Reviews Inc. (1997).

Bachmann, M.F., and Zinkernagel, R., "The influence of virus structure on antibody responses and virus serotype formation," *Immunol. Today* 17:553-558, Elsevier Science Ltd. (1996).

Bachmann, M.F., et al., "Induction of protective cytotoxic T cells with viral proteins," *Eur. J. Immunol.* 24:2228-2236, VCH Verlagsgesellschaft mbH (1994).

Bachmann, M.F., et al., "Distinct Roles for LFA-1 and CD28 during Activation of Naive T Cells: Adhesion versus Costimulation," *Immunity* 7:549-557, Cell Press (1997).

Bachmann, M.F., et al., "Four types of $Ca^{2+}$-signals in naïve $CD^{8+}$ cytotoxic cells after stimulation with T cell agonists, partial agonists and antagonists," *Eur. J. Immunol.* 27:3414-3419, Wiley-VCH Verlag GmbH (1997).

Bachmann, M.F., et al., "Functional Maturation of an Anti-viral Cytotoxic T-cell Response," *J. Virol.* 71:5764-5768, American Society for Microbiology (1977).

Bachmann, M.F., et al., "Peptide induced T cell receptor-down regulation on naive T cell predicts agonist/partial agonist properties and strictly correlates with T cell activation," *Eur. J. Immunol.* 27:2195-2203, Wiley VCH Verlag GmbH (1997).

Belshe, R.B., et al., "Safety and Immunogenicity of a Canarypox-Vectored Human Immunodeficiency Virus Type 1 Vaccine with or without gp120: A Phase 2 Study in Higher- and Lower-Risk Volunteers," *J. Inf. Dis.* 183:1343-1352, The Infectious Diseases Society of America (2001).

Berthet-Colominas, C., et al., "Head-to-tail dimers and interdomain flexibility revealed by the crystal structure of HIV-1 capsid protein (p24) complexed with a monoclonal antibody Fab," *EMBO J.* 18:1124-1136, European Molecular Biology Organization (1999).

Borisova, G., et al., "Hybrid Hepatitis B Virus Nucleocapsid Bearing an Immunodominant Region from Hepatitis B Virus Surface Antigen," *J. Virol.* 67:3696-3701, American Society for Microbiology (1993).

Brändle, D., et al., "The shared tumor-specific antigen encoded by mouse gene *P1A* is a target not only for cytolytic T lymphocytes but also for tumor rejection," *Eur. J. Immunol.* 28:4010-4019, Wiley VCH Verlag GmbH (1998).

Brown, W.L., et al., "RNA Bacteriophage Capsid-Mediated Drug Delivery and Epitope Presentation," *Intervirology* 45:371-380, S. Karger AG (2002).

Buonaguro, L., et al., "High efficient production of Pr55[gag] virus-like particles expressing multiple HIV-1 epitopes, including a gp 120 protein derived from an Ugandan HIV-1 isolate of subtype A," *Antiviral Res.* 49:35-47, Elsevier Science (2001).

Chackerian, B., et al., "Induction of autoantibodies to mouse CCR5 with recombinant papillomavirus particles," *Proc. Natl. Acad. Sci. USA* 96:2373-2378, National Academy of Sciences (1999).

Clarke, B.E., et al., "Presentation and immunogenicity of viral epitopes on the surface of hybrid hepatitis B virus core particles produced in bacteria," *J. Gen. Virol.* 71:1109-1117, SGM (1990).

Cohen, P.A., et al., "CD4+ T-Cells from Mice Immunized to Syngeneic Sarcomas Recognize Distinct, Non-Shared Tumor Antigens," *Cancer Res.* 54:1055-1058, American Association for Cancer Research (1994).

De Clercq, E., "Interferon Induction by Polynucleotides, Modified Polynucleotides, and Polycarboxylates," *Methods Enzymol.* 78:227-236, Academic Press, Inc. (1981).

Desrosiers, R.C., et al., "Vaccine protection against simian immunodeficiency virus infection," *Proc. Natl. Acad. Sci. USA* 86:6353-6357, National Academy of Sciences (1989).

Eckhardt, S.G., et al., "Hepatitis B Virus Core Antigen Has Two Nuclear Localization Sequences in the Arginine-Rich Carboxyl Terminus," *J. Virol.* 65:575-582, American Society for Microbiology (1991).

Engleman, E.G., "Dendritic cells: potential role in cancer therapy," *Cytotechnology* 25:1-8, Kluwer Academic Publishers (1997).

Fehr, T., et al., "T cell-independent type I antibody response against B cell epitopes expressed repetitively on recombinant virus particles," *Proc. Natl. Acad. Sci. USA* 95:9477-9481, National Academy of Sciences (1998).

Fehr, T., et al., "Role of Repetitive Antigen Patterns for Induction of Antibodies Against Antibodies," *J. Exp. Med.* 185:1785-1792, The Rockefeller University Press (1997).

Firat, H., et al., "H-2 class I knockout, HLA-A2.1-transgenic mice: a versatile animal model for preclinical evaluation of antitumor immunotherapeutic strategies," *Eur. J. Immunol.* 29:3112-3121, Wiley-VCH Verlag GmbH (1999).

Fitchen, J., et al., "Plant virus expressing hybrid coat protein with added murine epitope elicits autoantibody response," *Vaccine* 13:1051-1057, Elsevier Science, Ltd. (1995).

Franken, P., et al., "HIV-1 Nef protein: Purification, crystallizations, and preliminary X-ray diffraction studies," *Protein Sci.* 6: 2681-2683, Cold Spring Harbor Laboratory Press (1997).

Gerber, S., et al., "Human Papillomavirus Virus-Like Particles are Efficient Oral Immunogens when Coadministered with *Escherichia coli* Heat-Labile Enterotoxin Mutant R192G or CpG DNA," *J. Virol.* 75:4752-4760, American Society for Microbiology (2001).

Geysen, H.M., et al., "Use of peptide synthesis to probe viral antigens for epitopes to a resolution of a single amino acid," *Proc. Natl. Acad. Sci. USA* 81:3998-4002, National Academy of Sciences (1984).

Gilbert, S.C., et al., "A protein particle vaccine containing multiple malaria epitopes," *Nature Biotechnol.* 15:1280-1284, Nature America Publishing (1997).

Gluckman, J.C., et al., "In vitro generation of human dendritic cells and cell therapy," *Cytokines Cell. Mol. Ther.* 3:187-196, Martin Dunitz Ltd. (1997).

Goldberg, A.L., et al., "The importance of the proteasome and subsequent proteolytic steps in the generation of antigenic peptides," *Mol. Immunol.* 39:147-164, Elsevier Science Ltd. (2002).

Golmohammadi, R., et al., "The crystal structure of bacteriophage Qβ at 3.5 Å resolution," *Structure* 4:543-554, Current Biology Ltd. (1996).

Hanke, T., and McMichael, A.J., "Design and construction of an experimental HIV-1 vaccine for a year-2000 clinical trial in Kenya," *Nature Med.* 6:951-955, Nature America Inc. (2000).

Harding, C.V., and Song, R., "Phagocytic Processing of Exogenous Particulate Antigens by Macrophages for Presentation by Class I MHC Molecules'," *J. Immunol.* 153:4925-4933, The American Association of Immunologists (1994).

Huston, J.S., et al., "Protein Engineering of Single-Chain Fv Analogs and Fusion Proteins," *Methods Enzymol.* 203:46-88, Academic Press, Inc. (1991).

Jegerlehner, A., et al., "A molecular assembly system that renders antigens of choice highly repetitive for induction of protective B cell responses," *Vaccine* 20:3104-3112, Elsevier Science Ltd. (2002).

Jin, X., et al., "Dramatic Rise in Plasma Viremia after CD8+ T Cell Depletion in Simian Immunodeficiency Virus-infected Macaques," *J. Exp. Med.* 189:991-998, The Rockefeller University Press (1999).

Kaisho, T., and Akira, S., "Toll-like receptors as adjuvant receptors," *Biochim. Biophys. Acta* 1589:1-13, Elsevier Science (2002).

Kang, C.Y., et al., "Development of HIV/AIDS Vaccine Using Chimeric gag-env Virus-Like Particles," *Biol. Chem.* 380:353-364, Walter de Gruyter (1999).

Klinman, D.M., et al., "Immunotherapeutic Applications of CpG-Containing Oligodeoxynucleotides," *Drug News Perspect.* 13:289-296, Prous Science (2000).

Klovins, J., et al., "Nucleotide sequence of a ssRNA phage from *Acinetobacter*: kinship to coliphages," *J. Gen. Virol.* 83:1523-1533, SGM (2002).

Kovacsovics-Bankowski, M., et al., "Efficient major histocompatibility complex class I presentation of exogenous antigen upon phagocytosis by macrophages," *Proc. Natl. Acad. Sci. USA* 90:4942-4946, National Academy of Sciences (1993).

Kozlovska, T.M., et al., "Recombinant RNA phage Qβ capsid particles synthesized and self-assembled in *Escherichia coli*," *Gene* 137(1):133-7, Elsevier Science Publishers (1993).

Kozlovska, T. M., et al., "RNA phage Qβ Coat Protein as a Carrier for Foreign Epitopes," *Intervirology* 39:9-15, S. Karger AG (1996).

Kratz, P.A., et al., "Native display of complete foreign protein domains on the surface of hepatitis B virus capsides," *Proc. Natl. Acad. Sci. USA* 96:1915-1920, National Academy of Sciences (1999).

Krug, A., et al., "Identification of CpG oligonucleotide sequences with high induction of IFN-α/β in plasmacytoid dendritic cells," *Eur. J. Immunol.* 31:2154-2163, Wiley Verlag GmbH (2001).

Kündig, T.M., et al., "Fibroblasts as Efficient Antigen-Presenting Cells in Lymphoid Organs," *Science* 268:1343-1347, American Association for the Advancement of Science (1995).

Kuramoto, E., et al., "Oligonucleotide Sequences Required for Natural Killer Cell Activation," *Jpn. J. Cancer Res.* 83:1128-1131, Japanese Cancer Association (1992).

Lechner, F., et al., "Virus-Like Particles as a Modular System for Novel Vaccines," *Intervirology* 45:212-217, S. Karger AG (2002).

Levy, H.B., "Induction of Interferon in Vivo and in Vitro by Polynucleotides and Derivatives, and Preparation of Derivatives," *Methods Enzymol.* 78:242-251, Academic Press, Inc. (1981).

Li, Y., et al., "Vaccination Against Angiogenesis-Associated Antigens: A Novel Cancer Immunotherapy Strategy," *Curr. Mol. Med.* 3773-779, Bentham Science Publishers Ltd. (Dec. 2003).

Luo, L., et al., "Induction of V3-Specific Cytotoxic T Lymphocyte Responses by HIV *gag* Particles Carrying Multiple Immunodominant V3 Epitopes of gp120," *Virology* 240:316-325, Academic Press (1998).

Malling, H.-J., and Taudorf, E., "Allergenicity of alum-precipitated grass pollen extracts with different RAST activity," *Clin. Allergy* 17:399-404, Blackwell Scientific Publications (1987).

Martin, S.J., et al., "Immunization of human HIV-seronegative volunteers with recombinant p17/p24:Ty virus-like particles elicits HIV-1 p24-specific cellular and humoral immune responses," *AIDS* 7:1315-1323, Current Science Ltd. (1993).

McMichael, A.J., and Rowland-Jones, S.L., "Cellular immune responses to HIV," *Nature* 410:980-987, Macmillan Magazines Ltd. (2001).

Moingeon, P., "Strategies for designing vaccines eliciting Th1 responses in humans," *J. Biotechnol.* 98:189-198, Elsevier Science B.V. (2002).

Moss, R.B., et al., "In vitro immune function after vaccination with an inactivated, gp120-depleted HIV-1 antigen with immunostimulatory oligodeoxynucleotides," *Vaccine* 18:1081-1087, Elsevier Science, Ltd. (2000).

Murphey-Corb, M., et al., "A Formalin-Inactivated Whole SIV Vaccine Confers Protection in Macaques," *Science* 246:1293-1297, American Association for the Advancement of Science (1989).

Neirynck, S., et al., "A universal influenza A vaccine based on the extracellular domain of the M2 protein," *Nature Med.* 5:1157-1163, Nature America Inc. (1999).

Nieland, J.D., et al., "Chimeric Papillomavirus Virus-like Particles Induce a Murine Self-Antigen-Specific Protective and Therapeutic Antitumor Immune Response," *J. Cell. Biochem.* 73:145-152, Wiley-Liss Inc. (1999).

Notka, F., et al., "Accelerated clearance of SHIV in rhesus monkeys by virus-like particle vaccines is dependent on induction of neutralizing antibodies," *Vaccine* 18:291-301, Elsevier Science, Ltd. (2000).

Ohashi., P.S., et al., "Ablation of 'Tolerance' and Induction of Diabetes by Virus Infection in Viral Antigen Transgenic Mice," *Cell* 65:305-317, Cell Press (1991).

Oxenius, A., et al., "Stimulation of HIV-specific cellular immunity by structured treatment interruption fails to enhance viral control in chronic HIV infection," *Proc. Natl. Acad. Sci. USA* 99:13747-13752, National Academy of Sciences (2002).

Oxenius, A., et al., "CpG-containing Oligonucleotides Are Efficient Adjuvants for Induction of Protective Antiviral Immune Responses with T-Cell Peptide Vaccines," *J. Virol.* 73:4120-4126, American Society for Microbiology (1999).

Pasek, M., et al., "Hepatitis B virus genes and their expression in *E. coli*," *Nature* 282:575-579, Macmillan Journals Ltd. (1979).

Pearson, W.R., "Rapid and Sensitive Sequence Comparison with FASTP and FASTA," *Methods Enzymol.* 183:63-98, Academic Press, Inc. (1990).

Pedersen, N.C., et al., "Isolation of a T-Lymphotropic Virus from Domestic Cats with an Immunodeficiency-Like Syndrome," *Science* 235:790-793, American Association for the Advancement of Science (1987).

Pircher, H., et al., "Tolerance induction in double specific T-cell receptor transgenic mice varies with antigen," *Nature* 342:559-561, Nature Publishing Company (1989).

Preikschat, P., et al., "Expression, assembly competence and antigenic properties of hepatitis B virus core gene deletion variants from infected liver cells," *J. Gen. Virol.* 80:1777-1788, SGM (1999).

Pumpens, P., and Grens, E., "HBV Core Particles as a Carrier for B Cell/T Cell Epitopes," *Intervirology* 44:98-114, S. Karger AG (2001).

Pushko, P., et al., "Analysis of RNA phage *fr* coat protein assembly by insertion, deletion and substitution mutagenesis," *Protein Eng* 6:883-891, Oxford University Press (1993).

Rammensee, H., et al., "SYFPEITHI: database for MHC ligands and peptide motifs," *Immunogenetics* 50:213-219, Springer-Verlag (1999).

Renkvist, N., et al., "A listing of human tumor antigens recognized by T cells," *Cancer Immunol. Immunother.* 50:3-15, Springer Verlag (2001).

Roth, J.F., "The yeast Ty virus-like particles," *Yeast* 16:785-795, John Wiley & Sons Ltd. (2000).

Rueda, P., et al., "Minor Displacements in the Insertion Site Provoke Major Differences in the Induction of Antibody Responses by Chimeric Parvovirus-like Particles," *Virology* 263:89-99, Academic Press (1999).

Ruedl, C., et al., "Cross-presentation of virus-like particles by skin derived CD8⁻ dendritic cells: a dispensable role for TAP," *Eur. J. Immunol.* 32:818-825, Wiley-VCH Verlag GmbH (2002).

Salunke, D.M., et al., "Self-Assembly of Purified Polyomavirus Capsid Protein $VP_1$," *Cell* 46:895-904, Cell Press (1986).

Sasnauskas, K., et al., "Yeast Cells Allow High-Level Expression and Formation of Polyomavirus-Like Particles," *Biol. Chem.* 380:381-386, Walter de Gruyter (1999).

Shiver, J.W., et al., "Replication-imcompetent adenoviral vaccine vector elicits effective antiimmunodeciency-virus immunity," *Nature* 415:331-335, Macmillan Magazines Ltd. (2002).

Slepushkin, V.A., et al., "Protection of mice against influenza A virus challenge by vaccination with baculovirus-expressed M2 protein," *Vaccine* 13:1399-1402, Elsevier Science, Ltd. (1995).

Smiley, B.K., and Minion, F.C., "Enhanced readthrough of opal (UGA) stop codons and production of *Mycoplasma pneumoniae* P1 epitopes in *Escherichia coli*," *Gene* 134:33-40, Elsevier Science Publishers B.V. (1993).

Sparwasser, T., et al., "Immunosimulatory CpG-Oligodeoxynucleotides Cause Extramedullary Murine Hemopoiesis," *J. Immunol.* 162:2368-2374, American Association of Immunologists (1999).

Speiser, D.E., et al., "In vivo activation of melanoma-specific CD8⁺ T cells by endogenous tumor antigen and peptide vaccines. A comparison to virus-specific T cells," *Eur. J. Immunol.* 32:731-741, Wiley-VCH Verlag GmbH (2002).

Steinman, R.M., "Dendritic cells and immune-based therapies," *Exper. Hematol.* 24:859-862, International Society for Experimental Hematology (1996).

Storni, T., et al., "Critical Role for Activation of Antigen-Presenting Cells in Priming of Cytotoxic T Cell Responses After Vaccination with Virus-Like Particles," *J Immunol.* 168:2880-2886, The American Association of Immunologists (2002).

Stott, E.J., et al., "Preliminary report: protection of *Cynomolgus macaques* against simian immunodeficiency virus by fixed infected-cell vaccine," *Lancet* 336:1538-1541, Lancet Publishing Group (1990).

Taylor, K.M., et al., "Position-Dependent Processing of Peptides Presented on the Surface of Cowpea Mosaic Virus," *Biol. Chem.* 38:387-392, Walter de Gruyter (1999).

Tissot, A.C., et al., "Characterizing the functionality of recombinant T-cell receptors in vitro: a pMHC tetramer based approach," *J. Immunol. Methods* 236:147-165, Elsevier Science B.V. (2000).

Torrence, P.F., "Preparation of a Synthetic Polynucleotide Interferon Inducer," *Methods Enzymol.* 78:326-331, Academic Press, Inc. (1981).

Touze, A., et al., "Gene transfer using human polyomavirus BK virus-like particles expressed in insect cells," *J. Gen. Virol.* 82:3005-3009, SGM (2001).

Turner, B.G., and Summers, M.F., "Structural Biology of HIV," *J. Mol. Biol.* 285:1-32, Academic Press (1999).

Valmori, D., et al., "Enhanced Generation of Specific Tumor-Reactive CTL In Vitro by Selected Melan-A/MART-1 Immunodominant Peptide Analogues," *J. Immunol.* 160:1750-1758, American Association of Immunologists (1998).

Van Schooten, W., et al., "Biological properties of dendritic cells: implications to their use in the treatment of cancer," *Mol. Med. Today* 255:254-260, Elsevier Science Ltd. (1997).

Vasiljeva, I., et al., "Mosaic Qβ coats as a new presentation model," *FEBS Lett.* 431:7-11, Federation of European Biochemical Societies (1998).

Witte, L., et al., "Monoclonal antibodies targeting the VEGF receptor-2 (Flk1/KDR) as an anti-angiogenic therapeutic strategy," *Cancer Metastasis Rev.* 17:155-161, Kluwer Academic Publishers (1998).

Yuan, T.T.-T., et al., "Subtype-Independent Immature Secretion and Subtype-Dependent Replication Deficiency of a Highly Frequent, Naturally Occurring Mutation of Human Hepatitis B Virus Core Antigen." *J. Virol.* 73:10122-10128, American Society for Microbiology (1999).

Yuasa, N., et al., "Isolation and Some Characteristics of an Agent Inducing Anemia in Chicks," *Avian Dis.* 23:366-385, American Association of Avian Pathologists (1979).

Zhou, S., and Standring, D.N., "Cys Residues of the Hepatitis B Virus Capsid Protein Are Not Essential for the Assembly of Viral Core Particles but can Influence their Stability," *J. Virol.* 66:5393-5398, American Society for Microbiology (1992).

Allison (1994) Int J Technol Assess Health Care 10(1):107-20—Adjuvants and immune enhancement. Cambridge University Press.

Ballas, et al. (1996) J Immunol 157(5):1840-5—Induction of NK activity in murine and human cells by CpG motifs in oligodeoxynucleotides and bacterial DNA. The American Association of Immunologists.

Bartholomé, et al. (1999) J Interferon Cytokine Res 19(5):471-8—IFN-β interferes with the differentiation of dendritic cells from peripheral blood mononuclear cells: selective inhibition of CD40-dependent interleukin-12 secretion. Mary Ann Liebert, Inc.

Beaucage, et al. (1981) Tet Lett 22(20):1859-62—Deoxynucleoside Phosphoramidites-A New Class of Key Intermediates for Deoxypolynucleotide Synthesis, Pergamon Press Ltd.

Blackwell, et al. (Apr. 2003) J Immunol 170(8):4061-8—CpG-A-induced monocyte IFN-γ-inducible protein-10 production is regulated by plasmacytoid dendritic cell-derived IFN-α. The American Association of Immunologists, Inc.

Bousquet, et al. (1998) J Allergy Clin Immunol 102(4 Pt 1):558-62—Allergen immunotherapy: Therapeutic vaccines for allergic diseases. Mosby, Inc.

Branda, et al. (1996) J Lab Clin Med 128(3):329-38—Amplification of antibody production by phosphorothioate oligodeoxynucleotides. Modby-Year Book, Inc.

Cella, et al. (1999) Nat Med 5(8):919-23—Plasmacytoid monocytes migrate to inflamed lymph nodes and produce large amounts of type 1 interferon. Nature America Inc.

Cella, et al. (1999) J Exp Med 189(5):821-9—Maturation, activation, and protection of dendritic cells induced by double-stranded RNA. The Rockefeller University Press.

Choi, et al. (2000) Virology 275(2):249-57—Packaging of tobacco mosaic virus subgenomic RNAs by Brome mosaic virus coat protein exhibits RNA controlled polymorphism. Academic Press.

Choi, et al. (Jan. 2002) Proc Natl Acad Sci U S A 99(2):655-60—tRNA elements mediate the assembly of an icosahedral RNA virus. National Academy of Sciences.

Clark, et al. (2001) J Gen Virol 82(Pt 11):2791-7—Immunity against both polyomavirus VP1 and a transgene product induced following intranasal delivery of VP1 pseudocapsid-DNA complexes. Society for General Microbiology.

Cooper, et al. (Aug. 2004) Vaccine 22(23-24):3136-43—Safety and immunogenicity of CPG 7909 injection as an adjuvant to Fluarix influenza vaccine. Elsevier Ltd.

Dalpke, et al. (Feb. 2002) Immunology 106(1):103-12—Phosphodiester CpG oligonucleotides as adjuvants: polyguanosine runs enhance cellular uptake and improve immunostimulative activity of phosphodiester CpG oligonucleotides in vitro and in vivo. Blackwell Science Ltd.

Gavett, et al. (1995) J Exp Med 182(5):1527-36—Interleukin 12 inhibits antigen-induced airway hyperresponsiveness, inflammation, and Th2 cytokine expression in mice. The Rockefeller University Press.

Goeckeritz, et al. (1999) Int Immunol 11(10):1693-700—Multivalent cross-linking of membrane Ig sensitizes murine B cells to a broader spectrum of CpG-containing oligodeoxynucleotide motifs, including their methylated counterparts, for stimulation of proliferation and Ig secretion. Oxford University Press.

Gursel, et al. (2001) J Immunol 167(6):3324-8—Sterically stabilized cationic liposomes improve the uptake and immunostimulatory activity of CpG oligonucleotides. The American Association of Immunologists.

Häcker, et al. (1998) EMBO J 17(21):6230-40—CpG-DNA-specific activation of antigen-presenting cells requires stress kinase activity and is preceded by non-specific endocytosis and endosomal maturation. Oxford University Press.

Halperin, et al. (Jun. 2003) Vaccine 21(19-20):2461-7—A phase I study of the safety and immunogenicity of recombinant hepatitis B surface antigen co-administered with an immunostimulatory phosphorothioate oligonucleotide adjuvant. Elsevier Science Ltd.

Halpern, et al. (1996) Cell Immunol 167(1):72-8—Bacterial DNA induces murine interferon-γ production by stimulation of interleukin-12 and tumor necrosis factor-α. Academic Press, Inc.

Hartmann, et al. (2000) J Immunol 164(2):944-52—Mechanism and function of a newly identified CpG DNA motif in human primary B cells. The American Association of Immunologists.

Hartmann, et al. (1999) Proc Natl Acad Sci U S A 96(16):9305-10—CpG DNA: a potent signal for growth, activation, and maturation of human dendritic cells. National Academy of Sciences.

Heal, et al. (2000) Vaccine 18:251-8—Expression and immunogenicity of a liver stage malaria epitope presented as a foreign peptide on the surface of RNA-free MS2 bacteriophage capsids. Elsevier Science Ltd.

Heath (1994) Cancer Biother 9(1):1-6—Cytokines and the rational choice of immunological adjuvants. Mary Ann Liebert, Inc.

Hsu, et al. (1996) Nat Med 2(5):540-4—Immunoprophylaxis of allergen-induced immunoglobulin E synthesis and airway hyperresponsiveness in vivo by genetic immunization. Nature Publishing Group.

Iho, et al. (1999) J Immunol 163(7):3642-52—Oligodeoxynucleotides containing palindrome sequences with internal 5'-CpG-3' act directly on human NK and activated T cells to induce IFN-γ production in vitro. The American Association of Immunologists.

Jiang, et al. (1999) Vaccine 17(7-8):1005-13—Heterotypic protection from rotavirus infection in mice vaccinated with virus-like particles. Elsevier Science Ltd.

Jiang, et al. (1999) Hum Gene Ther 10(16):2627-36—A genetically engineered spleen necrosis virus-derived retroviral vector that displays the HIV type 1 glycoprotein 120 envelope peptide. Mary Ann Liebert, inc.

Joelson, et al. (1997) J Gen Virol 78:1213-7—Presentation of a foreign peptide on the surface of tomato bushy stunt virus. Society for General Microbiology.

Kerkmann, et al. (May 2003) J Immunol 170(9):4465-74—Activation with CpG-A and CpG-B oligonucleotides reveals two distinct regulatory pathways of type 1 IFN synthesis in human plasmacytoid dendritic cells. The American Association of Immunologists, Inc.

Kline, et al. (1998) J Immunol 160(6):2555-9—Cutting Edge: Modulation of airway inflammation by CpG oligodeoxynucleotides in a murine model of asthma. The American Association of Immunologists.

Kline, et al. (Feb. 2002) Am J Physiol Lung Cell Mol Physiol 283(1):L170-9—Treatment of established asthma in a murine model using CpG oligodeoxynucleotides. The American Physiological Society.

Klinman (Apr. 2004) Nat Rev Immunol 4(4):249-58—Immunotherapeutic uses of CpG oligodeoxynucleotides. Nature Publishing Group.

Klinman, et al. (1996) Proc Natl Acad Sci U S A 93(7):2879-83—CpG motifs present in bacterial DNA rapidly induce lymphocytes to secrete interleukin 6, interleukin 12, and interferon γ. National Academy of Sciences.

Klinman, et al. (Jul. 2004) Vaccine 22(21-22):2881-6—CpG oligonucleotides improve the protective immune response induced by the anthrax vaccination of *Rhesus macaques*. Elsevier Ltd.

Krieg (1999) Biochim Biophys Acta 1489(1):107-16—Mechanisms and applications of immune stimulatory CpG oligodeoxynucleotides. Elsevier Science B.V.

Krieg (Oct. 2002) Annu Rev Immunol 20:709-60—CpG motifs in bacterial DNA and their immune effects. Annual Reviews.

Krieg, et al. (2001) Curr Opin Mol Ther 3(1):15-24—Enhancing vaccines with immune stimulatory CpG DNA. PharmaPress Ltd.

Krieg, et al. (1995) Nature 374(6522):546-9—CpG motifs in bacterial DNA trigger direct B-cell activation. Nature Publishing Group.

Krieg, et al. (1996) Antisense Nucleic Acid Drug Dev 6(2):133-9—Oligonucleotide modifications determine the magnitude of B cell stimulation by CpG motifs. Mary Ann Liebert, Inc.

Krug, et al. (Apr. 2003) J Immunol 170(7):3468-77—CpG-A oligonucleotides induce a monocyte-derived dendritic cell-like phenotype that preferentially activates CD8 T cells. The American Association of Immunologists, Inc.

Lechner, et al. (Jan. 2002) Intervirology 45(4-6):212-7—Virus-like particles as a modular system for novel vaccines. S. Karger AG, Basel.

Lee, et al. (2000) J Immunol 165(7):3631-9—Effects of a hexameric deoxyriboguanosine run conjugation into CpG oligodeoxynucleotides on their immunostimulatory potentials. The American Association of Immunologists.

Leibl, et al. (1998) Vaccine 16(4):340-5—Adjuvant/carrier activity of inactivated tick-borne encephalitis virus. Elsevier Science Ltd.

Liljas, et al. (1994) J Mol Biol 244(3):279-90—Crystal structure of bacteriophage fr capsids at 3.5 Å resolution. Academic Press Limited.

Liu, et al. (1998) Blood 92(10):3730-6—Immunostimulatory CpG oligodeoxynucleotides enhance the immune response to vaccine strategies involving granulocyte-macrophage colony-stimulating factor. The American Society of Hematology.

Luo, et al. (1998) Virology 240(2):316-25—Induction of V3-specific cytotoxic T lymphocyte responses by HIV *gag* particles carrying multiple immunodominant V3 epitopes of gp120. Academic Press.

Mahon (2001) Curr Med Chem 8(9):1057-75—The rational design of vaccine adjuvants for mucosal and neonatal immunization. Bentham Science Publishers Ltd.

Notka, et al. (2000) Vaccine 18(3-4):291-301—Accelerated clearance of SHIV in *Rhesus* monkeys by virus-like particle vaccines is dependent on induction of neutralizing antibodies. Elsevier Science Ltd.

Oxenius, et al. (1999) J Virol 73(5):4120-6—CpG-containing oligonucleotides are efficient adjuvants for induction of protective antiviral immune responses with T-cell peptide vaccines. American Society for Microbiology.

Pestka (1986) Methods Enzymol 119:14-23—Interferon standards and general abbreviations. Academic Press, Inc.

Pisetsky, et al. (1994) Life Sci 54(2):101-7—Stimulation of murine lymphocyte proliferation by a phosphorothioate oligonucleotide with antisense activity for herpes simplex virus. Pergamon Press Ltd.

Pushko, et al. (1993) Protein Eng 6(8):883-91—Analysis of RNA phage fr coat protein assembly by insertion, deletion and substitution mutagenesis. Oxford University Press.

Raz (1997) Springer Semin Immunopathol 19(2):131-7—Introduction: gene vaccination, current concepts and future directions. Springer-Verlag.

Raz, et al. (1996) Proc Natl Acad Sci U S A 93(10):5141-5—Preferential induction of a $Th_1$ immune response and inhibition of specific IgE antibody formation by plasmid DNA immunization. National Academy of Sciences.

Sato, et al. (1996) Science 273(5273):352-4—Immunostimulatory DNA sequences necessary for effective intradermal gene immunization. American Association for the Advancement of Science.

Schwarz, et al. (Jun. 2003) Eur J Immunol 33(6):1465-70—Role of Toll-like receptors in costimulating cytotoxic T cell responses. Wiley-VCH Verlag GMBH & Co.

Serre, et al. (1998) J Immunol 161(11):6059-67—Efficient presentation of multivalent antigens targeted to various cell surface molecules of dendritic cells and surface Ig of antigen-specific B cells. The American Association of Immunologists.

Siegal, et al. (1999) Science 284(5421):1835-7—The nature of the principal type 1 interferon-producing cells in human blood. American Association for the Advancement of Science.

Takauji, et al. (Nov. 2002) J Leukoc Biol 72(5):1011-9—CpG-DNA-induced IFN-α production involves p38 MAPK-dependent STAT1 phosphorylation in human plasmacytoid dendritic cell precursors. Wiley-Liss.

Tars, et al. (1997) J Mol Biol 271(5):759-73—The crystal structure of bacteriophage GA and a comparison of bacteriophages belonging to the major groups of *Escherichia coli* leviviruses. Academic Press Limited.

Uhlmann, et al. (Mar. 2003) Curr Opin Drug Discov Devel 6(2):204-17—Recent advances in the development of immunostimulatory oligonucleotides. Current Drugs.

Van Ojik, et al. (Oct. 2002) Ann. Oncol. 13:157-158 "Phase I/II study with CpG 7909 as adjuvant to vaccination with MAGE-3 protein in patients with MAGE-3 positive tumors," Oxford University Press, Abstract No. 5790.

Verthelyi, et al. (2001) J Immunol 166(4):2372-7—Human peripheral blood cells differentially recognize and respond to two distinct CpG motifs. The American Association of Immunologists.

Verthelyi, et al. (Apr. 2004) AIDS 18(7):1003-8—CpG oligodeoxynucleotides improve the response to hepatitis B immunization in healthy and SIV-infected *Rhesus macaques*. Lippincott Williams & Wilkins.

Vrtala, et al. (1998) J Immunol 160(12):6137-44—Immunization with purified natural and recombinant allergens induces mouse IgGI antibodies that recognize similar epitopes as human IgE and inhibit the human IgE-allergen interaction and allergen-induced basophil degranulation. The American Association of Immunologists.

Warnes, et al. (1995) Gene 160(2):173-8—Expression of the measles virus nucleoprotein gene in *Escherichia coli* and assembly of nucleocapsid-like structures. Elsevier Science B.V.

Weiner, G., (2000) "Declaration of Dr. George Weiner Under 37 CFR § 1.32," submitted in support of U.S. Appl. No. 09/286,098, 9 pages.

Weiner, et al. (1997) Proc Natl Acad Sci U S A 94(20):10833-7—Immunostimulatory oligodeoxynucleotides containing the CpG motif are effective as immune adjuvants in tumor antigen immunization. The National Academy of Sciences.

Yamamoto, et al. (1992) J Immunol 148(12):4072-6—Unique palindromic sequences in synthetic oligonucleotides are required to induce IFN [correction of INF] and augment IFN-mediated [correction of INF] natural killer activity. The American Association of Immunologists.

Yamamoto, et al. (1994) Antisense Res Dev 4(2):119-22—Ability of oligonucleotides with certain palindromes to induce interferon production and augment natural killer cell activity is associated with their base length. Mary Ann Liebert, Inc.

Yamamoto, et al. (1994) Jpn J Cancer Res 85(8):775-9—Synthetic oligonucleotides with certain palindromes stimulate interferon production of human peripheral blood lymphocytes in vitro. Japanese Cancer Association.

Yamamoto, et al. (2000) Springer Semin Immunopathol 22(1-2):11-9—The discovery of immunostimulatory DNA sequence. Springer-Verlag.

Yu, et al. (Sep. 2002) Biochem Biophys Res Commun 297(1):83-90—Potent CpG oligonucleotides containing phosphodiester linkages: in vitro and in vivo immunostimulatory properties. Elsevier Science (USA).

Zlotnick, et al. (2000) Virology 277(2):450-6—Mechanism of capsid assembly for an icosahedral plant virus. Academic Press.

* cited by examiner

US 7,517,520 B2

PACKAGING OF IMMUNOSTIMULATORY OLIGONUCLEOTIDES INTO VIRUS-LIKE PARTICLES: METHOD OF PREPARATION AND USE

CROSS-REFERENCE TO RELATED APPLICATIONS

This application is a U.S. National Phase of International Application PCT/EP2004/003165, international filing date of Mar. 25, 2004; and claims the benefit of the filing date of U.S. Provisional Application 60/457,348, filed Mar. 26, 2003; all of which is herein incorporated by reference.

BACKGROUND OF THE INVENTION

1. Field of the Invention

The present invention is related to the fields of vaccinology, immunology and medicine. The invention provides compositions and methods for enhancing immunological responses against virus-like particles (VLPs) or against antigens coupled, fused or attached otherwise to VLPs by packaging immunostimulatory substances, in particular immunostimulatory nucleic acids, and even more particular oligonucleotides containing at least one non-methylated CpG sequence, into the VLPs. The invention can be used to induce strong and sustained T cell responses particularly useful for the treatment of tumors and chronic viral diseases as well as allergies and other chronic diseases.

2. Related Art

The essence of the immune system is built on two separate foundation pillars: one is specific or adaptive immunity which is characterized by relatively slow response-kinetics and the ability to remember; the other is non-specific or innate immunity exhibiting rapid response-kinetics but lacking memory.

It is well established that the administration of purified proteins alone is usually not sufficient to elicit a strong immune response; isolated antigen generally must be given together with helper substances called adjuvants. Within these adjuvants, the administered antigen is protected against rapid degradation, and the adjuvant provides an extended release of a low level of antigen.

Unlike isolated proteins, viruses induce prompt and efficient immune responses in the absence of any adjuvants both with and without T-cell help (Bachmann & Zinkernagel, Ann. Rev. Immunol. 15:235-270 (1997)). Many viruses exhibit a quasi-crystalline surface that displays a regular array of epitopes which efficiently crosslinks epitope-specific immunoglobulins on B cells (Bachmann & Zinkernagel, Immunol. Today 17:553-558 (1996)). Viral structure is even linked to the generation of anti-antibodies in autoimmune disease and as a part of the natural response to pathogens (see Fehr, T., et al., J. Exp. Med. 185:1785-1792 (1997)). Thus, antigens on viral particles that are organized in an ordered and repetitive array are highly immunogenic since they can directly activate B cells and induce the generation of a cytotoxic T cell response, another crucial arm of the immune system.

Viral particles as antigens exhibit two advantages over their isolated components: (1) due to their highly repetitive surface structure, they are able to directly activate B cells, leading to high antibody titers and long-lasting B cell memory; and (2) viral particles, but not soluble proteins, have the potential to induce a cytotoxic T cell response, even if the viruses are non-infectious and adjuvants are absent.

Several new vaccine strategies exploit the inherent immunogenicity of viruses. Some of these approaches focus on the particulate nature of the virus particle; for example see Harding, C. V. and Song, R., (J. Immunology 153:4925 (1994)), which discloses a vaccine consisting of latex beads and antigen; Kovacsovics-Bankowski, M., et al. (Proc. Natl. Acad. Sci. USA 90:4942-4946 (1993)), which discloses a vaccine consisting of iron oxide beads and antigen; U.S. Pat. No. 5,334,394 to Kossovsky, N., et al., which discloses core particles coated with antigen; U.S. Pat. No. 5,871,747, which discloses synthetic polymer particles carrying on the surface one or more proteins covalently bonded thereto; and a core particle with a non-covalently bound coating, which at least partially covers the surface of said core particle, and at least one biologically active agent in contact with said coated core particle (see, e.g., WO 94/15585).

In a further development, virus-like particles (VLPs) are being exploited in the area of vaccine production because of both their structural properties and their non-infectious nature. VLPs are supermolecular structures built in a symmetric manner from many protein molecules of one or more types. They lack the viral genome and, therefore, are noninfectious. VLPs can often be produced in large quantities by heterologous expression and can be easily be purified.

In addition, DNA rich in non-methylated CG motifs (CpG), as present in bacteria and most non-vertebrates, exhibits a potent stimulatory activity on B cells, dendritic cells and other APC's in vitro as well as in vivo. Although bacterial DNA is immunostimulatory across many vertebrate species, the individual CpG motifs may differ. In fact, CpG motifs that stimulate mouse immune cells may not necessarily stimulate human immune cells and vice versa.

Although DNA oligomers rich in CpG motifs can exhibit immunostimulatory capacity, their efficiency is often limited, since they are unstable in vitro and in vivo. Thus, they exhibit unfavorable pharmacokinetics. In order to render CpG-oligonucleotides more potent, it is therefore usually necessary to stabilize them by introducing phosphorothioate modifications of the phosphate backbone.

A second limitation for the use of CpG-oligonucleotides to stimulate immune responses is their lack of specificity, since all APC's and B cells in contact with CpG-oligonucleotides become stimulated. Thus, the efficiency and specificity of CpG-oligonucleotides may be improved by stabilizing them or packaging them in a way that restricts cellular activation to those cells that also present the relevant antigen.

In addition, immunostimulatory CpG-oligodeoxynucleotides induce strong side effects by causing extramedullary hemopoiesis accomponied by splenomegaly and lymphadenopathy in mice (Sparwasser et al., J. Immunol. (1999), 162: 2368-74 and Example 18).

VLPs have been shown to be efficiently presented on MHC class I molecules as they, presumably after uptake by macropinocytosis, are efficiently processed and crossprimed onto MHC class I. The mechanism of crosspriming is not clear to date, but TAP-dependent and TAP-independent pathways have been proposed.

There have been remarkable advances made in vaccination strategies recently, yet there remains a need for improvement on existing strategies. In particular, there remains a need in the art for the development of new and improved vaccines that promote a strong CTL immune response and anti-pathogenic protection as efficiently as natural pathogens in the absence of generalized activation of APCs and other cells.

SUMMARY OF THE INVENTION

This invention is based on the surprising finding that specific immunostimulatory substances such as DNA oligonucleotides packaged into VLPs renders them more immunogenic. Unexpectedly, the nucleic acids and oligonucleotides, respectively, present in VLPs can be replaced specifically by the immunostimulatory substances and DNA-oligonucleotides containing CpG motifs, respectively. Surprisingly, these packaged immunostimulatory substances, in particular immunostimulatory nucleic acids such as unmethylated CpG-containing oligonucleotides retained their immunostimulatory capacity without widespread activation of the innate immune system. The compositions comprising VLP's and the immunostimulatory substances in accordance with the present invention, and in particular the CpG-VLPs are dramatically more immunogenic than their CpG-free counterparts and induce enhanced B and T cell responses. The immune response against antigens optionally coupled, fused or attached otherwise to the VLPs is similarly enhanced as the immune response against the VLP itself. In addition, the T cell responses against both the VLPs and antigens are especially directed to the Th1 type. Antigens attached to CpG-loaded VLPs may therefore be ideal vaccines for prophylactic or therapeutic vaccination against allergies, tumors and other self-molecules and chronic viral diseases.

In a first embodiment, the invention provides a composition, typically and preferably for enhancing an immune response in an animal, comprising a virus-like particle and an immunostimulatory substance, preferably an immunostimulatory nucleic acid, an even more preferably an unmethylated CpG-containing oligonucleotide, where the substance, nucleic acid or oligonucleotide is coupled, fused, or otherwise attached to or enclosed by, i.e., bound, to the virus-like particle. In another embodiment, the composition further comprises an antigen bound to the virus-like particle.

In a preferred embodiment of the invention, the immunostimulatory nucleic acids, in particular the unmethylated CpG-containing oligonucleotides are stabilized by phosphorothioate modifications of the phosphate backbone. In another preferred embodiment, the immunostimulatory nucleic acids, in particular the unmethylated CpG-containing oligonucleotides are packaged into the VLPs by digestion of RNA within the VLPs and simultaneous addition of the DNA oligonucleotides containing CpGs of choice. In an equally preferred embodiment, the VLPs can be disassembled before they are reassembled in the presence of CpGs.

In a further preferred embodiment, the immunostimulatory nucleic acids do not contain CpG motifs but nevertheless exhibit immunostimulatory activities. Such nucleic acids are described in WO 01/22972. All sequences described therein are hereby incorporated by way of reference.

In a further preferred embodiment, the virus-like particle is a recombinant virus-like particle. Also preferred, the virus-like particle is free of a lipoprotein envelope. Preferably, the recombinant virus-like particle comprises, or alternatively consists of, recombinant proteins of Hepatitis B virus, BK virus or other human Polyoma virus, measles virus, Sindbis virus, Rotavirus, Foot-and-Mouth-Disease virus, Retrovirus, Norwalk virus or human Papilloma virus, RNA-phages, Qβ-phage, GA-phage, fr-phage and Ty. In a specific embodiment, the virus-like particle comprises, or alternatively consists of, one or more different Hepatitis B virus core (capsid) proteins (HBcAgs).

In a further preferred embodiment, the virus-like particle comprises recombinant proteins, or fragments thereof, of a RNA-phage. Preferred RNA-phages are Qβ-phage, AP 205-phage, GA-phage, fr-phage In another embodiment, the antigen is a recombinant antigen. In yet another embodiment, the antigen can be selected from the group consisting of: (1) a polypeptide suited to induce an immune response against cancer cells; (2) a polypeptide suited to induce an immune response against infectious diseases; (3) a polypeptide suited to induce an immune response against allergens; (4) a polypeptide suited to induce an improved response against self-antigens; and (5) a polypeptide suited to induce an immune response in farm animals or pets.

In yet another embodiment, the antigen can be selected from the group consisting of: (1) an organic molecule suited to induce an immune response against cancer cells; (2) an organic molecule suited to induce an immune response against infectious diseases; (3) an organic molecule suited to induce an immune response against allergens; (4) an organic molecule suited to induce an improved response against self-antigens; (5) an organic molecule suited to induce an immune response in farm animals or pets; and (6) an organic molecule suited to induce a response against a drug, a hormone or a toxic compound.

In a particular embodiment, the antigen comprises, or alternatively consists of, a cytotoxic T cell epitope, preferably a Th cell epitope or a combination of at least two of the epitopes, wherein preferably the at least two epitopes are bound directly or by way of a linking sequence. In one embodiment, the cytotoxic T cell epitope is a viral or a tumor cytotoxic T cell epitope. In a related embodiment, the virus-like particle comprises the Hepatitis B virus core protein and the cytotoxic T cell epitope is fused to the C-terminus of said Hepatitis B virus core protein, preferably by way of a linking sequence. In another embodiment, the virus-like particle comprises the BK virus VP1 protein and the cytotoxic T cell epitope is fused to the C-terminus of the BK virus VP1 protein, preferably by way of a linking sequence. In one embodiment, they are fused by a leucine linking sequence.

In another aspect of the invention, there is provided a method of enhancing an immune response in a human or other animal species comprising introducing into the animal a composition comprising a virus-like particle and immunostimulatory substance, preferably an immunostimulatory nucleic acid, an even more preferably an unmethylated CpG-containing oligonucleotide where the substance, preferably the nucleic acid, and even more preferably the oligonucleotide is bound (i.e. coupled, attached or enclosed) to the virus-like particle. In a further embodiment, the composition further comprises an antigen bound to the virus-like particle.

In yet another embodiment of the invention, the composition is introduced into an animal subcutaneously, intramuscularly, intranasally, intradermally, intravenously or directly into a lymph node. In an equally preferred embodiment, the immune enhancing composition is applied locally, near a tumor or local viral reservoir against which one would like to vaccinate.

In a preferred aspect of the invention, the immune response is a T cell response, and the T cell response against the antigen is enhanced. In a specific embodiment, the T cell response is a cytotoxic T cell response, and the cytotoxic T cell response against the antigen is enhanced.

The present invention also relates to a vaccine comprising an immunologically effective amount of the immune enhancing composition of the present invention together with a pharmaceutically acceptable diluent, carrier or excipient. In a preferred embodiment, the vaccine further comprises at least one adjuvant, such as incomplete Freund's adjuvant. The invention also provides a method of immunizing and/or treating an animal comprising administering to the animal an immunologically effective amount of the disclosed vaccine.

In a preferred embodiment of the invention, the immunostimulatory substance-containing VLPs, preferably the immunostimulatory nucleic acid-containing VLP's, an even more preferably the unmethylated CpG-containing oligonucleotide VLPs are used for vaccination of animals or humans against the VLP itself or against antigens coupled, fused or attached otherwise to the VLP. The modified VLPs can be used to vaccinate against tumors, viral diseases, self-molecules and self antigens, respectively, or non-peptidic small molecules, for example. The vaccination can be for prophylactic or therapeutic purposes, or both. Also, the modified VLPs can be used to vaccinate against allergies in order to induce immune-deviation.

In the majority of cases, the desired immune response will be directed against antigens coupled, fused or attached otherwise to the immunostimulatory substance-containing VLPs, preferably the immunostimulatory nucleic acid-containing VLP's, an even more preferably the unmethylated CpG-containing oligonucleotide VLPs. The antigens can be peptides, proteins, domains, carbohydrates or small molecules such as, for example, steroid hormones or drugs, such as nicotine. Under some conditions, the desired immune response can be directed against the VLP itself. This latter application will be used in cases where the VLP originates from a virus against which one would like to vaccinate.

The route of injection is preferably subcutaneous or intramuscular, but it would also be possible to apply the CpG-containing VLPs intradermally, intranasally, intravenously or directly into the lymph node. In an equally preferred embodiment, the CpG-containing antigen-coupled or free VLPs are applied locally, near a tumor or local viral reservoir against which one would like to vaccinate.

It is to be understood that both the foregoing general description and the following detailed description are exemplary and explanatory only and are intended to provide further explanation of the invention as claimed.

BRIEF DESCRIPTION OF THE DRAWINGS/FIGURES

FIG. 1 shows the SDS-PAGE analysis of Qb-MelanA VLPs. MelanA-peptides were coupled to Qb VLPs, as described in Example 22. The final products were mixed with sample buffer and separated under reduced conditions on 16% Novex®Tris-Glycine gels for 1.5 hours at 125 V. The separated proteins were stained by soaking the gel in Coomassie blue solution. Background staining was removed by washing the gel in 50% methanol, 8% acetic acid. The Molecular weight marker (P 77085, New England BioLabs, Beverly, USA) was used as reference for Qb-MelanA migration velocity (lane 1). 14 µg of either Qb alone (lane 2) or Qb derivatized with SMPH (lane 3) were loaded for comparison with 8 µg of each final product: Qb-MelanA 16-35 (lane 4), Qb-MelanA 16-35 A/L (lane 5), Qb-MelanA 26-35 (lane 6) and Qb-MelanA 26-35 A/L (lane7).

Figure 2A:
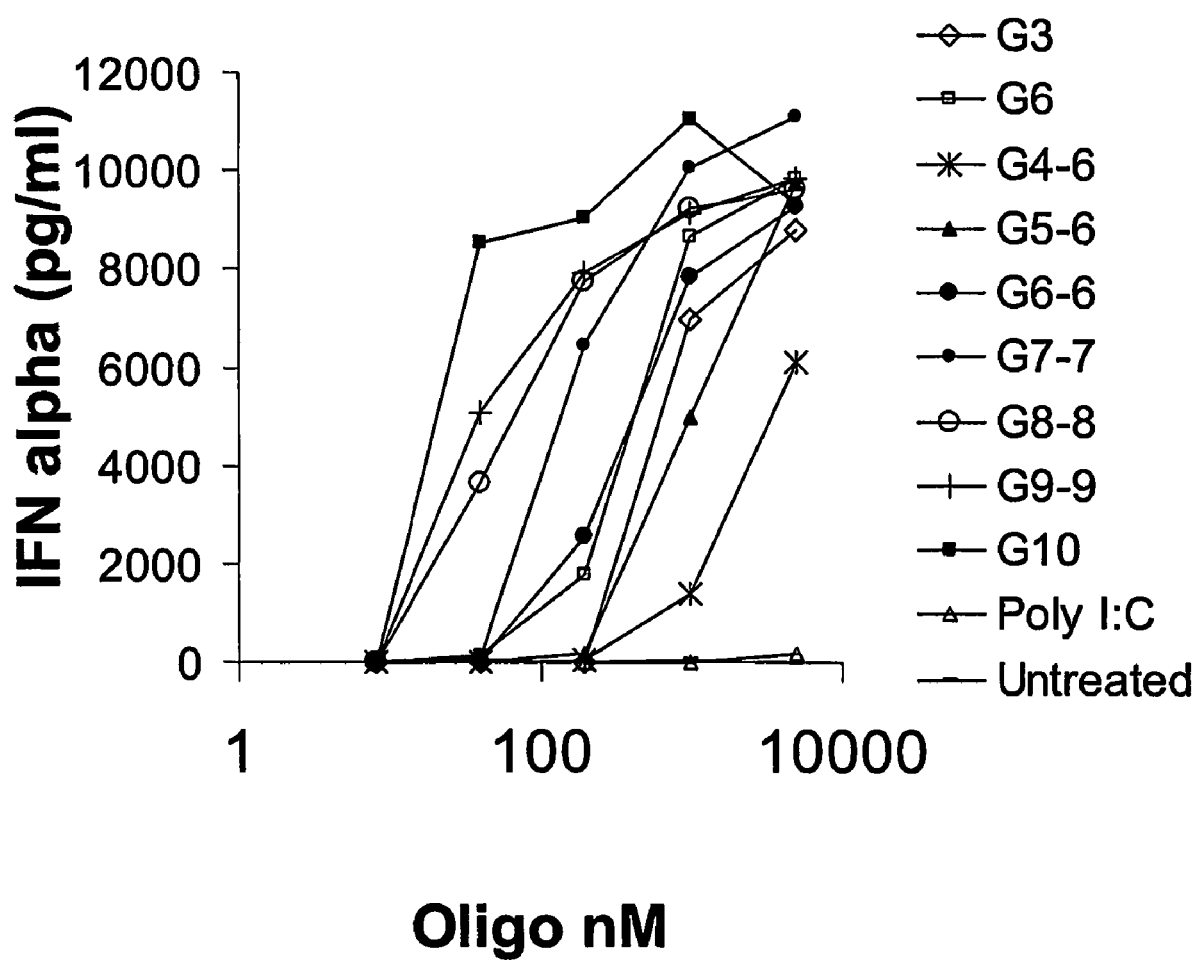

FIG. 2A shows IFN alpha released in the supernatants of ISS-treated human PBMC. PBMC were obtained from buffy coat and incubated with fivefold dilution of the indicated ISS for 18 h. The term G10 is used for the the oligonucleotide G10-PO, and the term G3 is used for the oligonucleotide G3-6). Supernatants were collected and IFN alpha was measured by ELISA, using a set of antibodies provided by PBL Biomedical Laboratories.

Figure 2B:
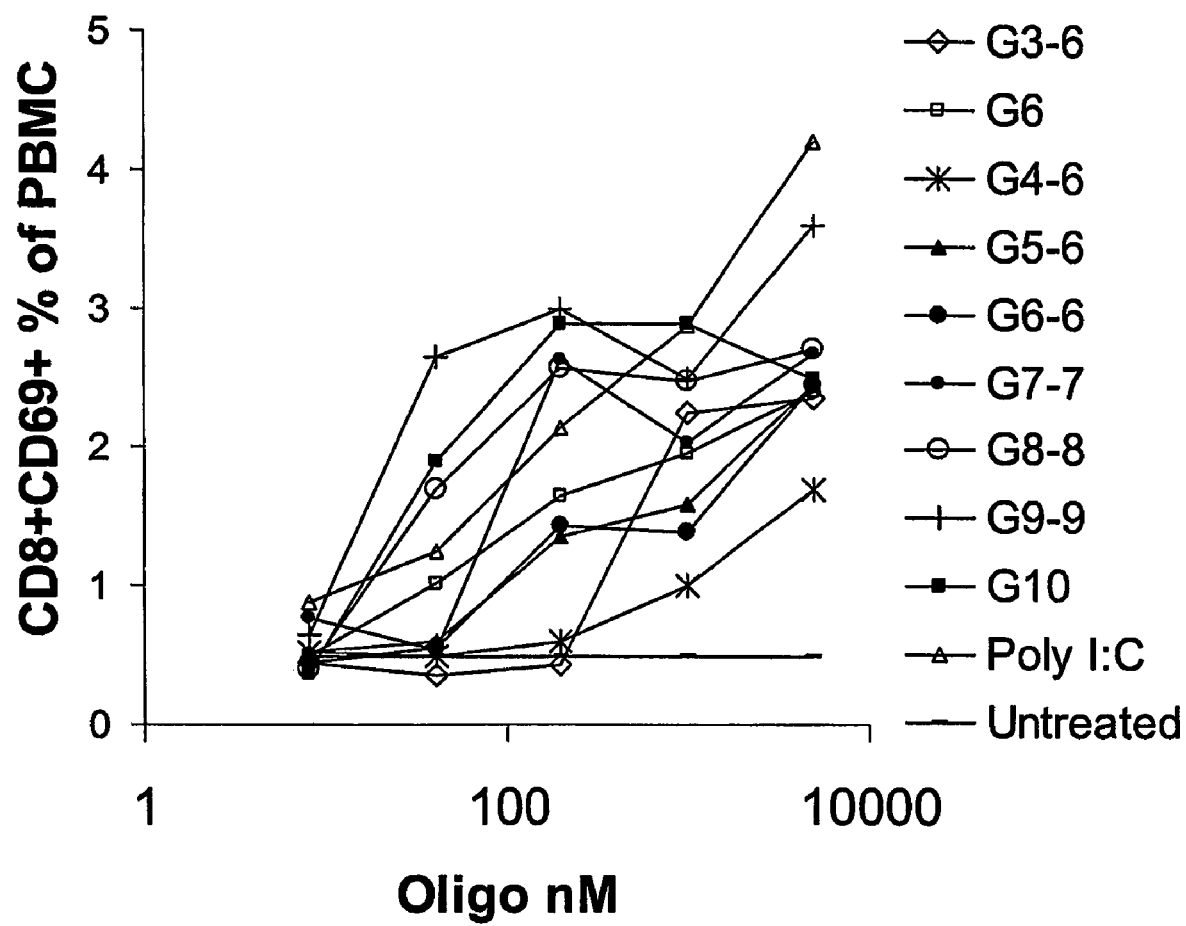

FIG. 2B shows the upregulation of CD69 on human CD8+ PBMC treated with ISS. PBMC were obtained from buffy coat and incubated with fivefold dilution of the indicated ISS for 18 h. Cells were washed and incubated with anti-CD8-FITC, anti-CD19-PE and anti-CD69-APC (all from BD PharMingen) for 20 min on ice. After washing, cells were analysed on a FACS Calibur using CellQuest software.

Figure 3:
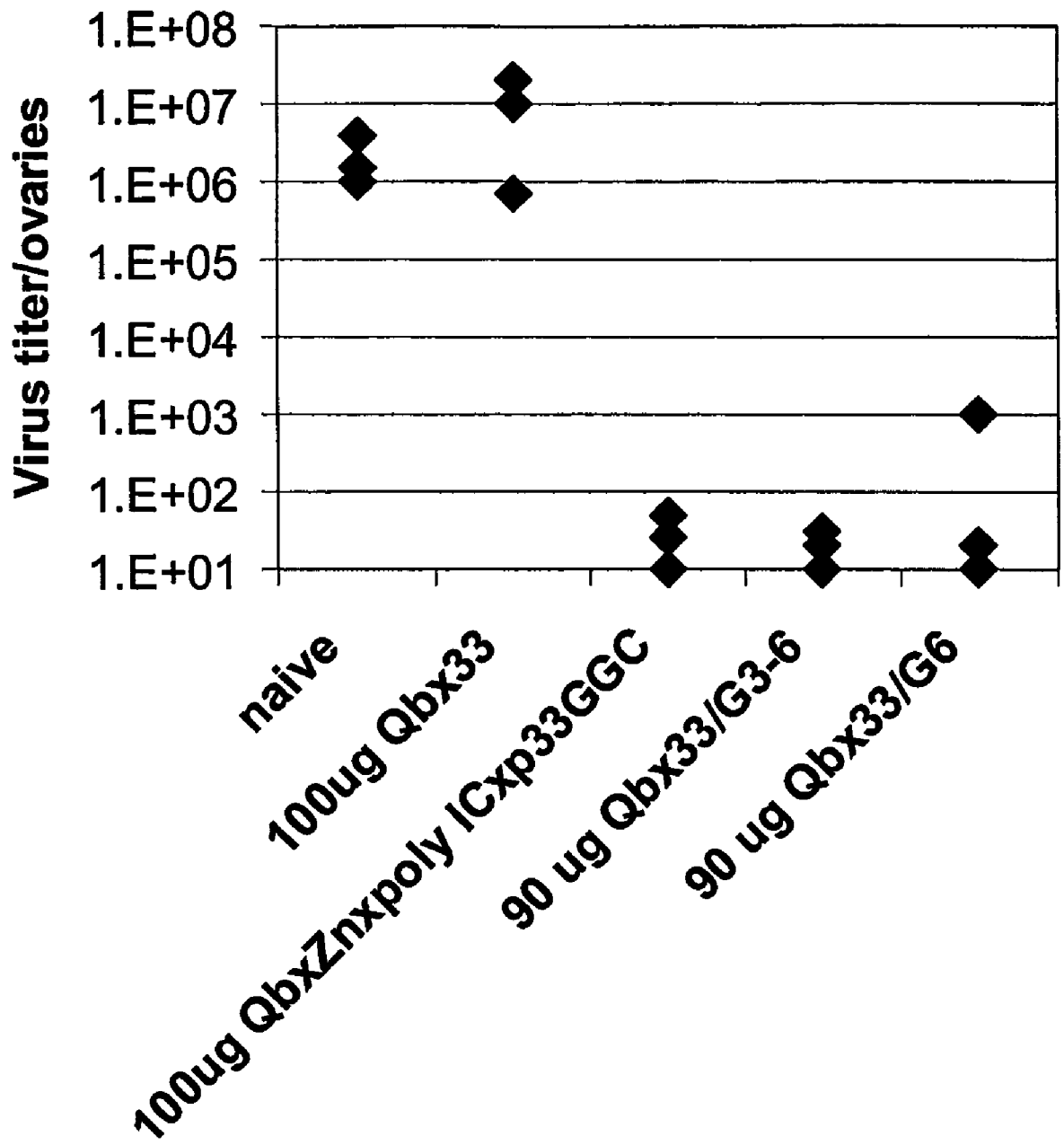

FIG. 3 shows the virus titers after immunizing mice with Qbx33 packaged with poly (I:C), G3-6, or G6. C57B16 mice were immunized by injecting either 100 µg Qbx33, 100 µg Qb VLPs packaged with poly (I:C) and coupled to p33 (Qb-pIC-33, also termed QbxZnxpolyICxp33GGC), 90 µg Qbx33 packaged with G3-6 (Qbx33/G3-6), or 90 µg Qbx33 packaged with G6 (Qbx33/G6). After eight days, mice were challenged with 1.5×106 plaque forming units Vaccinia virus, carrying the LCMV-p33 epitope. Five days later, mice were sacrificed and the ovaries were collected. A single cell suspension from the ovaries was prepared and added to BCS40 cells in serial dilutions. One day later, the cell layer was stained with a solution containing 50% Ethanol, 2% formaldehyde, 0.8% NaCl and 0.5% Crystal violet) and the viral plaques were counted.

Figure 4:
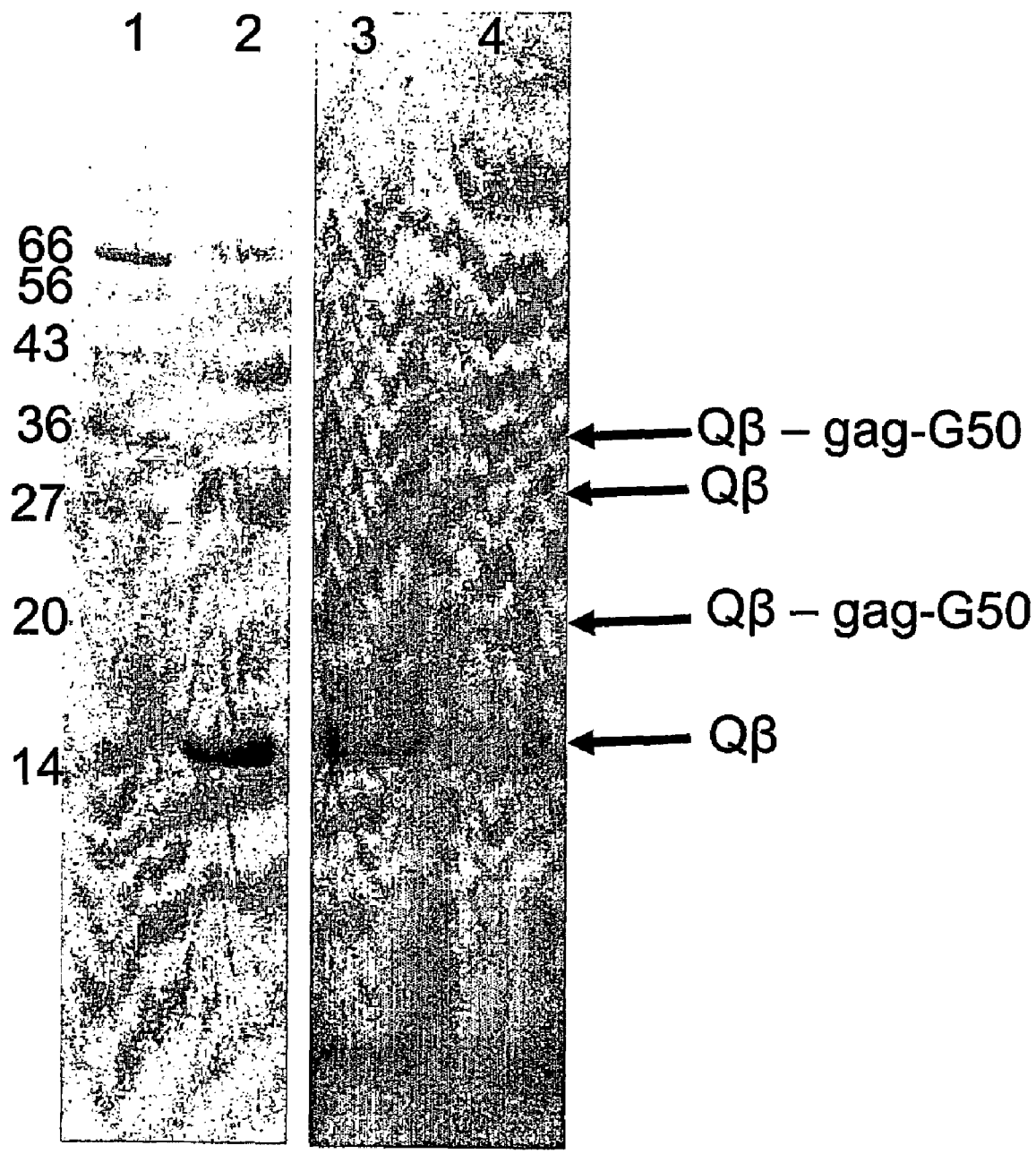

FIG. 4 shows the SDS-PAGE analysis of the coupling reaction of Qβ VLP to gag-G50 peptide. The samples were run under reducing conditions on a 12% NuPage gel (Invitrogen). Lane 1 is the protein marker, with corresponding molecular weights indicated on the left border of the gel; lane 2, derivatized Qβ VLP; lane 3, the supernatant of the coupling reaction of Qβ capsid protein to the gag-G50 peptide; lane 4, the pellet of the coupling reaction of Qβ capsid protein to the gag-G50 peptide. Coupling products corresponding to the coupling of a peptide on a Qβ monomer or Qβ dimer are indicated by arrows in the Figure.

Figure 5:
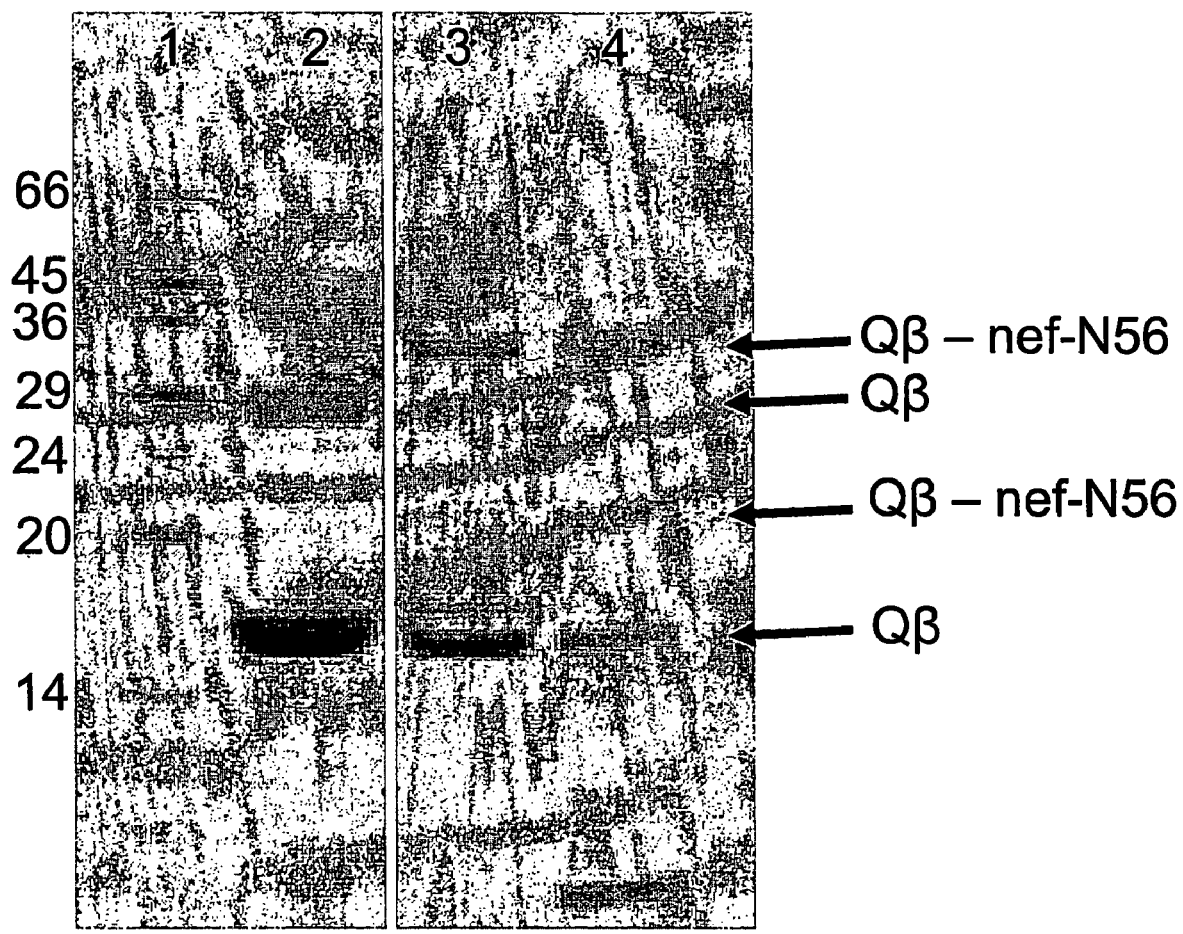

FIG. 5 shows the SDS-PAGE analysis of the coupling reaction of Qβ VLP to nef-N56 peptide. The samples were run under reducing conditions on a 12% NuPage gel (Invitrogen). Lane 1 is the protein marker, with corresponding molecular weights indicated on the left border of the gel; lane 2, derivatized Qβ VLP; lane 3, the supernatant of the coupling reaction of Qβ capsid protein to the nef-N56 peptide; lane 4, the pellet of the coupling reaction of Qβ capsid protein to the nef-N56 peptide. Coupling products corresponding to the coupling of a peptide on a Qβ monomer or Qβ dimer are indicated by arrows in the Figure.

DETAILED DESCRIPTION OF THE INVENTION

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are hereinafter described.

1. Definitions

Amino acid linker: An "amino acid linker", or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occuring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1-C6 alkyl-, cycloalkyl (C5,C6), aryl or heteroaryl moiety. However, in addition to an amino acid linker, a linker comprising preferably a C1-C6 alkyl-, cycloalkyl-(C5,C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

Animal: As used herein, the term "animal" is meant to include, for example, humans, sheep, horses, cattle, pigs, dogs, cats, rats, mice, mammals, birds, reptiles, fish, insects and arachnids.

Antibody: As used herein, the term "antibody" refers to molecules which are capable of binding an epitope or antigenic determinant. The term is meant to include whole antibodies and antigen-binding fragments thereof, including single-chain antibodies. Most preferably the antibodies are human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are human, murine, rabbit, goat, guinea pig, camel, horse or chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598 by Kucherlapati et al.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a T helper cell epitope (Th cell epitope) and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

A "microbial antigen" as used herein is an antigen of a microorganism and includes, but is not limited to, infectious virus, infectious bacteria, parasites and infectious fungi. Such antigens include the intact microorganism as well as natural isolates and fragments or derivatives thereof and also synthetic or recombinant compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to the skilled artisan.

Examples of infectious viruses that have been found in humans include but are not limited to: Retroviridae (e.g. human immunodeficiency viruses, such as HIV-1 (also referred to as HTLV-III, LAV or HTLV-III/LAV, or HIV-III); and other isolates, such as HIV-LP); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to, *Pasteurella* species, *Staphylococci* species and *Streptococcus* species. Gram negative bacteria include, but are not limited to, *Escherichia coli, Pseudomonas* species, and *Salmonella* species. Specific examples of infectious bacteria include but are not limited to: *Helicobacter pyloris, Borelia burgdorferi, Legionella pneumophilia, Mycobacteria* sps. (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia, Actinomyces israelli* and *Chlamydia*.

Examples of infectious fungi include: *Cryptococcus neoformans, Histoplasma capsulatum, Coccidioides immitis, Blastomyces dermatitidis, Chlamydia trachomatis* and *Candida albicans*. Other infectious organisms (i.e., protists) include: *Plasmodium* such as *Plasmodium falciparum, Plasmodium malariae, Plasmodium ovale, Plasmodium vivax, Toxoplasma gondii* and *Shistosoma*.

Other medically relevant microorganisms have been descried extensively in the literature, e.g., see C. G. A. Thomas, "Medical Microbiology", Bailliere Tindall, Great Britain 1983, the entire contents of which is hereby incorporated by reference.

The compositions and methods of the invention are also useful for treating cancer by stimulating an antigen-specific immune response against a cancer antigen. A "tumor antigen" as used herein is a compound, such as a peptide, associated with a tumor or cancer and which is capable of provoking an immune response. In particular, the compound is capable of provoking an immune response when presented in the context of an MHC molecule. Tumor antigens can be prepared from cancer cells either by preparing crude extracts of cancer cells, for example, as described in Cohen, et al., Cancer Research, 54:1055 (1994), by partially purifying the antigens, by recombinant technology or by de novo synthesis of known antigens. Tumor antigens include antigens that are antigenic portions of or are a whole tumor or cancer polypeptide. Such antigens can be isolated or prepared recombinantly or by any other means known in the art. Cancers or tumors include, but are not limited to, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

Antigenic determinant: As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors.

Antigen presenting cell: As used herein, the term "antigen presenting cell" is meant to refer to a heterogenous population of leucocytes or bone marrow derived cells which possess an immunostimulatory capacity. For example, these cells are capable of generating peptides bound to MHC molecules that can be recognized by T cells. The term is synonymous with the term "accessory cell" and includes, for example, Langerhans' cells, interdigitating cells, B cells, macrophages and dendritic cells. Under some conditions, epithelial cells, endothelial cells and other, non-bone marrow derived cells may also serve as antigen presenting cells.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent, and again more preferably the association is through at least one, preferably one, non-peptide bond. As used herein, the term "association" as it applies to the first and second attachment sites, not only encompass the direct binding or association of the first and second attachment site forming the compositions of the invention but also, alternatively and preferably, the indirect association or binding of the first and second attachment site leading to the compositions of the invention, and hereby typically and preferably by using a heterobifunctional cross-linker.

Attachment Site, First: As used herein, the phrase "first attachment site" refers to an element of non-natural or natural origin, typically and preferably being comprised by the virus-like particle, to which the second attachment site typically and preferably being comprised by the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the virus-like particle. Multiple first attachment sites are present on the surface of virus-like particle typically in a repetitive configuration. Preferably, the first attachment site is a amino acid or a chemically reactive group thereof.

Attachment Site, Second: As used herein, the phrase "second attachment site" refers to an element associated with, typically and preferably being comprised by, the antigen or antigenic determinant to which the first attachment site located on the surface of the virus-like particle may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is of non-natural origin, i.e. not naturally occurring within the antigen or antigenic determinant, these antigen or antigenic constructs comprise an "amino acid linker".

Bound: As used herein, the term "bound" refers to binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled", "fused", "associatede" and "attached". Moreover, with respect to the immunostimulatory substance being bound to the virus-like particle the term "bound" also includes the enclosement, or partial enclosement, of the immunostimulatory substance. Therefore, with respect to the immunostimulatory substance being bound to the virus-like particle the term "bound" is broader than and includes terms such as "coupled," "fused," "enclosed", "packaged" and "attached." For example, the immunostimulatory substance such as the unmethylated CpG-containing oligonucleotide can be enclosed by the VLP without the existence of an actual binding, neither covalently nor non-covalently.

Coat protein(s): As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qβ comprise the "Qβ CP" as well as the A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

Coupled: As used herein, the term "coupled" refers to attachment by covalent bonds or by strong non-covalent interactions. With respect to the coupling of the antigen to the virus-like particle the term "coupled" preferably refers to attachment by covalent bonds. Moreover, with respect to the coupling of the antigen to the virus-like particle the term "coupled" preferably refers to association and attachment, respectively, by at least one non-peptide bond. Any method normally used by those skilled in the art for the coupling of biologically active materials can be used in the present invention.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

CpG: As used herein, the term "CpG" refers to an oligonucleotide which contains at least one unmethylated cytosine, guanine dinucleotide sequence (e.g. "CpG DNA" or DNA containing a cytosine followed by guanosine and linked by a phosphate bond) and stimulates/activates, e.g. has a mitogenic effect on, or induces or increases cytokine expression by, a vertebrate cell. For example, CpGs can be useful in activating B cells, NK cells and antigen-presenting cells, such as monocytes, dendritic cells and macrophages, and T cells. The CpGs can include nucleotide analogs such as analogs containing phosphorothioester bonds and can be double-stranded or single-stranded. Generally, double-stranded molecules are more stable in vivo, while single-stranded molecules have increased immune activity.

Epitope: As used herein, the term "epitope" refers to portions of a polypeptide having antigenic or immunogenic activity in an animal, preferably a mammal, and most preferably in a human. An "immunogenic epitope," as used herein, is defined as a portion of a polypeptide that elicits an antibody response or induces a T-cell response in an animal, as determined by any method known in the art. (See, for example, Geysen et al., Proc. Natl. Acad. Sci. USA 81:3998 4002 (1983)). The term "antigenic epitope," as used herein, is defined as a portion of a protein to which an antibody can immunospecifically bind its antigen as determined by any method well known in the art. Immunospecific binding excludes non specific binding but does not necessarily exclude cross reactivity with other antigens. Antigenic epitopes need not necessarily be immunogenic. Antigenic epitopes can also be T-cell epitopes, in which case they can be bound immunospecifically by a T-cell receptor within the context of an MHC molecule.

An epitope can comprise 3 amino acids in a spatial conformation which is unique to the epitope. Generally, an epitope consists of at least about 5 such amino acids, and more usually, consists of at least about 8-10 such amino acids. If the epitope is an organic molecule, it may be as small as Nitrophenyl.

Immune response: As used herein, the term "immune response" refers to a humoral immune response and/or cellular immune response leading to the activation or proliferation of B- and/or T-lymphocytes. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant.

Immunization: As used herein, the terms "immunize" or "immunization" or related terms refer to conferring the ability to mount a substantial immune response (comprising antibodies or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

Immunostimulatory nucleic acid: As used herein, the term immunostimulatory nucleic acid refers to a nucleic acid capable of inducing and/or enhancing an immune response. Immunostimulatory nucleic acids, as used herein, comprise ribonucleic acids and in particular deoxyribonucleic acids. Preferably, immunostimulatory nucleic acids contain at least one CpG motif e.g. a CG dinucleotide in which the C is unmethylated. The CG dinucleotide can be part of a palindromic sequence or can be encompassed within a non-palindromic sequence. Immunostimulatory nucleic acids not containing CpG motifs as described above encompass, by way of example, nucleic acids lacking CpG dinucleotides, as well as nucleic acids containing CG motifs with a methylated CG dinucleotide. The term "immunostimulatory nucleic acid" as used herein should also refer to nucleic acids that contain modified bases such as 4-bromo-cytosine.

Immunostimulatory substance: As used herein, the term "immunostimulatory substance" refers to a substance capable of inducing and/or enhancing an immune response. Immunostimulatory substances, as used herein, include, but are not limited to, toll-like receptor activing substances and substances inducing cytokine secretion. Toll-like receptor activating substances include, but are not limited to, immunostimulatory nucleic acids, peptideoglycans, lipopolysaccharides, lipoteichonic acids, imidazoquinoline compounds, flagellins, lipoproteins, and immunostimulatory organic substances such as taxol.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 0.5 to 30 nanometers, more preferably 3 to 15 nanometers, even more preferably 3 to 8 nanometers.

Oligonucleotide: As used herein, the terms "oligonucleotide" or "oligomer" refer to a nucleic acid sequence comprising 2 or more nucleotides, generally at least about 6 nucleotides to about 100,000 nucleotides, preferably about 6 to about 2000 nucleotides, and more preferably about 6 to about 300 nucleotides, even more preferably about 20 to about 300 nucleotides, and even more preferably about 20 to about 100 nucleotides. The terms "oligonucleotide" or "oligomer" also refer to a nucleic acid sequence comprising more than 100 to about 2000 nucleotides, preferably more than 100 to about 1000 nucleotides, and more preferably more than 100 to about 500 nucleotides. "Oligonucleotide" also generally refers to any polyribonucleotide or polydeoxribonucleotide, which may be unmodified RNA or DNA or modified RNA or DNA. "Oligonucleotide" includes, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "oligonucleotide" refers to triple-stranded regions comprising RNA or DNA or both RNA and DNA. Further, an oligonucleotide can be synthetic, genomic or recombinant, e.g., λ-DNA, cosmid DNA, artificial bacterial chromosome, yeast artificial chromosome and filamentous phage such as M13. In a very preferred embodiment of the present invention, the oligonucleotide is a synthetic oligonucleotide.

The term "oligonucleotide" also includes DNAs or RNAs containing one or more modified bases and DNAs or RNAs with backbones modified for stability or for other reasons. For example, suitable nucleotide modifications/analogs include peptide nucleic acid, inosin, tritylated bases, phosphorothioates, alkylphosphorothioates, 5-nitroindole deoxyribofuranosyl, 5-methyldeoxycytosine and 5,6-dihydro-5,6-dihydroxydeoxythymidine. A variety of modifications have been made to DNA and RNA; thus, "oligonucleotide" embraces chemically, enzymatically or metabolically modified forms of polynucleotides as typically found in nature, as well as the chemical forms of DNA and RNA characteristic of viruses and cells. Other nucleotide analogs/modifications will be evident to those skilled in the art.

Packaged: The term "packaged" as used herein refers to the state of an immunostimulatory substance, preferably of an immunostimulatory nucleic acid in relation to the VLP. The term "packaged" as used herein includes binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds such as thioether bonds, carbon-phosphorus bonds, and the like. The term also includes the enclosement, or partial enclosement, of a substance. The term "packaged" includes terms such as "coupled, "enclosed" and "attached." For example, the immunostimulatory substance such as the unmethylated CpG-containing oligonucleotide can be enclosed by the VLP without the existence of an actual binding, neither covalently nor non-covalently. In preferred embodiments, in particular, if immunostimulatory nucleic acids are the immunostimulatory substances, the term "packaged" indicates that the immunostimulatory nucleic acid in a packaged state is not accessible to DNAse or RNAse hydrolysis. In preferred embodiments, the immunostimulatory nucleic acid is packaged inside the VLP capsids, most preferably in a non-covalent manner.

The compositions of the invention can be combined, optionally, with a pharmaceutically-acceptable carrier. The term "pharmaceutically-acceptable carrier" as used herein means one or more compatible solid or liquid fillers, diluents or encapsulating substances which are suitable for administration into a human or other animal. The term "carrier" denotes an organic or inorganic ingredient, natural or synthetic, with which the active ingredient is combined to facilitate the application.

Organic molecule: As used herein, the term "organic molecule" refers to any chemical entity of natural or synthetic origin. In particular the term "organic molecule" as used herein encompasses, for example, any molecule being a member of the group of nucleotides, lipids, carbohydrates, polysaccharides, lipopolysaccharides, steroids, alkaloids, terpenes and fatty acids, being either of natural or synthetic origin. In particular, the term "organic molecule" encompasses molecules such as nicotine, cocaine, heroin or other pharmacologically active molecules contained in drugs of abuse. In general an organic molecule contains or is modified to contain a chemical functionality allowing its coupling, binding or other method of attachment to the virus-like particle in accordance with the invention.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, peptides, oligopeptides and proteins are included within the definition of polypeptide. This term is also intended to refer to post-expression modifications of the polypeptide, for example, glycosolations, acetylations, phosphorylations, and the like. A recombinant or derived polypeptide is not necessarily translated from a designated nucleic acid sequence. It may also be generated in any manner, including chemical synthesis.

A substance which "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a 51Cr release assay, typically and preferably as outlined in Current Protocols in Immunology, Editors: John E. Coligan et al.; John Wiley & Sons Inc., with and without the substance. The amount of the substance at which the CTL lytic activity is enhanced as compared to the CTL lytic activity without the substance is said to be an amount sufficient to enhance the immune response of the animal to the antigen. In a preferred embodiment, the immune response in enhanced by a factor of at least about 2, more preferably by a factor of about 3 or more. The amount of cytokines secreted may also be altered.

Effective Amount: As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Self antigen: As used herein, the tem "self antigen" refers to proteins encoded by the host's genome or DNA and products generated by proteins or RNA encoded by the host's genome or DNA are defined as self. Preferably, the tem "self antigen", as used herein, refers to proteins encoded by the human genome or DNA and products generated by proteins or RNA encoded by the human genome or DNA are defined as self. The inventive compositions, pharmaceutical compositions and vaccines comprising self antigens are in particular capable of breaking tolerance against a self antigen when applied to the host. In this context, "breaking tolerance against a self antigen" shall refer to enhancing an immune response, as defined herein, and preferably enhancing a B or a T cell response, specific for the self antigen when applying the inventive compositions, pharmaceutical compositions and vaccines comprising the self antigen to the host. In addition, proteins that result from a combination of two or several self-molecules or that represent a fraction of a self-molecule and proteins that have a high homology two self-molecules as defined above (>95%, preferably >97%, more preferably >99%) may also be considered self. In a further preferred embodiment of the present invention, the antigen is a self antigen. Very preferred embodiments of self-antigens useful for the present invention are described WO 02/056905, the disclosures of which are herewith incorporated by reference in its entirety.

Treatment: As used herein, the terms "treatment", "treat", "treated" or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse.

Vaccine: As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved, In this form, the composition of the present invention can be used conveniently to prevent, ameliorate, or otherwise treat a condition. Upon introduction into a host, the vaccine is able to provoke an immune response including, but not limited to, the production of antibodies, cytokines and/or the activation of cytotoxic T cells, antigen presenting cells, helper T cells, dendritic cells and/or other cellular responses.

Optionally, the vaccine of the present invention additionally includes an adjuvant which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include incomplete Freund's adjuvant, aluminum hydroxide and modified muramyldipeptide. The term "adjuvant" as used herein also refers to typically specific stimulators of the immune response which when combined with the vaccine of the present invention provide for an even more enhanced and typically specific immune response. Examples include, but limited to, GM-CSF, IL-2, IL-12, IFNα. Further examples are within the knowledge of the person skilled in the art.

Virus-like particle: As used herein, the term "virus-like particle" refers to a structure resembling a virus particle but which has not been demonstrated to be pathogenic. Typically, a virus-like particle in accordance with the invention does not carry genetic information encoding for the proteins of the virus-like particle. In general, virus-like particles lack the viral genome and, therefore, are noninfectious. Also, virus-like particles can often be produced in large quantities by heterologous expression and can be easily purified. Some virus-like particles may contain nucleic acid distinct from their genome. As indicated, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA phage coat protein: The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (SEQ ID: No 10) generated by expression of a Qβ CP gene containing, for example, a TAA stop codon precluding any expression of the longer A1 protein through suppression, see Kozlovska, T. M., et al., Intervirology 39: 9-15 (1996)), or additionally contain A1 protein subunits (SEQ ID: No 11) in the capsid assembly. The readthrough process has a low efficiency and is leading to an only very low amount of A1 protein in the VLPs. An extensive number of examples have been performed with different combinations of ISS packaged and antigen coupled. No differences in the coupling efficiency and the packaging have been observed when VLPs of Qβ coat protein assembled exclusively from Qβ CP subunits or VLPs of Qβ coat protein containing additionally A1 protein subunits in the capsids were used. Furthermore, no difference of the immune response between these QβVLP preparations was observed. Therefore, for the sake of clarity the term "QβVLP" is used throughout the description of the examples either for VLPs of Qβ coat protein assembled exclusively from Qβ CP subunits or VLPs of Qβ coat protein containing additionally A1 protein subunits in the capsids.

The term "virus particle" as used herein refers to the morphological form of a virus. In some virus types it comprises a genome surrounded by a protein capsid; others have additional structures (e.g., envelopes, tails, etc.).

Non-enveloped viral particles are made up of a proteinaceous capsid that surrounds and protects the viral genome. Enveloped viruses also have a capsid structure surrounding the genetic material of the virus but, in addition, have a lipid bilayer envelope that surrounds the capsid. In a preferred embodiment of the invention, the VLP's are free of a lipoprotein envelope or a lipoprotein-containing envelope. In a further preferred embodiment, the VLP's are free of an envelope altogether.

One, a, or an: When the terms "one," "a," or "an" are used in this disclosure, they mean "at least one" or "one or more," unless otherwise indicated.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and can be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, 2nd edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," Meth. Enzymol. 128, Academic Press San Diego (1990); Scopes, R. K., "Protein Purification Principles and Practice," 3rd ed., Springer-Verlag, New York (1994)) are also adequately described in the literature, all of which are incorporated herein by reference.

2. Compositions and Methods for Enhancing an Immune Response

The disclosed invention provides compositions and methods for enhancing an immune response against one or more antigens in an animal. Compositions of the invention comprise, or alternatively consist essentially of, or alternatively consist of, a virus-like particle and at least one immunostimulatory substance, wherein the immunostimulatory substance is bound to said virus-like particle, and wherein the immunostimulatory substance is an unmethylated CpG-containing oligonucleotide, wherein the CpG motif of said unmethylated CpG-containing oligonucleotide is part of a palindromic sequence, and wherein said palindromic sequence is flanked at its 3'-terminus and at its 5'-terminus by less than 10 guanosine entities. Furthermore, the invention conveniently enables the practitioner to construct such a composition for various treatment and/or prophylactic prevention purposes, which include the prevention and/or treatment of infectious diseases, as well as chronic infectious diseases, and the prevention and/or treatment of cancers, for example.

Virus-like particles in the context of the present application refer to structures resembling a virus particle but which are not pathogenic. In general, virus-like particles lack the viral genome and, therefore, are noninfectious. Also, virus-like particles can be produced in large quantities by heterologous expression and can be easily purified.

In a preferred embodiment, the virus-like particle is a recombinant virus-like particle. The skilled artisan can produce VLPs using recombinant DNA technology and virus coding sequences which are readily available to the public. For example, the coding sequence of a virus envelope or core protein can be engineered for expression in a baculovirus expression vector using a commercially available baculovirus vector, under the regulatory control of a virus promoter, with appropriate modifications of the sequence to allow functional linkage of the coding sequence to the regulatory sequence. The coding sequence of a virus envelope or core protein can also be engineered for expression in a bacterial expression vector, for example.

Examples of VLPs include, but are not limited to, the capsid proteins of Hepatitis B virus, measles virus, Sindbis virus, rotavirus, foot-and-mouth-disease virus, Norwalk virus, the retroviral GAG protein, the retrotransposon Ty protein p1, the surface protein of Hepatitis B virus, human papilloma virus, human polyoma virus, BK virus (BKV), RNA phages, Ty, fr-phage, GA-phage, AP 205-phage and, in particular, Qβ-phage.

As will be readily apparent to those skilled in the art, the VLP of the invention is not limited to any specific form. The particle can be synthesized chemically or through a biological process, which can be natural or non-natural. By way of example, this type of embodiment includes a virus-like particle or a recombinant form thereof.

In a more specific embodiment, the VLP can comprise, or alternatively consist of, recombinant polypeptides of Rotavirus; recombinant polypeptides of Norwalk virus; recombinant polypeptides of Alphavirus; recombinant proteins which form bacterial pili or pilus like structures; recombinant polypeptides of Foot and Mouth Disease virus; recombinant polypeptides of measles virus, recombinant polypeptides of Sindbis virus, recombinant polypeptides of Retrovirus; recombinant polypeptides of Hepatitis B virus (e.g., a HBcAg); recombinant polypeptides of Tobacco mosaic virus; recombinant polypeptides of Flock House Virus; recombinant polypeptides of human Papillomavirus; recombinant polypeptides of Polyoma virus and, in particular, recombinant polypeptides of human Polyoma virus, and in particular recombinant polypeptides of BK virus; recombinant polypeptides of bacteriophages, recombinant polypeptides of RNA phages; recombinant polypeptides of Ty; recombinant polypeptides of fr-phage, recombinant polypeptides of GA-phage, recombinant polypeptides of AP 205-phage and, in particular, recombinant polypeptides of Qβ-phage. The virus-like particle can further comprise, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild type counterparts.

In a preferred embodiment, the virus-like particle comprises, consists essentially of, or alternatively consists of recombinant proteins, or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; l) bacteriophage PP7; and m) bacteriophage AP205.

In another preferred embodiment of the present invention, the virus-like particle comprises, or alternatively consists essentially of, or alternatively consists of recombinant proteins, or fragments thereof, of the RNA-bacteriophage Qβ or of the RNA-bacteriophage fr or of the RNA-bacteriophage AP205.

In a further preferred embodiment of the present invention, the recombinant proteins comprise, or alternatively consist essentially of, or alternatively consist of coat proteins of RNA phages.

RNA-phage coat proteins forming capsids or VLPs, or fragments of the bacteriophage coat proteins compatible with self-assembly into a capsid or a VLP, are, therefore, further preferred embodiments of the present invention. Bacteriophage Qβ coat proteins, for example, can be expressed recombinantly in *E. coli*. Further, upon such expression these proteins spontaneously form capsids. Additionally, these capsids form a structure with an inherent repetitive organization.

Specific preferred examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein), bacteriophage R17 (PIR Accession No. VCBPR7), bacteriophage fr (SEQ ID NO:13; PIR Accession No. VCBPFR), bacteriophage GA (SEQ ID NO:14; GenBank Accession No. NP-040754), bacteriophage SP (GenBank Accession No. CAA30374 referring to SP CP and Accession No. NP_695026 referring to SP A1 protein), bacteriophage MS2 (PIR Accession No. VCBPM2), bacteriophage M11 (GenBank Accession No. AAC06250), bacteriophage MX1 (GenBank Accession No. AAC14699), bacteriophage NL95 (GenBank Accession No. AAC14704), bacteriophage f2 (GenBank Accession No. P03611), bacteriophage PP7 (SEQ ID NO: 22), and bacteriophage AP205 (SEQ ID NO: 31). Furthermore, the A1 protein of bacteriophage Qβ or C-terminal truncated forms missing as much as 100, 150 or 180 amino acids from its C-terminus may be incorporated in a capsid assembly of Qβ coat proteins. Generally, the percentage of QβA1 protein relative to Qβ CP in the capsid assembly will be limited, in order to ensure capsid formation. Further specific examples of bacteriophage coat proteins are described in WO 02/056905 on page 45 and 46 incorporated herein by reference. Further preferred virus-like particles of RNA-phages, in particular of Qβ in accordance of this invention are disclosed in WO 02/056905, the disclosure of which is herewith incorporated by reference in its entirety.

In a further preferred embodiment of the present invention, the virus-like particle comprises, or alternatively consists essentially of, or alternatively consists of recombinant proteins, or fragments thereof, of a RNA-phage, wherein the recombinant proteins comprise, consist essentially of or alternatively consist of mutant coat proteins of a RNA phage, preferably of mutant coat proteins of the RNA phages mentioned above. In another preferred embodiment, the mutant coat proteins of the RNA phage have been modified by removal of at least one lysine residue by way of substitution, or by addition of at least one lysine residue by way of substitution; alternatively, the mutant coat proteins of the RNA phage have been modified by deletion of at least one lysine residue, or by addition of at least one lysine residue by way of insertion. The deletion, substitution or addition of at least one lysine residue allows varying the degree of coupling, i.e. the amount of antigens per subunits of the VLP of the RNA-phages, in particular, to match and tailor the requirements of the vaccine. In a preferred embodiment of the present invention, on average at least 1.0 antigen peptide per subunit are linked to the VLP of the RNA-phage. This value is calculated as an average over all the subunits or monomers of the VLP of the RNA-phage. In a further preferred embodiment of the present invention, at least 1.1, 1.2, 1.3, 1.4, 1.5, 1.6, 1.7, 1.8, 1.9 or at least 2.0 antigen polypeptides are linked to the VLP of the RNA-phages as being calculated as a coupling average over all the subunits or monomers of the VLP of the RNA-phage.

In another preferred embodiment, the virus-like particle comprises, or alternatively consists essentially of, or alternatively consists of recombinant proteins, or fragments thereof, of the RNA-bacteriophage Qβ, wherein the recombinant proteins comprise, or alternatively consist essentially of, or alternatively consist of coat proteins having an amino acid sequence of SEQ ID NO:10, or a mixture of coat proteins having amino acid sequences of SEQ ID NO:10 and of SEQ ID NO: 11 or mutants of SEQ ID NO: 11 and wherein the N-terminal methionine is preferably cleaved.

In a further preferred embodiment of the present invention, the virus-like particle comprises, consists essentially of or alternatively consists of recombinant proteins of Qβ, or fragments thereof, wherein the recombinant proteins comprise, or alternatively consist essentially of, or alternatively consist of mutant Qβ coat proteins. In another preferred embodiment, these mutant coat proteins have been modified by removal of at least one lysine residue by way of substitution, or by addition of at least one lysine residue by way of substitution. Alternatively, these mutant coat proteins have been modified by deletion of at least one lysine residue, or by addition of at least one lysine residue by way of insertion.

Four lysine residues are exposed on the surface of the capsid of Qβ coat protein. Qβ mutants, for which exposed lysine residues are replaced by arginines can also be used for the present invention. The following Qβ coat protein mutants and mutant Qβ VLPs can, thus, be used in the practice of the invention: "Qβ-240" (Lys13-Arg; SEQ ID NO:20), "Qβ-243" (Asn 10-Lys; SEQ ID NO:21), "Qβ-250" (Lys 2-Arg, Lys13-Arg; SEQ ID NO:22), "Qβ-251" (SEQ ID NO:23) and "Qβ-259" (Lys 2-Arg, Lys16-Arg; SEQ ID NO:24). Thus, in further preferred embodiment of the present invention, the virus-like particle comprises, consists essentially of or alternatively consists of recombinant proteins of mutant Qβ coat proteins, which comprise proteins having an amino acid sequence selected from the group of a) the amino acid sequence of SEQ ID NO: 20; b) the amino acid sequence of SEQ ID NO:21; c) the amino acid sequence of SEQ ID NO: 22; d) the amino acid sequence of SEQ ID NO:23; and e) the amino acid sequence of SEQ ID NO: 24. The construction, expression and purification of the above indicated Qβ coat proteins, mutant Qβ coat protein VLPs and capsids, respectively, are disclosed in WO02/056905. In particular is hereby referred to Example 18 of above mentioned application.

In a further preferred embodiment of the present invention, the virus-like particle comprises, or alternatively consists essentially of, or alternatively consists of recombinant proteins of Qβ, or fragments thereof, wherein the recombinant proteins comprise, consist essentially of or alternatively consist of a mixture of either one of the foregoing Qβ mutants and the corresponding A1 protein.

In a further preferred embodiment of the present invention, the virus-like particle comprises, or alternatively essentially consists of, or alternatively consists of recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins, J., et al., J. Gen. Virol. 83: 1523-33 (2002)). AP205 coat protein can be expressed from plasmid pAP283-58 (SEQ ID NO: 30), which is a derivative of pQb10 (Kozlovska, T. M. et al., Gene 137:133-37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in WO 04/007538 which is incorporated by reference in its entirety. Vectors pQb10 and pQb185 are vectors derived from pGEM vector, and expression of the cloned genes in these vectors is controlled by the trp promoter (Kozlovska, T. M. et al., Gene 137:133-37 (1993)). Plasmid pAP283-58 (SEQ ID NO:30) comprises a putative AP205 ribosomal binding site in the following sequence, which is downstream of the XbaI site, and immediately upstream of the ATG start codon of the AP205 coat protein: tctagaATTTTCTGCGCACCCAT CCCGGGTGGCGC-CCAAAGT GAGGAAA ATCACatg (bases 77-133 of SEQ ID NO: 30). The vector pQb185 comprises a Shine Delagarno sequence downstream from the XbaI site and upstream of the start codon (tctagaTTAACCCAACGCGT AGGAGTCAGGCCatg (SEQ ID NO: 46), Shine Delagarno sequence underlined).

In a further preferred embodiment of the present invention, the virus-like particle comprises, or alternatively essentially consists of, or alternatively consists of recombinant coat proteins, or fragments thereof, of the RNA-phage AP205.

This preferred embodiment of the present invention, thus, comprises AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 31) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In a further preferred embodiment of the present invention, the virus-like particle comprises, or alternatively essentially consists of, or alternatively consists of recombinant mutant coat proteins, or fragments thereof, of the RNA-phage AP205.

Assembly-competent mutant forms of AP205 VLPs, including AP205 coat protein with the subsitution of proline at amino acid 5 to threonine (SEQ ID NO: 32), may also be used in the practice of the invention and leads to a further preferred embodiment of the invention. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID No. 33), which is derived directly from pQb185, and which contains the mutant AP205 coat protein gene instead of the Qβ coat protein gene. Vectors for expression of the AP205 coat protein are transfected into E. coli for expression of the AP205 coat protein.

Methods for expression of the coat protein and the mutant coat protein, respectively, leading to self-assembly into VLPs are described in WO 04/007538 which is incorporated by reference in its entirety. Suitable E. coli strains include, but are not limited to, E. coli K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., Gene 137:133-37 (1993)).

AP205 coat proteins expressed from the vectors pAP283-58 and pAP281-32 may be devoid of the initial Methionine amino-acid, due to processing in the cytoplasm of E. coli. Cleaved, uncleaved forms of AP205 VLP, or mixtures thereof are further preferred embodiments of the invention.

In a further preferred embodiment of the present invention, the virus-like particle comprises, or alternatively essentially consists of, or alternatively consists of a mixture of recombinant coat proteins, or fragments thereof, of the RNA-phage AP205 and of recombinant mutant coat proteins, or fragments thereof, of the RNA-phage AP205.

In a further preferred embodiment of the present invention, the virus-like particle comprises, or alternatively essentially consists of, or alternatively consists of fragments of recombinant coat proteins or recombinant mutant coat proteins of the RNA-phage AP205.

Recombinant AP205 coat protein fragments capable of assembling into a VLP and a capsid, respectively are also useful in the practice of the invention. These fragments may be generated by deletion, either internally or at the termini of the coat protein and mutant coat protein, respectively. Insertions in the coat protein and mutant coat protein sequence or fusions of antigen sequences to the coat protein and mutant coat protein sequence, and compatible with assembly into a VLP, are further embodiments of the invention and lead to chimeric AP205 coat proteins, and particles, respectively. The outcome of insertions, deletions and fusions to the coat protein sequence and whether it is compatible with assembly into a VLP can be determined by electron microscopy.

The particles formed by the AP205 coat protein, coat protein fragments and chimeric coat proteins described above, can be isolated in pure form by a combination of fractionation steps by precipitation and of purification steps by gel filtration using e.g. Sepharose CL-4B, Sepharose CL-2B, Sepharose CL-6B columns and combinations thereof as described in WO 04/007538 which is incorporated by reference in its entirety. Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety.

The crystal structure of several RNA bacteriophages has been determined (Golmohammadi, R. et al., Structure 4:543-554 (1996)). Using such information, one skilled in the art could readily identify surface exposed residues and modify bacteriophage coat proteins such that one or more reactive amino acid residues can be inserted. Thus, one skilled in the art could readily generate and identify modified forms of bacteriophage coat proteins which can be used in the practice of the invention. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2) can also be used for the inventive compositions and vaccine compositions. Further possible examples of modified RNA bacteriophages as well as variants of proteins and N- and C terminal truncation mutants which form capsids or capsid like structures, as well as methods for preparing such compositions and vaccine compositions, respectively, which are suitable for use in the present invention are described in WO 02/056905 on page 50, line 33 to page 52, line 29.

The invention thus includes compositions and vaccine compositions prepared from proteins which form capsids or VLPs, methods for preparing these compositions from individual protein subunits and VLPs or capsids, methods for preparing these individual protein subunits, nucleic acid molecules which encode these subunits, and methods for vaccinating and/or eliciting immunological responses in individuals using these compositions of the present invention.

In another preferred embodiment of the invention, the VLP's are free of a lipoprotein envelope or a lipoprotein-containing envelope. In a further preferred embodiment, the VLP's are free of an envelope altogether.

The lack of a lipoprotein envelope or lipoprotein-containing envelope and, in particular, the complete lack of an envelope leads to a more defined virus-like particle in its structure and composition. Such more defined virus-like particles, therefore, may minimize side-effects. Moreover, the lack of a lipoprotein-containing envelope or, in particular, the complete lack of an envelope avoids or minimizes incorporation of potentially toxic molecules and pyrogens within the virus-like particle.

In one embodiment, the invention provides a vaccine composition of the invention comprising a virus-like particle, wherein preferably said virus-like particle is a recombinant virus-like particle. Preferably, the virus-like particle comprises, or alternatively consist essentially of, or alternatively consists of, recombinant proteins, or fragments thereof, of a RNA-phage, preferably of coat proteins of RNA phages. Alternatively, the recombinant proteins of the virus-like particle of the vaccine composition of the invention comprise, or alternatively consist essentially of, or alternatively consist of mutant coat proteins of RNA phages, wherein the RNA-phage is selected from the group consisting of: (a) bacteriophage Qβ; (b) bacteriophage R17; (c) bacteriophage fr; (d) bacteriophage GA; (e) bacteriophage SP; (f) bacteriophage MS2; (g) bacteriophage M11; (h) bacteriophage Mx1; (i) bacteriophage NL95; (k) bacteriophage f2; (l) bacteriophage PP7; and (m) bacteriophage AP205.

In a preferred embodiment, the mutant coat proteins of said RNA phage have been modified by removal, or by addition of at least one lysine residue by way of substitution. In another preferred embodiment, the mutant coat proteins of said RNA phage have been modified by deletion of at least one lysine residue or by addition of at least one lysine residue by way of insertion. In a preferred embodiment, the virus-like particle comprises recombinant proteins or fragments thereof, of RNA-phage Qβ or alternatively of RNA-phage fr, or of RNA-phage AP205.

As previously stated, the invention includes virus-like particles or recombinant forms thereof. Skilled artisans have the knowledge to produce such particles and attach antigens thereto. Further preferred embodiments of the present invention hereto are disclosed in the Example Section.

In one embodiment, the virus-like particle comprises, or alternatively consists essentially of, or alternatively consists of recombinant proteins, or fragments thereof, of the BK virus (BKV), wherein the recombinant proteins comprise, or alternatively consist essentially of, or alternatively consist of proteins having an amino acid sequence of SEQ ID NO:12. BK virus (BKV) is a non-enveloped double stranded DNA virus belonging to the polyoma virus subfamily of the papovaviridae. VP1 is the major capsid protein of BKV. VP1 has 362 amino acids (SEQ ID NO: 12, Gene Bank entry: AAA46882) and is 42 kDa in size. When produced in *E. coli*, insect cells or yeast VP1 spontaneously forms capsid structures (Salunke D. M., et al., Cell 46(6):895-904 (1986); Sasnauskas, K., et al., Biol. Chem. 380(3):381-6 (1999); Sasnauskas, K., et al., 3rd International Workshop "Virus-like particles as vaccines" Berlin, Sep. 26-29 (2001); Touze, A., et al., J Gen Virol. 82(Pt 12):3005-9 (2001). The capsid is organized in 72 VP1 pentamers forming an icosahedral structure. The capsids have a diameter of approximately 45 nm.

In one embodiment, the particles used in compositions of the invention are composed of a Hepatitis B capsid (core) protein (HBcAg) or a fragment of a HBcAg which has been modified to either eliminate or reduce the number of free cysteine residues. Zhou et al. (J. Virol. 66:5393 5398 (1992)) demonstrated that HBcAgs which have been modified to remove the naturally resident cysteine residues retain the ability to associate and form multimeric structures. Thus, core particles suitable for use in compositions of the invention include those comprising modified HBcAgs, or fragments thereof, in which one or more of the naturally resident cysteine residues have been either deleted or substituted with another amino acid residue (e.g., a serine residue).

The HBcAg is a protein generated by the processing of a Hepatitis B core antigen precursor protein. A number of isotypes of the HBcAg have been identified and their amino acids sequences are readily available to those skilled in the art. For example, the HBcAg protein having the amino acid sequence shown in SEQ ID NO: 16 is 185 amino acids in length and is generated by the processing of a 212 amino acid Hepatitis B core antigen precursor protein. This processing results in the removal of 29 amino acids from the N terminus of the Hepatitis B core antigen precursor protein. Similarly, the HBcAg protein that is 185 amino acids in length is generated by the processing of a 214 amino acid Hepatitis B core antigen precursor protein.

In preferred embodiments, vaccine compositions of the invention will be prepared using the processed form of a HBcAg (i.e., a HBcAg from which the N terminal leader sequence of the Hepatitis B core antigen precursor protein have been removed).

Further, when HBcAgs are produced under conditions where processing will not occur, the HBcAgs will generally be expressed in "processed" form. For example, bacterial systems, such as *E. coli*, generally do not remove the leader sequences, also referred to as "signal peptides," of proteins which are normally expressed in eukaryotic cells. Thus, when an *E. coli* expression system directing expression of the protein to the cytoplasm is used to produce HBcAgs of the invention, these proteins will generally be expressed such that the N terminal leader sequence of the Hepatitis B core antigen precursor protein is not present.

The preparation of Hepatitis B virus-like particles, which can be used for the present invention, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in WO 02/056905. For the latter application, it is in particular referred to Example 23, 24, 31 and 51. All three documents are explicitly incorporated herein by reference.

The present invention also includes HBcAg variants which have been modified to delete or substitute one or more additional cysteine residues. Thus, the vaccine compositions of the invention include compositions comprising HBcAgs in which cysteine residues not present in the amino acid sequence shown in SEQ ID NO: 16 have been deleted.

It is well known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached would be reduced in number or eliminated altogether.

A number of naturally occurring HBcAg variants suitable for use in the practice of the present invention have been identified. Yuan et al., (J. Virol. 73:10122 10128 (1999)), for example, describe variants in which the isoleucine residue at position corresponding to position 97 in SEQ ID NO:25 is replaced with either a leucine residue or a phenylalanine residue. The amino acid sequences of a number of HBcAg variants, as well as several Hepatitis B core antigen precursor variants, are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X85299, X85307, X65257, X85311, X85301 (SEQ ID NO:26), X85314, X85287, X85272, X85319, AB010289, X85285, AB010289, AF121242, M90520 (SEQ ID NO:27), P03153, AF110999, and M95589, the disclosures of each of which are incorporated herein by reference. The sequences of the hereinabove mentioned Hepatitis B core antigen precursor variants are further disclosed in WO 01/85208 in SEQ ID NOs: 89-138 of the application WO 01/85208. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO: 28. Further HBcAg variants suitable for use in the compositions of the invention, and which may be further modified according to the disclosure of this specification are described in WO 01/98333, WO 00/177158 and WO 00/214478.

HBcAgs suitable for use in the present invention can be derived from any organism so long as they are able to enclose or to be coupled or otherwise attached to, in particular as long as they are capable of packaging, an unmethylated CpG-containing oligonucleotide and induce an immune response.

As noted above, generally processed HBcAgs (i.e., those which lack leader sequences) will be used in the vaccine compositions of the invention. The present invention includes vaccine compositions, as well as methods for using these compositions, which employ the above described variant HBcAgs.

Further included within the scope of the invention are additional HBcAg variants which are capable of associating to form dimeric or multimeric structures. Thus, the invention further includes vaccine compositions comprising HBcAg polypeptides comprising, or alternatively consisting of, amino acid sequences which are at least 80%, 85%, 90%, 95%, 97% or 99% identical to any of the wild-type amino acid sequences, and forms of these proteins which have been processed, where appropriate, to remove the N terminal leader sequence.

Whether the amino acid sequence of a polypeptide has an amino acid sequence that is at least 80%, 85%, 90%, 95%, 97% or 99% identical to one of the wild-type amino acid sequences, or a subportion thereof, can be determined conventionally using known computer programs such the Bestfit program. When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed.

The amino acid sequences of the hereinabove mentioned HBcAg variants and precursors are relatively similar to each other. Thus, reference to an amino acid residue of a HBcAg variant located at a position which corresponds to a particular position in SEQ ID NO:28, refers to the amino acid residue which is present at that position in the amino acid sequence shown in SEQ ID NO:28. The homology between these HBcAg variants is for the most part high enough among Hepatitis B viruses that infect mammals so that one skilled in the art would have little difficulty reviewing both the amino acid sequence shown in SEQ ID NO:28 and in SEQ ID NO: 16, respectively, and that of a particular HBcAg variant and identifying "corresponding" amino acid residues. Furthermore, the HBcAg amino acid sequence shown in SEQ ID NO:27, which shows the amino acid sequence of a HBcAg derived from a virus which infect woodchucks, has enough homology to the HBcAg having the amino acid sequence shown in SEQ ID NO:28 that it is readily apparent that a three amino acid residue insert is present in SEQ ID NO:27 between amino acid residues 155 and 156 of SEQ ID NO:28.

The invention also includes vaccine compositions which comprise HBcAg variants of Hepatitis B viruses which infect birds, as wells as vaccine compositions which comprise fragments of these HBcAg variants. As one skilled in the art would recognize, one, two, three or more of the cysteine residues naturally present in these polypeptides could be either substituted with another amino acid residue or deleted prior to their inclusion in vaccine compositions of the invention.

As discussed above, the elimination of free cysteine residues reduces the number of sites where toxic components can bind to the HBcAg, and also eliminates sites where cross linking of lysine and cysteine residues of the same or of neighboring HBcAg molecules can occur. Therefore, in another embodiment of the present invention, one or more cysteine residues of the Hepatitis B virus capsid protein have been either deleted or substituted with another amino acid residue. Expression and purification of an HBcAg-Lys variant has been described in Example 24 of WO 02/056905 and the construction of a HBcAg devoid of free cysteine residues and containing an inserted lysine residue has been described in Example 31 of WO 02/056905.

In other embodiments, compositions and vaccine compositions, respectively, of the invention will contain HBcAgs from which the C terminal region (e.g., amino acid residues 145 185 or 150 185 of SEQ ID NO: 28) has been removed. Thus, additional modified HBcAgs suitable for use in the practice of the present invention include C terminal truncation mutants. Suitable truncation mutants include HBcAgs where 1, 5, 10, 15, 20, 25, 30, 34, 35, amino acids have been removed from the C terminus.

HBcAgs suitable for use in the practice of the present invention also include N terminal truncation mutants. Suitable truncation mutants include modified HBcAgs where 1, 2, 5, 7, 9, 10, 12, 14, 15, or 17 amino acids have been removed from the N terminus.

Further HBcAgs suitable for use in the practice of the present invention include N and C terminal truncation mutants. Suitable truncation mutants include HBcAgs where 1, 2, 5, 7, 9, 10, 12, 14, 15, and 17 amino acids have been removed from the N terminus and 1, 5, 10, 15, 20, 25, 30, 34, 35 amino acids have been removed from the C terminus.

The invention further includes compositions and vaccine compositions, respectively, comprising HBcAg polypeptides comprising, or alternatively essentially consisting of, or alternatively consisting of, amino acid sequences which are at least 80%, 85%, 90%, 95%, 97%, or 99% identical to the above described truncation mutants.

In certain embodiments of the invention, a lysine residue is introduced into a HBcAg polypeptide, to mediate the binding of the antigen or antigenic determinant to the VLP of HBcAg. In preferred embodiments, compositions of the invention are prepared using a HBcAg comprising, or alternatively consisting of, amino acids 1-144, or 1-149, 1-185 of SEQ ID NO:28, which is modified so that the amino acids corresponding to positions 79 and 80 are replaced with a peptide having the amino acid sequence of Gly-Gly-Lys-Gly-Gly (SEQ ID NO: 18) resulting in the HBcAg polypeptide having the sequence shown in SEQ ID NO:29). These compositions are particularly useful in those embodiments where an antigenic determinant is coupled to a VLP of HBcAg. In further preferred embodiments, the cysteine residues at positions 48 and 107 of SEQ ID NO:28 are mutated to serine. The invention further includes compositions comprising the corresponding polypeptides having amino acid sequences shown in any of the hereinabove mentioned Hepatitis B core antigen precursor variants which also have above noted amino acid alterations. Further included within the scope of the invention are additional HBcAg variants which are capable of associating to form a capsid or VLP and have the above noted amino acid alterations. Thus, the invention further includes compositions and vaccine compositions, respectively, comprising HBcAg polypeptides which comprise, or alternatively consist of, amino acid sequences which are at least 80%, 85%, 90%, 95%, 97% or 99% identical to any of the wild-type amino acid sequences, and forms of these proteins which have been processed, where appropriate, to remove the N terminal leader sequence and modified with above noted alterations.

Compositions or vaccine compositions of the invention may comprise mixtures of different HBcAgs. Thus, these vaccine compositions may be composed of HBcAgs which differ in amino acid sequence. For example, vaccine compositions could be prepared comprising a "wild type" HBcAg and a modified HBcAg in which one or more amino acid residues have been altered (e.g., deleted, inserted or substituted). Further, preferred vaccine compositions of the invention are those which present highly ordered and repetitive antigen arrays.

As previously disclosed, the invention is based on the surprising finding that immunostimulatory substances, and herein in particular specific DNA-oligonucleotides containing CpG motifs, can be packaged into VLPs. Unexpectedly, the nucleic acids present in VLPs can be replaced specifically by the specific DNA-oligonucleotides containing CpG motifs. As an example, the specific CpG-VLPs are more immunogenic and elicit more specific effects than their CpG-free counterparts and induce enhanced B and T cell responses. The immune response against antigens coupled, fused or attached otherwise to the VLPs is similarly enhanced as the immune response against the VLP itself. In addition, the T cell responses against both the VLPs and antigens are especially directed to the Th1 type. Furthermore, the packaged nucleic acids and CpGs, respectively, are protected from degradation, i.e., they are more stable. Moreover, non-specific activation of cells from the innate immune system is dramatically reduced.

The innate immune system has the capacity to recognize invariant molecular pattern shared by microbial pathogens. Recent studies have revealed that this recognition is a crucial step in inducing effective immune responses. The main mechanism by which microbial products augment immune responses is to stimulate APC, expecially dendritic cells to produce proinflammatory cytokines and to express high levels costimulatory molecules for T cells. These activated dendritic cells subsequently initiate primary T cell responses and dictate the type of T cell-mediated effector function.

Two classes of nucleic acids, namely 1) bacterial DNA that contains immunostimulatory sequences, in particular unmethylated CpG dinucleotides within specific flanking bases (referred to as CpG motifs) and 2) double-stranded RNA synthesized by various types of viruses represent important members of the microbial components that enhance immune responses. Synthetic double stranded (ds) RNA such as polyinosinic-polycytidylic acid (poly I:C) are capable of inducing dendritic cells to produce proinflammatory cytokines and to express high levels of costimulatory molecules.

A series of studies by Tokunaga and Yamamoto et al. has shown that bacterial DNA or synthetic oligodeoxynucleotides induce human PBMC and mouse spleen cells to produce type I interferon (IFN) (reviewed in Yamamoto et al., Springer Semin Immunopathol. 22:11-19). Poly (I:C) was originally synthesized as a potent inducer of type I IFN but also induces other cytokines such as IL-12.

Preferred ribonucleic acid encompass polyinosinic-polycytidylic acid double-stranded RNA (poly I:C). Ribonucleic acids and modifications thereof as well as methods for their production have been described by Levy, H. B (Methods Enzymol. 1981, 78:242-251), DeClercq, E (Methods Enzymol. 1981, 78:227-236) and Torrence, P. F. (Methods Enzymol 1981; 78:326-331) and references therein. Further preferred ribonucleic acids comprise polynucleotides of inosinic acid and cytidiylic acid such poly (IC) of which two strands forms double stranded RNA. Ribonucleic acids can be isolated from organisms. Ribonucleic acids also encompass further synthetic ribonucleic acids, in particular synthetic poly (I:C) oligonucleotides that have been rendered nuclease resistant by modification of the phosphodiester backbone, in particular by phosphorothioate modifications. In a further embodiment the ribose backbone of poly (I:C) is replaced by a deoxyribose. Those skilled in the art know procedures how to synthesize synthetic oligonucleotides.

In another preferred embodiment of the invention molecules that active toll-like receptors (TLR) are enclosed. Ten human toll-like receptors are known uptodate. They are activated by a variety of ligands. TLR2 is activated by peptidoglycans, lipoproteins, lipopolysacchrides, lipoteichonic acid and Zymosan, and macrophage-activating lipopeptide MALP-2; TLR3 is activated by double-stranded RNA such as poly (I:C); TLR4 is activated by lipopolysaccharide, lipoteichoic acids and taxol and heat-shock proteins such as heat shock protein HSP-60 and Gp96; TLR5 is activated by bacterial flagella, especially the flagellin protein; TLR6 is activated by peptidoglycans, TLR7 is activated by imiquimoid and imidazoquinoline compounds, such as R-848, loxoribine and bropirimine and TLR9 is activated by bacterial DNA, in particular CpG DNA. Ligands for TLR1, TLR8 and TLR10 are not known so far. However, recent reports indicate that same receptors can react with different ligands and that further receptors are present. The above list of ligands is not exhaustive and further ligands are within the knowledge of the person skilled in the art.

Preferably, the immunostimulatory substance of the present invention is an unmethylated CpG-containing oligonucleotide, wherein the CpG motif of the unmethylated CpG-containing oligonucleotide is part of a palindromic sequence, and wherein the palindromic sequence is flanked at its 3'-terminus and at its 5'-terminus by less than 10 guanosine entities. In addition, the oligonucleotide preferably comprises about 10 to about 30 nucleotides. In a preferred embodiment, the CpG-containing oligonucleotide contains one or more phosphorothioate modifications of the phosphate backbone. For example, a CpG-containing oligonucleotide having one or more phosphate backbone modifications or having all of the phosphate backbone modified and a CpG-containing oligonucleotide wherein one, some or all of the nucleotide phosphate backbone modifications are phosphorothioate modifications are included within the scope of the present invention.

The CpG-containing oligonucleotide can also be recombinant, genomic, synthetic, cDNA, plasmid-derived and single or double stranded. For use in the instant invention, the nucleic acids can be synthesized de novo using any of a number of procedures well known in the art. For example, the b-cyanoethyl phosphoramidite method (Beaucage, S. L., and Caruthers, M. H., Tet. Let. 22:1859 (1981); nucleoside H-phosphonate method (Garegg et al., Tet. Let. 27:4051-4054 (1986); Froehler et al., Nucl. Acid. Res. 14:5399-5407 (1986); Garegg et al., Tet. Let. 27:4055-4058 (1986), Gaffney et al., Tet. Let. 29:2619-2622 (1988)). These chemistries can be performed by a variety of automated oligonucleotide synthesizers available in the market. Alternatively, CpGs can be produced on a large scale in plasmids, (see Sambrook, T., et al., "Molecular Cloning: A Laboratory Manual," Cold Spring Harbor laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases.

The unmethylated CpG-containing oligonucleotide of the invention can be bound to the VLP by any way known in the art provided the composition enhances an immune response in an animal. For example, the oligonucleotide can be bound either covalently or non-covalently. In addition, the VLP can enclose, fully or partially, the unmethylated CpG-containing oligonucleotide. Preferably, the unmethylated CpG-containing oligonucleotide can be bound to a VLP site such as an oligonucleotide binding site (either naturally or non-naturally occurring), a DNA binding site or a RNA binding site. In another embodiment, the VLP site comprises an arginine-rich repeat or a lysine-rich repeat.

One specific use for the compositions of the invention is to activate dendritic cells for the purpose of enhancing a specific immune response against antigens. The immune response can be enhanced using ex vivo or in vivo techniques. The ex vivo procedure can be used on autologous or heterologous cells, but is preferably used on autologous cells. In preferred embodiments, the dendritic cells are isolated from peripheral blood or bone marrow, but can be isolated from any source of dendritic cells. Ex vivo manipulation of dendritic cells for the purposes of cancer immunotherapy have been described in several references in the art, including Engleman, E. G., Cytotechnology 25:1 (1997); Van Schooten, W., et al., Molecular Medicine Today, June, 255 (1997); Steinman, R. M., Experimental Hematology 24:849 (1996); and Gluckman, J. C., Cytokines, Cellular and Molecular Therapy 3:187 (1997).

The dendritic cells can also be contacted with the inventive compositions using in vivo methods. In order to accomplish this, the CpGs are administered in combination with the VLP optionally coupled, fused or otherwise attached to an antigen directly to a subject in need of immunotherapy. In some embodiments, it is preferred that the VLPs/CpGs be administered in the local region of the tumor, which can be accomplished in any way known in the art, e.g., direct injection into the tumor.

A further aspect of the present invention and a preferred embodiment of the present invention is to provide a composition, typically and preferably for enhancing an immune response in an animal, comprising (a) a virus-like particle; (b) an immunostimulatory substance; and (c) at least one antigen or antigenic determinant; wherein said antigen is bound to said virus-like particle; and wherein said immunostimulatory substance is bound to said virus-like particle, and wherein said immunostimulatory substance is an unmethylated CpG-containing oligonucleotide, wherein the CpG motif of said unmethylated CpG-containing oligonucleotide is part of a palindromic sequence, wherein said palindromic sequence is GACGATCGTC (SEQ ID NO: 1), and wherein said palindromic sequence is flanked at its 3'-terminus and at its 5'-terminus by less than 10 guanosine entities.

We found that the inventive immunostimulatory substances, i.e. the unmethylated CpG-containing oligonucleotides, wherein the CpG motif of said unmethylated CpG-containing oligonucleotides are part of a palindromic sequence, wherein the palindromic sequence is GACGATCGTC (SEQ ID NO: 1), and wherein the palindromic sequence is flanked at its 3'-terminus and at its 5'-terminus by less than 10 guanosine entities, are effective at stimulating immune cells in vitro. Moreover, these inventive immunostimulatory substances have unexpectedly found to be very efficiently packaged into VLPs. The packaging ability was hereby enhanced as compared to the corresponding immunostimulatory substance having the sequence GACGATCGTC (SEQ ID NO: 1) flanked by 10 guanosine entitites at the 5' and 3' terminus. The latter was previously found to be able to stimulate blood cells in vitro (Kuramoto E. et al., Japanese Journal Cancer Research 83, 1128-1131 (1992).

In a preferred embodiment of the present invention, the palindromic sequence comprises, or alternatively consist essentially of, or alternatively consists of or is GACGATCGTC (SEQ ID NO: 1), wherein said palindromic sequence is flanked at its 5'-terminus by at least 3 and at most 9 guanosine entities and wherein said palindromic sequence is flanked at its 3'-terminus by at least 6 and at most 9 guanosine entities.

In a further very preferred embodiment of the present invention, the immunostimulatory substance is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) GGGGACGATCGTCGGGGGG ((SEQ ID NO: 2); and typically abbreviated herein as G3-6), (b) GGGGGACGATCGTCGGGGGG ((SEQ ID NO: 3); and typically abbreviated herein as G4-6), (c) GGGGGGACGATCGTCGGGGGG ((SEQ ID NO: 4); and typically abbreviated herein as G5-6), (d) GGGGGGGACGATCGTCGGGGGG ((SEQ ID NO: 5); and typically abbreviated herein as G6-6), (e) GGGGGGGGACGATCGTCGGGGGGG ((SEQ ID NO: 6); and typically abbreviated herein as G7-7), (f) GGGGGGGGGACGATCGTCGGGGGGGG ((SEQ ID NO: 7); and typically abbreviated herein as G8-8), (g) GGGGGGGGGGACGATCGTCGGGGGGGGG ((SEQ ID NO: 8); and typically abbreviated herein as G9-9), and (h) GGGGGGCGACGACGATCGTCGTCGGGGGGG ((SEQ ID NO: 9); and typically abbreviated herein as G6).

In a further preferred embodiment of the present invention the immunostimulatory substance is an unmethylated CpG-containing oligonucleotide, wherein the CpG motif of said unmethylated CpG-containing oligonucleotide is part of a palindromic sequence, wherein said palindromic sequence is GACGATCGTC (SEQ ID NO: 1), and wherein said palindromic sequence is flanked at its 5'-terminus by at least 4 and at most 9 guanosine entities and wherein said palindromic sequence is flanked at its 3'-terminus by at least 6 and at most 9 guanosine entities.

In another preferred embodiment of the present invention the immunostimulatory substance is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) GGGGGACGATCGTCGGGGGG ((SEQ ID NO: 3); and typically abbreviated herein as G4-6), (b) GGGGG-GACGATCGTCGGGGGG ((SEQ ID NO: 4); and typically abbreviated herein as G5-6), (c) GGGGGGGAC-GATCGTCGGGGGG ((SEQ ID NO: 5); and typically abbreviated herein as G6-6), (d) GGGGGGGAC-GATCGTCGGGGGGG ((SEQ ID NO: 6); and typically abbreviated herein as G7-7), (e) GGGGGGGGAC-GATCGTCGGGGGGGG ((SEQ ID NO: 7); and typically abbreviated herein as G8-8), (f) GGGGGGGGGAC-GATCGTCGGGGGGGGG ((SEQ ID NO: 8); and typically abbreviated herein as G9-9).

In a further preferred embodiment of the present invention the immunostimulatory substance is an unmethylated CpG-containing oligonucleotide, wherein the CpG motif of said unmethylated CpG-containing oligonucleotide is part of a palindromic sequence, wherein said palindromic sequence is GACGATCGTC (SEQ ID NO: 1), and wherein said palindromic sequence is flanked at its 5'-terminus by at least 5 and at most 8 guanosine entities and wherein said palindromic sequence is flanked at its 3'-terminus by at least 6 and at most 8 guanosine entities.

The experimental data show that the ease of packaging of the preferred inventive immunostimulatory substances, i.e. the guanosine flanked, palindromic and unmethylated CpG-containing oligonucleotides, wherein the palindromic sequence is GACGATCGTC (SEQ ID NO: 1), and wherein the palindromic sequence is flanked at its 3'-terminus and at its 5'-terminus by less than 10 guanosine entities, into VLP's increases if the palindromic sequences are flanked by fewer guanosine entities. However, decreasing the number of guanosine entities flanking the palindromic sequences leads to a decrease of stimulating blood cells in vitro. Thus, packagability is paid by decreased biological activity of the indicated inventive immunostimulatory substances. The present preferred embodiments represent, thus, a compromise between packagability and biological activity.

In another preferred embodiment of the present invention the immunostimulatory substance is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) GGGGGGACGATCGTCGGGGGG ((SEQ ID NO: 4); and typically abbreviated herein as G5-6), (b) GGGGGG-GACGATCGTCGGGGGG ((SEQ ID NO: 5); and typically abbreviated herein as G6-6), (c) GGGGGGGAC-GATCGTCGGGGGGG ((SEQ ID NO: 6); and typically abbreviated herein as G7-7), (d) GGGGGGGGAC-GATCGTCGGGGGGGG ((SEQ ID NO: 7); and typically abbreviated herein as G8-8).

In a very preferred embodiment of the present invention the immunostimulatory substance is an unmethylated CpG-containing oligonucleotide, wherein the CpG motif of said unmethylated CpG-containing oligonucleotide is part of a palindromic sequence, wherein said unmethylated has the nucleic acid sequence of SEQ ID NO: 7, i.e. the immunostimulatory substance is G8-8.

As mentioned above, the optimal sequence used to package into VLPs is a compromise between packagability and biological activity. Taking this into consideration, the G8-8 immunostimulatoy substance is a very preferred embodiment of the present invention since it is biologically highly active while it still reasonably well packaged.

The inventive composition can further comprise an antigen or antigenic determinant bound to the virus-like particle. The invention provides for compositions that vary according to the antigen or antigenic determinant selected in consideration of the desired therapeutic effect. Very preferred antigens or antigenic determinants suitable for use in the present invention are disclosed in WO 00/32227, in WO 01/85208 and in WO 02/056905, the disclosures of which are herewith incorporated by reference in their entireties.

The antigen can be any antigen of known or yet unknown provenance. It can be isolated from bacteria, viruses or other pathogens or can be a recombinant antigen obtained from expression of suitable nucleic acid coding therefor. It can also be isolated from prions, tumors, self-molecules, non-peptidic hapten molecules, allergens and hormones. In a preferred embodiment, the antigen is a recombinant antigen. The selection of the antigen is, of course, dependent upon the immunological response desired and the host.

In one embodiment of the immune enhancing composition of the present invention, the immune response is induced against the VLP itself. In another embodiment of the invention a virus-like particle is coupled, fused or otherwise attached to an antigen/immunogen against which an enhanced immune response is desired.

In a further preferred embodiment of the invention, the at least one antigen or antigenic determinant is fused to the virus-like particle. As outlined above, a VLP is typically composed of at least one subunit assembling into a VLP. Thus, in again a further preferred embodiment of the invention, the antigen or antigenic determinant is fused to at least one subunit of the virus-like particle or of a protein capable of being incorporated into a VLP generating a chimeric VLP-subunit-antigen fusion.

Fusion of the antigen or antigenic determinant can be effected by insertion into the VLP subunit sequence, or by fusion to either the N- or C-terminus of the VLP-subunit or protein capable of being incorporated into a VLP. Hereinafter, when referring to fusion proteins of a peptide to a VLP subunit, the fusion to either ends of the subunit sequence or internal insertion of the peptide within the subunit sequence are encompassed.

Fusion may also be effected by inserting antigen or antigenic determinant sequences into a variant of a VLP subunit where part of the subunit sequence has been deleted, that are further referred to as truncation mutants. Truncation mutants may have N- or C-terminal, or internal deletions of part of the sequence of the VLP subunit. For example, the specific VLP HBcAg with, for example, deletion of amino acid residues 79 to 81 is a truncation mutant with an internal deletion. Fusion of antigens or antigenic determinants to either the N- or C-terminus of the truncation mutants VLP-subunits also lead to embodiments of the invention. Likewise, fusion of an epitope into the sequence of the VLP subunit may also be effected by substitution, where for example for the specific VLP HBcAg, amino acids 79-81 are replaced with a foreign epitope. Thus, fusion, as referred to hereinafter, may be effected by insertion of the antigen or antigenic determinant sequence in the sequence of a VLP subunit, by substitution of part of the sequence of the VLP subunit with the antigen or antigenic determinant, or by a combination of deletion, substitution or insertions.

The chimeric antigen or antigenic determinant-VLP subunit will be in general capable of self-assembly into a VLP. VLP displaying epitopes fused to their subunits are also herein referred to as chimeric VLPs. As indicated, the virus-like particle comprises or alternatively is composed of at least one VLP subunit. In a further embodiment of the invention, the virus-like particle comprises or alternatively is composed of a mixture of chimeric VLP subunits and non-chimeric VLP subunits, i.e. VLP subunits not having an antigen fused thereto, leading to so called mosaic particles. This may be advantageous to ensure formation of, and assembly to a VLP. In those embodiments, the proportion of chimeric VLP-subunits may be 1, 2, 5, 10, 20, 30, 40, 50, 60, 70, 80, 90, 95% or higher.

Flanking amino acid residues may be added to either end of the sequence of the peptide or epitope to be fused to either end of the sequence of the subunit of a VLP, or for internal insertion of such peptidic sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In a specific embodiment of the invention, the VLP is a Hepatitis B core antigen VLP. Fusion proteins of the antigen or antigenic determinant to either the N-terminus of a HBcAg (Neyrinck, S. et al., Nature Med. 5:1157-1163 (1999)) or insertions in the so called major immunodominant region (MIR) have been described (Pumpens, P. and Grens, E., Intervirology 44:98-114 (2001)), WO 01/98333), and are preferred embodiments of the invention. Naturally occurring variants of HBcAg with deletions in the MIR have also been described (Pumpens, P. and Grens, E., Intervirology 44:98-114 (2001), which is expressly incorporated by reference in its entirety), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., Intervirology 44:98-114 (2001)). One skilled in the art will easily find guidance on how to construct fusion proteins using classical molecular biology techniques (Sambrook, J. et al., eds., Molecular Cloning, A Laboratory Manual, 2nd. edition, Cold Spring Habor Laboratory Press, Cold Spring Harbor, N.Y. (1989), Ho et al., Gene 77:51 (1989)). Vectors and plasmids encoding HBcAg and HBcAg fusion proteins and useful for the expression of a HBcAg and HBcAg fusion proteins have been described (Pumpens, P. & Grens, E. Intervirology 44: 98-114 (2001), Neyrinck, S. et al., Nature Med. 5:1157-1163 (1999)) and can be used in the practice of the invention. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., Intervirology 44:98-114 (2001); EP 421 635; U.S. Pat. No. 6,231, 864) upon insertion, or in other words, which amino acids form HBcAg are to be substituted with the new epitope. For example, substitution of HBcAg amino acids 76-80, 79-81, 79-80, 75-85 or 80-81 with foreign epitopes has been described (Pumpens, P. and Grens, E., Intervirology 44:98-114 (2001); EP 421 635; U.S. Pat. No. 6,231,864). HBcAg contains a long arginine tail (Pumpens, P. and Grens, E., Intervirology 44:98-114 (2001)) which is dispensable for capsid assembly and capable of binding nucleic acids (Pumpens, P. and Grens, E., Intervirology 44:98-114 (2001)). HBcAg either comprising or lacking this arginine tail are both embodiments of the invention.

In a further preferred embodiment of the invention, the VLP is a VLP of a RNA phage. The major coat proteins of RNA phages spontaneously assemble into VLPs upon expression in bacteria, and in particular in $E.$ $coli.$ Specific examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein) and bacteriophage fr (SEQ ID NO: 13; PIR Accession No. VCBPFR).

In a more preferred embodiment, the at least one antigen or antigenic determinant is fused to a Qβ coat protein. Fusion protein constructs wherein epitopes have been fused to the C-terminus of a truncated form of the A1 protein of Qβ, or inserted within the A1 protein have been described (Kozlovska, T. M., et al., Intervirology, 39:9-15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qβ CP gene) usually takes place in $E.$ $coli$, and such is the case for N-termini of the Qβ coat proteins. The part of the A1 gene, 3' of the UGA amber codon encodes the CP extension, which has a length of 195 amino acids. Insertion of the at least one antigen or antigenic determinant between position 72 and 73 of the CP extension leads to further embodiments of the invention (Kozlovska, T. M., et al., Intervirology 39:9-15 (1996)). Fusion of an antigen or antigenic determinant at the C-terminus of a C-terminally truncated Qβ A1 protein leads to further preferred embodiments of the invention. For example, Kozlovska et al., (Intervirology, 39: 9-15 (1996)) describe Qβ A1 protein fusions where the epitope is fused at the C-terminus of the Qβ CP extension truncated at position 19.

As described by Kozlovska et al. (Intervirology, 39: 9-15 (1996)), assembly of the particles displaying the fused epitopes typically requires the presence of both the A1 protein-antigen fusion and the wt CP to form a mosaic particle. However, embodiments comprising virus-like particles, and hereby in particular the VLPs of the RNA phage Qβ coat protein, which are exclusively composed of VLP subunits having at least one antigen or antigenic determinant fused thereto, are also within the scope of the present invention.

The production of mosaic particles may be effected in a number of ways. Kozlovska et al., Intervirology, 39:9-15 (1996), describe three methods, which all can be used in the practice of the invention. In the first approach, efficient display of the fused epitope on the VLPs is mediated by the expression of the plasmid encoding the Qβ A1 protein fusion having a UGA stop codong between CP and CP extension in a $E.$ $coli$ strain harboring a plasmid encoding a cloned UGA suppressor tRNA which leads to translation of the UGA codon into Trp (pISM3001 plasmid (Smiley B. K., et al., Gene 134:33-40 (1993))). In another approach, the CP gene stop codon is modified into UAA, and a second plasmid expressing the A1 protein-antigen fusion is cotransformed. The second plasmid encodes a different antibiotic resistance and the origin of replication is compatible with the first plasmid (Kozlovska, T. M., et al., Intervirology 39:9-15 (1996)). In a third approach, CP and the A1 protein-antigen fusion are encoded in a bicistronic manner, operatively linked to a promoter such as the Trp promoter, as described in FIG. 1 of Kozlovska et al., Intervirology, 39:9-15 (1996).

In a further embodiment, the antigen or antigenic determinant is inserted between amino acid 2 and 3 (numbering of the cleaved CP, that is wherein the N-terminal methionine is cleaved) of the fr CP, thus leading to an antigen or antigenic determinant-fr CP fusion protein. Vectors and expression systems for construction and expression of fr CP fusion proteins self-assembling to VLP and useful in the practice of the invention have been described (Pushko P. et al., Prot. Eng. 6:883-891 (1993)). In a specific embodiment, the antigen or antigenic determinant sequence is inserted into a deletion variant of the fr CP after amino acid 2, wherein residues 3 and 4 of the fr CP have been deleted (Pushko P. et al., Prot. Eng. 6:883-891 (1993)).

Fusion of epitopes in the N-terminal protuberant β-hairpin of the coat protein of RNA phage MS-2 and subsequent presentation of the fused epitope on the self-assembled VLP of RNA phage MS-2 has also been described (WO 92/13081), and fusion of an antigen or antigenic determinant by insertion or substitution into the coat protein of MS-2 RNA phage is also falling under the scope of the invention.

In another embodiment of the invention, the antigen or antigenic determinant is fused to a capsid protein of papillomavirus. In a more specific embodiment, the antigen or antigenic determinant is fused to the major capsid protein L1 of bovine papillomavirus type 1 (BPV-1). Vectors and expression systems for construction and expression of BPV-1 fusion proteins in a baculovirus/insect cells systems have been described (Chackerian, B. et al., Proc. Natl. Acad. Sci. USA 96:2373-2378 (1999), WO 00/23955). Substitution of amino acids 130-136 of BPV-1 L1 with an antigen or antigenic determinant leads to a BPV-1 L1-antigen fusion protein, which is a preferred embodiment of the invention. Cloning in a baculovirus vector and expression in baculovirus infected Sf9 cells has been described, and can be used in the practice of the invention (Chackerian, B. et al., Proc. Natl. Acad. Sci. USA 96:2373-2378 (1999), WO 00/23955). Purification of the assembled particles displaying the fused antigen or antigenic determinant can be performed in a number of ways, such as for example gel filtration or sucrose gradient ultracentrifugation (Chackerian, B. et al., Proc. Natl. Acad. Sci. USA 96:2373-2378 (1999), WO 00/23955).

In a further embodiment of the invention, the antigen or antigenic determinant is fused to a Ty protein capable of being incorporated into a Ty VLP. In a more specific embodiment, the antigen or antigenic determinant is fused to the p1 or capsid protein encoded by the TYA gene (Roth, J. F., Yeast 16:785-795 (2000)). The yeast retrotransposons Ty1, 2, 3 and 4 have been isolated from *Saccharomyces Serevisiae*, while the retrotransposon Tf1 has been isolated from *Schizosaccharomyces Pombae* (Boeke, J. D. and Sandmeyer, S. B., "Yeast Transposable elements," in The molecular and Cellular Biology of the Yeast *Saccharomyces*: Genome dynamics, Protein Synthesis, and Energetics, p. 193, Cold Spring Harbor Laboratory Press (1991)). The retrotransposons Ty1 and 2 are related to the copia class of plant and animal elements, while Ty3 belongs to the gypsy family of retrotransposons, which is related to plants and animal retroviruses. In the Ty1 retrotransposon, the p1 protein, also referred to as Gag or capsid protein, has a length of 440 amino acids. P1 is cleaved during maturation of the VLP at position 408, leading to the p2 protein, the essential component of the VLP.

Fusion proteins to p1 and vectors for the expression of said fusion proteins in Yeast have been described (Adams, S. E., et al., Nature 329:68-70 (1987)). So, for example, an antigen or antigenic determinant may be fused to p1 by inserting a sequence coding for the antigen or antigenic determinant into the BamH1 site of the pMA5620 plasmid (Adams, S. E., et al., Nature 329:68-70 (1987)). The cloning of sequences coding for foreign epitopes into the pMA5620 vector leads to expression of fusion proteins comprising amino acids 1-381 of p1 of Ty1-15, fused C-terminally to the N-terminus of the foreign epitope. Likewise, N-terminal fusion of an antigen or antigenic determinant, or internal insertion into the p1 sequence, or substitution of part of the p1 sequence are also meant to fall within the scope of the invention. In particular, insertion of an antigen or antigenic determinant into the Ty sequence between amino acids 30-31, 67-68, 113-114 and 132-133 of the Ty protein p1 (EP0677111) leads to preferred embodiments of the invention.

Further VLPs suitable for fusion of antigens or antigenic determinants are, for example, Retrovirus-like-particles (WO9630523), HIV2 Gag (Kang, Y. C., et al, Biol. Chem. 380:353-364 (1999)), Cowpea Mosaic Virus (Taylor, K. M. et al., Biol. Chem. 380:387-392 (1999)), parvovirus VP2 VLP (Rueda, P. et al., Virology 263:89-99 (1999)), HBsAg (U.S. Pat. No. 4,722,840, EP0201416B1).

Examples of chimeric VLPs suitable for the practice of the invention are also those described in Intervirology 39:1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus have also been made, and chimeric VLPs of those VLPs comprising an antigen or antigenic determinant are also within the scope of the present invention.

As indicated, embodiments comprising antigens fused to the virus-like particle by insertion within the sequence of the virus-like particle building monomer are also within the scope of the present invention. In some cases, antigens can be inserted in a form of the virus-like particle building monomer containing deletions. In these cases, the virus-like particle building monomer may not be able to form virus-like structures in the absence of the inserted antigen.

In some instances, recombinant DNA technology can be utilized to fuse a heterologous protein to a VLP protein (Kratz, P. A., et al., Proc. Natl. Acad. Sci. USA 96:1915 (1999)). For example, the present invention encompasses VLPs recombinantly fused or chemically conjugated (including both covalently and non covalently conjugations) to an antigen (or portion thereof, preferably at least 10, 20 or 50 amino acids) of the present invention to generate fusion proteins or conjugates. The fusion does not necessarily need to be direct, but can occur through linker sequences. More generally, in the case that epitopes, either fused, conjugated or otherwise attached to the virus-like particle, are used as antigens in accordance with the invention, spacer or linker sequences are typically added at one or both ends of the epitopes. Such linker sequences preferably comprise sequences recognized by the proteasome, proteases of the endosomes or other vesicular compartment of the cell.

One way of coupling is by a peptide bond, in which the conjugate can be a contiguous polypeptide, i.e. a fusion protein. In a fusion protein according to the present invention, different peptides or polypeptides are linked in frame to each other to form a contiguous polypeptide. Thus a first portion of the fusion protein comprises an antigen or immunogen and a second portion of the fusion protein, either N-terminal or C-terminal to the first portion, comprises a VLP. Alternatively, internal insertion into the VLP, with optional linking sequences on both ends of the antigen, can also be used in accordance with the present invention.

When HBcAg is used as the VLP, it is preferred that the antigen is linked to the C-terminal end of the HBcAg particle. The hepatitis B core antigen (HBcAg) exhibiting a C-terminal fusion of the MHC class I restricted peptide p33 derived from lymphocytic choriomeningitis virus (LCMV) glycoprotein was used as a model antigen (HBcAg-p33). The 185 amino acids long wild type HBc protein assembles into highly structured particles composed of 180 subunits assuming icosahedral geometry. The flexibility of the HBcAg and other VLPs in accepting relatively large insertions of foreign sequences at different positions while retaining the capacity to form structured capsids is well documented in the literature. This makes the HBc VLPs attractive candidates for the design of non-replicating vaccines.

A flexible linker sequence (e.g. a polyglycine/polyserine-containing sequence such as [Gly4 Ser]2 (Huston et al., Meth. Enzymol 203:46-88 (1991)) can be inserted into the fusion protein between the antigen and ligand. Also, the fusion protein can be constructed to contain an "epitope tag", which allows the fusion protein to bind an antibody (e.g. monoclonal antibody) for example for labeling or purification purposes. An example of an epitope tag is a Glu-Glu-Phe tripeptide which is recognized by the monoclonal antibody YL1/2.

The invention also relates to the chimeric DNA which contains a sequence coding for the VLP and a sequence coding for the antigen/immunogen. The DNA can be expressed, for example, in insect cells transformed with Baculoviruses, in yeast or in bacteria. There are no restrictions regarding the expression system, of which a large selection is available for routine use. Preferably, a system is used which allows expression of the proteins in large amounts. In general, bacterial expression systems are preferred on account of their efficiency. One example of a bacterial expression system suitable for use within the scope of the present invention is the one described by Clarke et al., J. Gen. Virol. 71: 1109-1117 (1990); Borisova et al., J. Virol. 67: 3696-3701 (1993); and Studier et al., Methods Enzymol. 185:60-89 (1990). An example of a suitable yeast expression system is the one described by Emr, Methods Enzymol. 185:231-3 (1990); Baculovirus systems, which have previously been used for preparing capsid proteins, are also suitable. Constitutive or inducible expression systems can be used. By the choice and possible modification of available expression systems it is possible to control the form in which the proteins are obtained.

In a specific embodiment of the invention, the antigen to which an enhanced immune response is desired is coupled, fused or otherwise attached in frame to the Hepatitis B virus capsid (core) protein (HBcAg). However, it will be clear to all individuals in the art that other virus-like particles can be utilized in the fusion protein construct of the invention.

In a further preferred embodiment of the present invention, the at least one antigen or antigenic determinant is bound to the virus-like particle by at least one covalent bond. Preferably, the least one antigen or antigenic determinant is bound to the virus-like particle by at least one covalent bond, said covalent bond being a non-peptide bond leading to an antigen or antigenic determinant array and antigen or antigenic determinant-VLP conjugate, respectively. This antigen or antigenic determinant array and conjugate, respectively, has typically and preferably a repetitive and ordered structure since the at least one antigen or antigenic determinant is bound to the VLP in an oriented manner. Preferably, equal and more than 120, more preferably equal and more than 180, even more preferably more than 270, and again more preferably equal and more than 360 antigens of the invention are bound to the VLP. The formation of a repetitive and ordered antigen or antigenic determinant-VLP array and conjugate, respectively, is ensured by an oriented and directed as well as defined binding and attachment, respectively, of the at least one antigen or antigenic determinant to the VLP as will become apparent in the following. Furthermore, the typical inherent highly repetitive and organized structure of the VLPs advantageously contributes to the display of the antigen or antigenic determinant in a highly ordered and repetitive fashion leading to a highly organized and repetitive antigen or antigenic determinant-VLP array and conjugate, respectively.

Therefore, the preferred inventive conjugates and arrays, respectively, differ from prior art conjugates in their highly organized structure, dimensions, and in the repetitiveness of the antigen on the surface of the array. The preferred embodiment of this invention, furthermore, allows expression of the particle in an expression host guaranteeing proper folding and assembly of the VLP, to which the antigen is then further coupled The present invention discloses methods of binding of antigen or antigenic determinant to VLPs. As indicated, in one aspect of the invention, the at least one antigen or antigenic determinant is bound to the VLP by way of chemical cross-linking, typically and preferably by using a heterobifunctional cross-linker. Several hetero-bifunctional cross-linkers are known to the art. In preferred embodiments, the hetero-bifunctional cross-linker contains a functional group which can react with preferred first attachment sites, i.e. with the side-chain amino group of lysine residues of the VLP or at least one VLP subunit, and a further functional group which can react with a preferred second attachment site, i.e. a cysteine residue fused to the antigen or antigenic determinant and optionally also made available for reaction by reduction. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the antigen or antigenic determinant is reacted with the activated VLP, and this step is typically called the coupling step. Unreacted antigen or antigenic determinant may be optionally removed in a fourth step, for example by dialysis. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage. Another class of cross-linkers suitable in the practice of the invention is characterized by the introduction of a disulfide linkage between the antigen or antigenic determinant and the VLP upon coupling. Preferred cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength. The degree of coupling, i.e. the amount of antigens or antigenic determinants per subunits of the VLP can be adjusted by varying the experimental conditions described above to match the requirements of the vaccine.

A particularly favored method of binding of antigens or antigenic determinants to the VLP, is the linking of a lysine residue on the surface of the VLP with a cysteine residue on the antigen or antigenic determinant. In some embodiments, fusion of an amino acid linker containing a cysteine residue, as a second attachment site or as a part thereof, to the antigen or antigenic determinant for coupling to the VLP may be required.

In general, flexible amino acid linkers are favored. Examples of the amino acid linker are selected from the group consisting of: (a) CGG; (b) N-terminal gamma 1-linker; (c) N-terminal gamma 3-linker; (d) Ig hinge regions; (e) N-terminal glycine linkers; (f) (G)kC(G)n with n=0-12 and k=0-5; (g) N-terminal glycine-serine linkers; (h) (G)kC(G)m(S)l (GGGGS)n with n=0-3, k=0-5, m=0-10, l=0-2 (SEQ ID NO: 47); (i) GGC; (k) GGC-NH2; (l) C-terminal gamma 1-linker; (m) C-terminal gamma 3-linker; (n) C-terminal glycine linkers; (o) (G)nC(G)k with n=0-12 and k=0-5; (p) C-terminal glycine-serine linkers; (q) (G)m(S)l(GGGGS)n(G)oC(G)k with n=0-3, k=0-5, m=0-10, l=0-2, and o=0-8 (SEQ ID NO: 48).

Further examples of amino acid linkers are the hinge region of Immunoglobulins, glycine serine linkers (GGGGS)n (SEQ ID NO: 49), and glycine linkers (G)n all further containing a cysteine residue as second attachment site and optionally further glycine residues. Typically preferred examples of said amino acid linkers are N-terminal gamma 1: CGDKTHTSPP (SEQ ID NO: 50); C-terminal gamma 1: DKTHTSPPCG (SEQ ID NO: 51); N-terminal gamma 3: CGGPKPSTP-PGSSGGAP (SEQ ID NO: 52); C-terminal gamma 3: PKP-STPPGSSGGAPGGCG (SEQ ID NO: 53); N-terminal glycine linker: GCGGGG (SEQ ID NO: 54); C-terminal glycine linker: GGGGCG (SEQ ID NO: 55); C-terminal glycine-lysine linker: GGKKGC (SEQ ID NO: 56); N-terminal glycine-lysine linker: CGKKGG (SEQ ID NO: 57).

Other amino acid linkers particularly suitable in the practice of the invention, when a hydrophobic antigen or antigenic determinant is bound to a VLP, are CGKKGG (SEQ ID NO: 58), or CGDEGG (SEQ ID NO: 59) for N-terminal linkers, or GGKKGC (SEQ ID NO: 60) and GGEDGC (SEQ ID NO: 61), for the C-terminal linkers. For the C-terminal linkers, the terminal cysteine is optionally C-terminally amidated.

In preferred embodiments of the present invention, GGCG (SEQ ID NO: 62), GGC or GGC-NH2 ("NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction. In the most preferred embodiment of the invention, the amino acid linker GGC-NH2 is fused to the C-terminus of the antigen or antigenic determinant.

The cysteine residue present on the antigen or antigenic determinant has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e.g. DTT, TCEP or β-mercaptoethanol is required. Low concentrations of reducing agent are compatible with coupling as described in WO 02/05690, higher concentrations inhibit the coupling reaction, as a skilled artisan would know, in which case the reductand has to be removed or its concentration decreased prior to coupling, e.g. by dialysis, gel filtration or reverse phase BPLC.

Binding of the antigen or antigenic determinant to the VLP by using a hetero-bifunctional cross-linker according to the preferred methods described above, allows coupling of the antigen or antigenic determinant to the VLP in an oriented fashion. Other methods of binding the antigen or antigenic determinant to the VLP include methods wherein the antigen or antigenic determinant is cross-linked to the VLP using the carbodiimide EDC, and NHS. In further methods, the antigen or antigenic determinant is attached to the VLP using a homo-bifunctional cross-linker such as glutaraldehyde, DSG, BM[PEO]4, BS3, (Pierce Chemical Company, Rockford, Ill., USA) or other known homo-bifunctional cross-linkers whith functional groups reactive towards amine groups or carboxyl groups of the VLP.

Other methods of binding the VLP to an antigen or antigenic determinant include methods where the VLP is biotinylated, and the antigen or antigenic determinant expressed as a streptavidin-fusion protein, or methods wherein both the antigen or antigenic determinant and the VLP are biotinylated, for example as described in WO 00/23955. In this case, the antigen or antigenic determinant may be first bound to streptavidin or avidin by adjusting the ratio of antigen or antigenic determinant to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the antigen or antigenic determinant, may be used as binding agents for binding antigen or antigenic determinant to the VLP. Alternatively, either the ligand or the receptor may be fused to the antigen or antigenic determinant, and so mediate binding to the VLP chemically bound or fused either to the receptor, or the ligand respectively. Fusion may also be effected by insertion or substitution.

As already indicated, in a favored embodiment of the present invention, the VLP is the VLP of a RNA phage, and in a more preferred embodiment, the VLP is the VLP of RNA phage Qβ coat protein.

One or several antigen molecules, i.e. one or several antigens or antigenic determinants, can be attached to one subunit of the capsid or VLP of RNA phages coat proteins, preferably through the exposed lysine residues of the VLP of RNA phages, if sterically allowable. A specific feature of the VLP of the coat protein of RNA phages and in particular of the Qβ coat protein VLP is thus the possibility to couple several antigens per subunit. This allows for the generation of a dense antigen array.

In a preferred embodiment of the invention, the binding and attachment, respectively, of the at least one antigen or antigenic determinant to the virus-like particle is by way of interaction and association, respectively, between at least one first attachment site of the virus-like particle and at least one second attachment of the antigen or antigenic determinant.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In further preferred embodiments of the present invention, the first attachment site is a lysine residue and/or the second attachment comprises sulfhydryl group or a cysteine residue. In a very preferred embodiment of the present invention, the first attachment site is a lysine residue and the second attachment is a cysteine residue.

In very preferred embodiments of the invention, the antigen or antigenic determinant is bound via a cysteine residue, to lysine residues of the VLP of RNA phage coat protein, and in particular to the VLP of Qβ coat protein.

Another advantage of the VLPs derived from RNA phages is their high expression yield in bacteria that allows production of large quantities of material at affordable cost.

As indicated, the inventive conjugates and arrays, respectively, differ from prior art conjugates in their highly organized structure, dimensions, and in the repetitiveness of the antigen on the surface of the array. Moreover, the use of the VLPs as carriers allow the formation of robust antigen arrays and conjugates, respectively, with variable antigen density. In particular, the use of VLPs of RNA phages, and hereby in particular the use of the VLP of RNA phage Qβ coat protein allows to achieve very high epitope density. In particular, a density of more than 1.5 epitopes per subunit has been reached by coupling for example the human Aβ1-6 peptide to the VLP of Qβ coat protein (WO 2004/016282). The preparation of compositions of VLPs of RNA phage coat proteins with a high epitope density can be effected using the teaching of this application. In prefered embodiment of the invention, when an antigen or antigenic determinant is coupled to the VLP of Qβ coat protein, an average number of antigen or antigenic determinant per subunit of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4 2.5, 2.6, 2.7, 2.8, 2.9, or higher is preferred.

The second attachment site, as defined herein, may be either naturally or non-naturally present with the antigen or the antigenic determinant. In the case of the absence of a suitable natural occurring second attachment site on the antigen or antigenic determinant, such a, then non-natural second attachment has to be engineered to the antigen.

As described above, four lysine residues are exposed on the surface of the VLP of Qβ coat protein. Typically these residues are derivatized upon reaction with a cross-linker molecule. In the instance where not all of the exposed lysine residues can be coupled to an antigen, the lysine residues which have reacted with the cross-linker are left with a cross-linker molecule attached to the □-amino group after the derivatization step. This leads to disappearance of one or several positive charges, which may be detrimental to the solubility and stability of the VLP. By replacing some of the lysine residues with arginines, as in the disclosed Qβ coat protein mutants described below, we prevent the excessive disappearance of positive charges since the arginine residues do not react with the cross-linker. Moreover, replacement of lysine residues by arginines may lead to more defined antigen arrays, as fewer sites are available for reaction to the antigen.

Accordingly, exposed lysine residues were replaced by arginines in the following Qβ coat protein mutants and mutant Qβ VLPs disclosed in this application: Qβ-240 (Lys13-Arg; SEQ ID NO:20), Qβ-250 (Lys 2-Arg, Lys13-Arg; SEQ ID NO: 22) and Qβ-259 (Lys 2-Arg, Lys16-Arg; SEQ ID NO:24). The constructs were cloned, the proteins expressed, the VLPs purified and used for coupling to peptide and protein antigens. Qβ-251; (SEQ ID NO: 23) was also constructed, and guidance on how to express, purify and couple the VLP of Qβ-251 coat protein can be found throughout the application.

In a further embodiment, we disclose a Qβ mutant coat protein with one additional lysine residue, suitable for obtaining even higher density arrays of antigens. This mutant Qβ coat protein, Qβ-243 (Asn 10-Lys; SEQ ID NO: 21), was cloned, the protein expressed, and the capsid or VLP isolated and purified, showing that introduction of the additional lysine residue is compatible with self-assembly of the subunits to a capsid or VLP. Thus, antigen or antigenic determinant arrays and conjugates, respectively, may be prepared using VLP of Qβ coat protein mutants. A particularly favored method of attachment of antigens to VLPs, and in particular to VLPs of RNA phage coat proteins is the linking of a lysine residue present on the surface of the VLP of RNA phage coat proteins with a cysteine residue added to the antigen. In order for a cysteine residue to be effective as second attachment site, a sulfhydryl group must be available for coupling. Thus, a cysteine residue has to be in its reduced state, that is, a free cysteine or a cysteine residue with a free sulfhydryl group has to be available. In the instant where the cysteine residue to function as second attachment site is in an oxidized form, for example if it is forming a disulfide bridge, reduction of this disulfide bridge with e.g. DTT, TCEP or β-mercaptoethanol is required. The concentration of reductant, and the molar excess of reductand over antigen has to be adjusted for each antigen. A titration range, starting from concentrations as low as 10 μM or lower, up to 10 to 20 mM or higher reductand if required is tested, and coupling of the antigen to the carrier assessed. Although low concentrations of reductand are compatible with the coupling reaction as described in WO 02/056905, higher concentrations inhibit the coupling reaction, as a skilled artisan would know, in which case the reductand has to be removed or its concentration decreased, e.g. by dialysis, gel filtration or reverse phase HPLC. Advantageously, the pH of the dialysis or equilibration buffer is lower than 7, preferably 6. The compatibility of the low pH buffer with antigen activity or stability has to be tested.

Epitope density on the VLP of RNA phage coat proteins can be modulated by the choice of cross-linker and other reaction conditions. For example, the cross-linkers Sulfo-GMBS and SMPH typically allow reaching high epitope density. Derivatization is positively influenced by high concentration of reactands, and manipulation of the reaction conditions can be used to control the number of antigens coupled to VLPs of RNA phage coat proteins, and in particular to VLPs of Qβ coat protein.

Prior to the design of a non-natural second attachment site the position at which it should be fused, inserted or generally engineered has to be chosen. The selection of the position of the second attachment site may, by way of example, be based on a crystal structure of the antigen. Such a crystal structure of the antigen may provide information on the availability of the C- or N-termini of the molecule (determined for example from their accessibility to solvent), or on the exposure to solvent of residues suitable for use as second attachment sites, such as cysteine residues. Exposed disulfide bridges, as is the case for Fab fragments, may also be a source of a second attachment site, since they can be generally converted to single cysteine residues through mild reduction, with e.g. 2-mercaptoethylamine, TCEP, β-mercaptoethanol or DTT. Mild reduction conditions not affecting the immunogenicity of the antigen will be chosen. In general, in the case where immunization with a self-antigen is aiming at inhibiting the interaction of this self-antigen with its natural ligands, the second attachment site will be added such that it allows generation of antibodies against the site of interaction with the natural ligands. Thus, the location of the second attachment site will be selected such that steric hindrance from the second attachment site or any amino acid linker containing the same is avoided. In further embodiments, an antibody response directed at a site distinct from the interaction site of the self-antigen with its natural ligand is desired. In such embodiments, the second attachment site may be selected such that it prevents generation of antibodies against the interaction site of the self-antigen with its natural ligands.

Other criteria in selecting the position of the second attachment site include the oligomerization state of the antigen, the site of oligomerization, the presence of a cofactor, and the availability of experimental evidence disclosing sites in the antigen structure and sequence where modification of the antigen is compatible with the function of the self-antigen, or with the generation of antibodies recognizing the self-antigen.

In very preferred embodiments, the antigen or antigenic determinant comprises a single second attachment site or a single reactive attachment site capable of association with the first attachment sites on the core particle and the VLPs or VLP subunits, respectively. This further ensures a defined and uniform binding and association, respectively, of the at least one, but typically more than one, preferably more than 10, 20, 40, 80, 120, 150, 180, 210, 240, 270, 300, 360, 400, 450 antigens to the core particle and VLP, respectively. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine- (as the first attachment site) and cysteine- (as a second attachment site) interaction, it is ensured, in accordance with this preferred embodiment of the invention, that only one cysteine residue per antigen, independent whether this cysteine residue is naturally or non-naturally present on the antigen, is capable of binding and associating, respectively, with the VLP and the first attachment site of the core particle, respectively.

In some embodiments, engineering of a second attachment site onto the antigen require the fusion of an amino acid linker containing an amino acid suitable as second attachment site according to the disclosures of this invention. Therefore, in a preferred embodiment of the present invention, an amino acid linker is bound to the antigen or the antigenic determinant by way of at least one covalent bond. Preferably, the amino acid linker comprises, or alternatively consists of, the second attachment site. In a further preferred embodiment, the amino acid linker comprises a sulfhydryl group or a cysteine residue. In another preferred embodiment, the amino acid linker is cysteine. Some criteria of selection of the amino acid linker as well as further preferred embodiments of the amino acid linker according to the invention have already been mentioned above.

In another specific embodiment of the invention, the attachment site is selected to be a lysine or cysteine residue that is fused in frame to the HBcAg. In a preferred embodiment, the antigen is fused to the C-terminus of HBcAg via a three leucine linker.

When an antigen or antigenic determinant is linked to the VLP through a lysine residue, it may be advantageous to either substitute or delete one or more of the naturally resident lysine residues, as well as other lysine residues present in HBcAg variants.

In many instances, when the naturally resident lysine residues are eliminated, another lysine will be introduced into the HBcAg as an attachment site for an antigen or antigenic determinant. Methods for inserting such a lysine residue are known in the art. Lysine residues may also be added without removing existing lysine residues.

The C terminus of the HBcAg has been shown to direct nuclear localization of this protein. (Eckhardt et al., J. Virol. 65:575 582 (1991)). Further, this region of the protein is also believed to confer upon the HBcAg the ability to bind nucleic acids.

As indicated, HBcAgs suitable for use in the practice of the present invention also include N terminal truncation mutants. Suitable truncation mutants include modified HBcAgs where 1, 2, 5, 7, 9, 10, 12, 14, 15, or 17 amino acids have been removed from the N terminus. However, variants of virus-like particles containing internal deletions within the sequence of the subunit composing the virus-like particle are also suitable in accordance with the present invention, provided their compatibility with the ordered or particulate structure of the virus-like particle. For example, internal deletions within the sequence of the HBcAg are suitable (Preikschat, P., et al., J. Gen. Virol. 80:1777-1788 (1999)).

Further HBcAgs suitable for use in the practice of the present invention include N- and C terminal truncation mutants. Suitable truncation mutants include HBcAgs where 1, 2, 5, 7, 9, 10, 12, 14, 15, and 17 amino acids have been removed from the N terminus and 1, 5, 10, 15, 20, 25, 30, 34, 35, 36, 37, 38, 39 40, 41, 42 or 48 amino acids have been removed from the C terminus.

Vaccine compositions of the invention can comprise mixtures of different HBcAgs. Thus, these vaccine compositions can be composed of HBcAgs which differ in amino acid sequence. For example, vaccine compositions could be prepared comprising a "wild type" HBcAg and a modified HBcAg in which one or more amino acid residues have been altered (e.g., deleted, inserted or substituted). In most applications, however, only one type of a HBcAg will be used.

In a preferred embodiment, the virus-like particle comprises at least one first attachment site and the antigen or antigenic determinant comprises at least one second attachment site. Preferably, the first attachment site comprises, or preferably consists of, an amino group or a lysine residue. The second attachment site is preferably selected from the group consisting of (a) an attachment site not naturally occurring with said antigen or antigenic determinant; and (b) an attachment site naturally occurring with said antigen or antigenic determinant. Even more preferably, the second attachment site comprises, or preferably consists of, a sulfhydryl group or a cysteine residue. In a preferred embodiment, the binding of the antigen or antigenic determinant to the virus-like particle is effected through association between the first attachment site and the second attachment site, wherein preferably the association is through at least one non-peptide bond, and wherein preferably the antigen or antigenic determinant and the virus-like particle interact through said association to form an ordered and repetitive antigen array. In one embodiment, the first attachment site is a lysine residue and the second attachment site is a cysteine residue. In another embodiment, the first attachment site is an amino group and the second attachment site is a sulfhydryl group.

In a specific embodiment of the invention, the antigen or antigenic determinat, comprises one or more cytotoxic T cell epitopes, Th cell epitopes, or a combination of the two epitopes. Thus, in one embodiment, the antigen or antigenic determinant comprises one, two, or more cytotoxic T cell epitopes. In another embodiment, the antigen or antigenic determinant comprises one, two, or more Th cell epitopes. In yet another embodiment, the antigen or antigenic determinant comprises one, two or more cytotoxic T cell epitopes and one, two or more Th cell epitopes.

The present invention is applicable to a wide variety of antigens. In a preferred embodiment, the antigen is a protein, polypeptide or peptide. In another embodiment the antigen is DNA. The antigen can also be a lipid, a carbohydrate, or an organic molecule, in particular a small organic molecule such as nicotine.

Antigens of the invention can be selected from the group consisting of the following: (a) polypeptides suited to induce an immune response against cancer cells; (b) polypeptides suited to induce an immune response against infectious diseases; (c) polypeptides suited to induce an immune response against allergens; (d) polypeptides suited to induce an immune response in farm animals or pets; and (e) fragments (e.g., a domain) of any of the polypeptides set out in (a) (d).

Preferred antigens include those from a pathogen (e.g. virus, bacterium, parasite, fungus) and tumors (especially tumor-associated antigens or "tumor markers"). Other preferred antigens are autoantigens and self antigens, respectively.

In the specific embodiments described in the Examples, the antigen is the peptide p33 derived from lymphocytic choriomeningitis virus (LCMV). The p33 peptide represents one of the best studied CTL epitopes (Pircher et al., "Tolerance induction in double specific T-cell receptor transgenic mice varies with antigen," Nature 342:559 (1989); Tissot et al., "Characterizing the functionality of recombinant T-cell receptors in vitro: a pMHC tetramer based approach," J Immunol Methods 236:147 (2000); Bachmann et al., "Four types of Ca2+-signals after stimulation of naive T cells with T cell agonists, partial agonists and antagonists," Eur. J. Immunol. 27:3414 (1997); Bachmann et al., "Functional maturation of an anti-viral cytotoxic T cell response," J. Virol. 71:5764 (1997); Bachmann et al., "Peptide induced TCR-down regulation on naive T cell predicts agonist/partial agonist properties and strictly correlates with T cell activation," Eur. J. Immunol. 27:2195 (1997); Baclunann et al., "Distinct roles for LFA-1 and CD28 during activation of naive T cells: adhesion versus costimulation," Immunity 7:549 (1997)). p33-specific T cells have been shown to induce lethal diabetic disease in transgenic mice (Ohashi et al., "Ablation of 'tolerance' and induction of diabetes by virus infection in viral antigen transgenic mice," Cell 65:305 (1991)) as well as to be able to prevent growth of tumor cells expressing p33 (Kündig et al., "Fibroblasts act as efficient antigen-presenting cells in lymphoid organs," Science 268:1343 (1995); Speiser et al., "CTL tumor therapy specific for an endogenous antigen does not cause autoimmune disease," J. Exp. Med. 186:645 (1997)). This specific epitope, therefore, is particularly well suited to study autoimmunity, tumor immunology as well as viral diseases.

In one specific embodiment of the invention, the antigen or antigenic determinant is one that is useful for the prevention of infectious disease. Such treatment will be useful to treat a wide variety of infectious diseases affecting a wide range of hosts, e.g., human, cow, sheep, pig, dog, cat, other mammalian species and non-mammalian species as well. Treatable infectious diseases are well known to those skilled in the art, and examples include infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc. Thus, antigens or antigenic determinants selected for the compositions of the invention will be well known to those in the medical art; examples of antigens or antigenic determinants include the following: the HIV antigens gp140 and gp160; the influenza antigens hemagglutinin, M2 protein and neuraminidase, Hepatitis B surface antigen or core and circumsporozoite protein of malaria or fragments thereof.

As discussed above, antigens include infectious microbes such as viruses, bacteria and fungi and fragments thereof, derived from natural sources or synthetically. Infectious viruses of both human and non-human vertebrates include retroviruses, RNA viruses and DNA viruses. The group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include. Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A, C, D, E and G viruses, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picomavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses and filoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxyiridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D and E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc.). Finally, DNA viruses may include viruses which do not fit into the above families such as Kuru and Creutzfeldt-Jacob disease viruses and chronic infectious neuropathic agents (CHINA virus).

Each of the foregoing lists is illustrative, and is not intended to be limiting.

In a specific embodiment of the invention, the antigen comprises one or more cytotoxic T cell epitopes, Th cell epitopes, or a combination of the two epitopes.

In addition to enhancing an antigen specific immune response in humans, the methods of the preferred embodiments are particularly well suited for treatment of other mammals or other animals, e.g., birds such as hens, chickens, turkeys, ducks, geese, quail and pheasant. Birds are prime targets for many types of infections.

An example of a common infection in chickens is chicken infectious anemia virus (CIAV). CIAV was first isolated in Japan in 1979 during an investigation of a Marek's disease vaccination break (Yuasa et al., Avian Dis. 23:366-385 (1979)). Since that time, CIAV has been detected in commercial poultry in all major poultry producing countries (van Bulow et al., pp. 690-699 in "Diseases of Poultry", 9th edition, Iowa State University Press 1991).

Vaccination of birds, like other vertebrate animals can be performed at any age. Normally, vaccinations are performed at up to 12 weeks of age for a live microorganism and between 14-18 weeks for an inactivated microorganism or other type of vaccine. For in ovo vaccination, vaccination can be performed in the last quarter of embryo development. The vaccine can be administered subcutaneously, by spray, orally, intraocularly, intratracheally, nasally, in ovo or by other methods described herein.

Cattle and livestock are also susceptible to infection. Disease which affect these animals can produce severe economic losses, especially amongst cattle. The methods of the invention can be used to protect against infection in livestock, such as cows, horses, pigs, sheep and goats.

Cows can be infected by bovine viruses. Bovine viral diarrhea virus (BVDV) is a small enveloped positive-stranded RNA virus and is classified, along with hog cholera virus (HOCV) and sheep border disease virus (BDV), in the pestivirus genus. Although Pestiviruses were previously classified in the Togaviridae family, some studies have suggested their reclassification within the Flaviviridae family along with the flavivirus and hepatitis C virus (HCV) groups.

Equine herpesviruses (EHV) comprise a group of antigenically distinct biological agents which cause a variety of infections in horses ranging from subclinical to fatal disease. These include Equine herpesvirus-1 (EHV-1), a ubiquitous pathogen in horses. EHV-1 is associated with epidemics of abortion, respiratory tract disease, and central nervous system disorders. Other EHV's include EHV-2, or equine cytomegalovirus, EHV-3, equine coital exanthema virus, and EHV4, previously classified as EHV-1 subtype 2.

Sheep and goats can be infected by a variety of dangerous microorganisms including visna-maedi.

Primates such as monkeys, apes and macaques can be infected by simian immunodeficiency virus. Inactivated cell-virus and cell-free whole simian immunodeficiency vaccines have been reported to afford protection in macaques (Stott et al., Lancet 36:1538-1541 (1990); Desrosiers et al., PNAS USA 86:6353-6357 (1989); Murphey-Corb et al., Science 246:1293-1297 (1989); and Carlson et al., AIDS Res. Human Retroviruses 6:1239-1246 (1990)). A recombinant HIV gp120 vaccine has been reported to afford protection in chimpanzees (Berman et al., Nature 345:622-625 (1990)).

Cats, both domestic and wild, are susceptible to infection with a variety of microorganisms. For instance, feline infectious peritonitis is a disease which occurs in both domestic and wild cats, such as lions, leopards, cheetahs, and jaguars. When it is desirable to prevent infection with this and other types of pathogenic organisms in cats, the methods of the invention can be used to vaccinate cats to prevent them against infection.

Domestic cats may become infected with several retroviruses, including but not limited to feline leukemia virus (FeLV), feline sarcoma virus (FeSV), endogenous type C oncomavirus (RD-114), and feline syncytia-forming virus (FeSFV). The discovery of feline T-lymphotropic lentivims (also referred to as feline immunodeficiency) was first reported in Pedersen et al., Science 235:790-793 (1987). Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat and pallas cat.

Viral and bacterial diseases in fin-fish, shellfish or other aquatic life forms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic life forms facility. Prevention of disease is a more desired remedy to these threats to fish than intervention once the disease is in progress. Vaccination of fish is the only preventative method which may offer long-term protection through immunity. Nucleic acid based vaccinations of fish are described, for example, in U.S. Pat. No. 5,780,448.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Vaccines can be administered orally or by immersion or injection.

Aquaculture species include but are not limited to fin-fish, shellfish, and other aquatic animals. Fin-fish include all vertebrate fish, which may be bony or cartilaginous fish, such as, for example, salmonids, carp, catfish, yellowtail, seabream and seabass. Salmonids are a family of fin-fish which include trout (including rainbow trout), salmon and Arctic char. Examples of shellfish include, but are not limited to, clams, lobster, shrimp, crab and oysters. Other cultured aquatic animals include, but are not limited to, eels, squid and octopi.

Polypeptides of viral aquaculture pathogens include but are not limited to glycoprotein or nucleoprotein of viral hemorrhagic septicemia virus (VHSV); G or N proteins of infectious hematopoietic necrosis virus (IHNV); VP1, VP2, VP3 or N structural proteins of infectious pancreatic necrosis virus (IPNV); G protein of spring viremia of carp (SVC); and a membrane-associated protein, tegumin or capsid protein or glycoprotein of channel catfish virus (CCV).

Polypeptides of bacterial pathogens include but are not limited to an iron-regulated outer membrane protein, (IROMP), an outer membrane protein (OMP), and an A-protein of *Aeromonis salmonicida* which causes furunculosis, p57 protein of *Renibacterium salmoninarum* which causes bacterial kidney disease (13 KD), major surface associated antigen (msa), a surface expressed cytotoxin (mpr), a surface expressed hemolysin (ish), and a flagellar antigen of Yersiniosis; an extracellular protein (ECP), an iron-regulated outer membrane protein (IROMP), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of Ichthyophthirius; and a structural and regulatory protein of *Cytophaga columnari*; and a structural and regulatory protein of *Rickettsia*.

Polypeptides of a parasitic pathogen include but are not limited to the surface antigens of Ichthyophthirius.

In another aspect of the invention, there is provided vaccine compositions suitable for use in methods for preventing and/or attenuating diseases or conditions which are caused or exacerbated by "self" gene products (e.g., tumor necrosis factors). Thus, vaccine compositions of the invention include compositions which lead to the production of antibodies that prevent and/or attenuate diseases or conditions caused or exacerbated by "self" gene products. Examples of such diseases or conditions include graft versus host disease, IgE mediated allergic reactions, anaphylaxis, adult respiratory distress syndrome, Crohn's disease, allergic asthma, acute lymphoblastic leukemia (ALL), non Hodgkin's lymphoma HL), Graves' disease, systemic lupus erythematosus (SLE), inflammatory autoimmune diseases, myasthenia gravis, immunoproliferative disease lymphadenopathy (IPL), angio-immunoproliferative lymphadenopathy (AIL), immunoblastive lymphadenopathy (IBL), rheumatoid arthritis, diabetes, prion diseases, multiple sclerosis, Alzheimer disease and osteoporosis.

In related specific embodiments, compositions of the invention are an immunotherapeutic that can be used for the treatment and/or prevention of allergies, cancer or drug addiction.

The selection of antigens or antigenic determinants for the preparation of compositions and for use in methods of treatment for allergies would be known to those skilled in the medical arts treating such disorders. Representative examples of such antigens or antigenic determinants include the following: bee venom phospholipase A2, Bet v I (birch pollen allergen), 5 Dol m V (white-faced hornet venom allergen), and Der p I (House dust mite allergen), as well as fragments of each which can be used to elicit immunological responses.

The selection of antigens or antigenic determinants for compositions and methods of treatment for cancer would be known to those skilled in the medical arts treating such disorders (see Renkvist et al., Cancer. Immunol. Immunother. 50:3-15 (2001) which is incorporated by reference), and such antigens or antigenic determinants are included within the scope of the present invention. Representative examples of such types of antigens or antigenic determinants include the following: Her2 (breast cancer); GD2 (neuroblastoma); EGF-R (malignant glioblastoma); CEA (medullary thyroid cancer); CD52 (leukemia); human melanoma protein gp100;

human melanoma protein gp100 epitopes such as amino acids 154-162 (sequence: KTWGQYWQV) (SEQ ID NO: 63), 209-217 (ITDQVPFSV) (SEQ ID NO: 64), 280-288 (YLEPGPVTA) (SEQ ID NO: 65), 457-466 (LLDGTATLRL) (SEQ ID NO: 66) and 476-485 (VLYRYGSFSV) (SEQ ID NO: 67); human melanoma protein melan-A/MART-1; human melanoma protein melan-A/MART-1 epitopes such as amino acids 26-35 (EAAGIGILTV) (SEQ ID NO:68), 27-35 (AAGIGILTV) (SEQ ID NO: 69) and 32-40 (ILTVILGVL) (SEQ ID NO: 70); tyrosinase and tyrosinase related proteins (e.g., TRP-1 and TRP-2); tyrosinase epitopes such as amino acids 1-9 (MLLAVLYCL) (SEQ ID NO: 71) and 369-377 (YMDGTMSQV) (SEQ ID NO: 72); NA17-A nt protein; NA17-A nt protein epitopes such as amino acids 38-64 (VLPDVFIRC) (SEQ ID NO: 73); MAGE-3 protein; MAGE-3 protein epitopes such as amino acids 271-279 (FLWGPRALV) (SEQ ID NO: 74); other human tumors antigens, e.g. CEA epitopes such as amino acids 571-579 (YLSGANLNL) (SEQ ID NO: 75); p53 protein; p53 protein epitopes such as amino acids 65-73 (RMPEAAPPV) (SEQ ID NO: 76), 149-157 (STPPPGTRV) (SEQ ID NO: 77) and 264-272 (LLGRNSFEV) (SEQ ID NO: 78); Her2/neu epitopes such as amino acids 369-377 (KIFGSLAFL) (SEQ ID NO: 79) and 654-662 (IISAVVGIL) (SEQ ID NO: 80); NY-ESO-1 peptides 157-165 and 157-167, 159-167; HPV16 E7 protein; HPV16 E7 protein epitopes such as amino acids 86-93 (TLGIVCPI) (SEQ ID NO: 81); as well as fragments or mutants of each which can be used to elicit immunological responses.

The natural MelanA/Mart-1 epitopes, and for example the MelanA/Mart-1 26-35 epitope bind with low affinity to human HLA-2 only. Thus, in vivo presentation of the natural MelanA epitopes and peptides, respectively, upon vaccination may be a limiting factor. This is particularly important if Melan A epitopes and peptides, respectively, bound, coupled or fused to VLPs are used for vaccination, since under these conditions, MelanA peptides load HLA molecules by cross-presentation. The process of cross-presentation is, however, not as efficient as classical pathways of antigen presentation and the affinity of the MelanA peptide for HLA is even more important. Thus, for VLP-based vaccinations, it is very preferable to use MelanA peptides that bind with relatively high affinity to HLA. Similarly, it may also be advantageous to use MelanA peptides that are recognized with higher affinity by the natural T cell repertoire of the host. As a general rule, MelanA epitopes and peptides, respectively, are preferred that contain anchor residues at the proper positions allowing for efficient binding to MHC molecules.

Therefore, a further aspect of the present invention and a preferred embodiment of the present invention is to provide a composition for enhancing an immune response in an animal comprising (a) a virus-like particle; and (b) an immunostimulatory substance, wherein said immunostimulatory substance is bound to said virus-like particle, and wherein said composition further comprises at least one antigen or antigenic determinant, wherein said antigen or antigenic determinant is bound to said virus-like particle, and wherein said at least one antigen or antigenic determinant comprises, alternatively consists essentially of, or alternatively consists of a human melanoma MelanA peptide analogue, and wherein said human melanoma MelanA peptide analogue is bound to said virus-like particle.

The term "natural human Melan A peptide" or "normal human Melan A peptide" as used herein, shall refer to a peptide comprising, or alternatively consisting essentially of, or consisting of the amino acid sequence EAAGIGILTV (SEQ ID NO: 68) representing amino acids positions 26-35 of the normal human MelanA protein sequence or AAGIGILTV (SEQ ID NO: 69) representing amino acids positions 27-35 of the normal human MelanA protein sequence.

A "MelanA peptide analogue" as used herein shall be defined as a peptide in which the amino acid sequence of the corresponding naturally occuring normal MelanA peptide is altered by at least one amino acid or amino acid derivative, wherein this alteration may comprise an amino acid substitution and/or deletion and/or insertion or a combination thereof. In a preferred embodiment of the present invention, the term "MelanA peptide analogue A" as used herein shall be defined as a peptide in which the amino acid sequence of the corresponding naturally occuring normal MelanA peptide is altered by three, preferably two, and even more preferably one, amino acid or amino acid derivative, wherein this alteration may comprise an amino acid substitution and/or deletion and/or insertion or a combination thereof. In a further preferred embodiment of the present invention, the term "MelanA peptide analogue A" as used herein shall be defined as a peptide in which the amino acid sequence of the corresponding naturally occuring normal MelanA peptide is altered by three, preferably two, and even more preferably one, amino acid or amino acid derivative, wherein this alteration may comprise an amino acid substitution and/or deletion and/or insertion or a combination thereof, and wherein this alteration is at position 26, 27, 28 and/or 35 of the normal human MelanA protein sequence (SEQ ID NO: 109).

In a preferred embodiment of the present invention, the Melan A peptide analogue is capable of allowing an efficient binding to MHC molecules. The use of a MelanA peptide analogue, thus, allows, in particular, the introduction of such anchor residues leading to an improved binding to MHC molecules. The introduction of such anchor residues leading to an improved binding to MHC molecules is in particular advantageous, if the natural and normal, respectively, MelanA peptide does not contain such anchor residues or does not contains only such anchor residues which are inferior to the newly introduced anchor residue(s) replacing the natural and normal, respectively anchor residue.

The modification of the normal human MelanA peptide leading to the MelanA peptide analogue, and hereby preferably the introduction of these anchor residues is effected either by (i) induced mutation (e.g. chemical induction, irradiation or other procedures known to a person skilled in the art) and subsequent selection of modified peptides with improved binding to MHC or (ii) of selection of modified peptides with improved binding to MHC arising from natural mutations arising at any level of protein sythesis, including but not limited to mutations arising at the DNA, transcriptional, RNA or translational level of protein expression or (iii) or by systematic or random amino acid exchanges, deletions, substitutions or insertions by using classical peptide synthesis known by the person skilled in the art. The identification of such anchor residues is typically and preferably effected by using the SYFPEITHI database as described by Rammensee et al. in Immunogenetics 50:213-219 (1999). The SYFPEITHI database allows calculating the efficiency of HLA binding for any peptide of choice and it is possible to optimize the peptides regarding the efficiency of HLA binding using this program. Alternatively, identification of preferred peptide analogues can be achieved by MHC-peptide binding assays involving but not limited to whole cell assays of T cell activation or recognition or MHC upregualtion in mutant cell lines, MHC-tetramer-peptide binding assays, competitive binding assays with labelled peptides, surface plasmon resonance assays, all known to the person skilled in the art.

In a further preferred embodiment of the present invention, the MelanA peptide analogue is characterized by two, more preferably by a single amino acid substitution with respect to the corresponding normal MelanA peptide.

In another preferred embodiment of the present invention, the MelanA peptide analogue is protected from protease or peptidase mediated degradation. The use of MelanA peptide analogues that are protected from protease or peptidase degradation leads to increased stability of the peptide in vivo after application of the peptide to a subject or and/or to increased stability of the peptide during storage in the presence of proteases or peptidases. The consequence of this increased stability is more efficient and prolonged presentation of the human melanoma MelanA peptide analogue on MHC and thus the enhanced stimulation of a specific T cell response.

Preferably, the human MelanA peptide analogue is protected by substitution of selected amino acid residues of the natural human MelanA peptide by non natural amino acid derivatives as exemplified in Blanchet et al, J. Immunol. 167: 5852-5861 (2001) and references cited therein. This overcomes the limitation typically imposed by the fact that chemically modified MelanA peptides and MelanA peptide analogues, respectively, may not be recognized by the T cells equally well as compared to the natural and normal, respectively, MelanA peptide.

In another preferred embodiment, the antigen comprises, alternatively consists essentially of, or alternatively consists of a human melanoma MelanA/MART-1 peptide analogue having an amino acid sequence which is selected from the group consisting of (a) LAGIGILTV (SEQ ID NO: 89); (b) MAGIGILTV (SEQ ID NO: 90); (c) EAAGIGILTV (SEQ ID NO: 68), (d) EAMGIGILTV (SEQ ID NO: 91), (e) ELAGIGILTV (SEQ ID NO: 35), (f) EMAGIGILTV (SEQ ID NO: 92), (g) YAAGIGILTV (SEQ ID NO: 93), and (h) FAAGIGILTV (SEQ ID NO: 94). These peptide analogues as well as their syntheses have been described by Valmori at al., J. Immunol. 160: 1750-1758 (1998). These peptide analogues show increased relative recognition and target cell lysis by five different cytotoxic T cell clones raised against the natural melanoma peptide.s In a very preferred embodiment of the present invention the human melanoma MelanA/MART-1 peptide analogue comprises, alternatively consists essentially of, or alternatively consists of the sequence ELAGIGILTV (SEQ ID NO: 35). As indicated throughout the examples this very preferred embodiment induces expansion of functional MelanA-specific CD8+T cells in HLA-A2 transgenic mice and represents a good compromise between HLA-binding and TCR-recognition (cf. Valmori at al., J. Immunol. 160: 1750-1758 (1998)).

In a further very preferred embodiment of the present invention the human melanoma MelanA/MART-1 peptide analogue with the second attachment site has an amino acid sequence selected from (a) CGHGHSYTTAEELAGIGILTV (SEQ ID NO: 40); and typically abbreviated herein as MelanA 16-35 A/L), (b) CGGELAGIGILTV (SEQ ID NO: 42); and typically abbreviated herein as MelanA 26-35 A/L), (c) CSYTTAEELAGIGILTVILGVL (SEQ ID NO: 43); and typically abbreviated herein as MelanA 20-40 A/L), (d) CGGELAGIGILTVILGVL (SEQ ID NO: 44); and typically abbreviated herein as MelanA 26-40 A/L), (e) ELAGIGILTVGGC (SEQ ID NO: 45); typically abbreviated herein as MelanA 26-35-C A/L), (f) CSPKSLELAGIGILTV (SEQ ID NO: 77), and typically abbreviated herein as CSPKSL-MelanA 26-35 A/L; and (g) ELAGIGILTVILGVLGGC (SEQ ID NO: 78), and typically abbreviated herein as MelanA 26-40-C A/L.

In another very preferred embodiment of the present invention the human melanoma MelanA/MART-1 peptide analogue with the second attachment has an amino acid sequence of CGHGHSYTTAEELAGIGILTV (SEQ ID NO: 40).

The selection of antigens or antigenic determinants for compositions and methods of treatment for drug addiction, in particular recreational drug addiction, would be known to those skilled in the medical arts treating such disorders. Representative examples of such antigens or antigenic determinants include, for example, opioids and morphine derivatives such as codeine, fentanyl, heroin, morphium and opium; stimulants such as amphetamine, cocaine, MDMA (methylenedioxymethamphetamine), methamphetamine, methylphenidate and nicotine; hallucinogens such as LSD, mescaline and psilocybin; as well as cannabinoids such as hashish and marijuana.

The selection of antigens or antigenic determinants for compositions and methods of treatment for other diseases or conditions associated with self antigens would be also known to those skilled in the medical arts treating such disorders. Representative examples of such antigens or antigenic determinants are, for example, lymphotoxins (e.g. Lymphotoxin α (LT α), Lymphotoxin β (LT β)), and lymphotoxin receptors, Receptor activator of nuclear factor kappaB ligand (RANKL), vascular endothelial growth factor (VEGF) and vascular endothelial growth factor receptor (VEGF-R), Interleukin 17 and amyloid beta peptide (Aβ1-42), TNFα, MIF, MCP-1, SDF-1, Rank-L, M-CSF, Angiotensin II, Endoglin, Eotaxin, Grehlin, BLC, CCL21, IL-13, IL-17, IL-5, IL-8, IL-15, Bradykinin, Resistin, LHRH, GHRH, GIH, CRH, TRH and Gastrin, as well as fragments of each which can be used to elicit immunological responses.

In a particular embodiment of the invention, the antigen or antigenic determinant is selected from the group consisting of: (a) a recombinant polypeptide of HIV; (b) a recombinant polypeptide of Influenza virus (e.g., an Influenza virus M2 polypeptide or a fragment thereof); (c) a recombinant polypeptide of Hepatitis C virus; (d) a recombinant polypeptide of Hepatitis B virus (e) a recombinant polypeptide of *Toxoplasma*; (f) a recombinant polypeptide of *Plasmodium falciparum*; (g) a recombinant polypeptide of *Plasmodium vivax*; (h) a recombinant polypeptide of *Plasmodium ovale*; (i) a recombinant polypeptide of *Plasmodium malariae*; (j) a recombinant polypeptide of breast cancer cells; (k) a recombinant polypeptide of kidney cancer cells; (l) a recombinant polypeptide of prostate cancer cells; (m) a recombinant polypeptide of skin cancer cells; (n) a recombinant polypeptide of brain cancer cells; (o) a recombinant polypeptide of leukemia cells; (p) a recombinant profiling; (q) a recombinant polypeptide of bee sting allergy; (r) a recombinant polypeptide of nut allergy; (s) a recombinant polypeptide of pollen; (t) a recombinant polypeptide of house-dust; (u) a recombinant polypeptide of cat or cat hair allergy; (v) a recombinant protein of food allergies; (w) a recombinant protein of asthma; (x) a recombinant protein of *Chlamydia*; and (y) a fragment of any of the proteins set out in (a) (x).

In a further embodiment of the invention, the antigen or antigenic determinant is a polypeptide, a polyprotein, a peptide, an epitope or a polyepitope of HIV. Said polypeptide, polyprotein, peptide, epitope or polyepitope of HIV is fused, coupled, bound or otherwise attached to the VLP 6r packaged VLP as set out throughout the present application, and leading to preferred embodiments of the invention.

HIV is a retrovirus and belongs to the family of the lentiviruses. Two types of HIV viruses have been discovered, HIV-1 and HIV-2. HIV-2 is mainly found in the countries of Western Africa, while HIV-1 is the most common form of HIV elsewhere.

The overall structure of the HIV virus as well as of a number of its components are well known, although no crystal structure of the whole virus is available yet (Turner, B. G. et al., J. Mol. Biol. 285: 1-32 (1999)). There is strong evidence for a central role of HIV specific T-cells in controlling HIV viral replication (Jin X., et al., J. Exp. Med. 189: 1365-1372 (1999)). There have been numerous attempts to develop vaccination strategies eliciting T-cell responses against HIV, and in particular cytotoxic T-cell (CTL) responses. Those approaches have so far worked nicely in murine and non-human primate models, but are significantly less effective in humans (Moingeon P. et al., J. Biotechnol. 98: 189-198 (2002)). DNA vaccination, use of non replicating adenoviral vector (Shiver, J. W. et al., Nature 415:331-335 (2002)), or live attenuated viruses (Hanke, T. et al., Nat. Med. 6: 951-955 (2000)) have been described. Combination of two of those approaches in a so called prime boost regimen has also been described (Allen, T. M. et al., J. Immunol. 164: 4968-4978 (2000)). These approaches however suffer from a number of disadvantages. DNA immunisation may lead to integration of DNA into the genome, plasmid DNA may contain resistance genes, viral promoters are used, and antibodies to DNA may be elicited in the host. Furthermore, large amounts of DNA are required. The use of live attenuated or replication deficient viruses always bears the risk of recombination, which might lead to more virulent species, which is a concern particularly in immunocompromised individuals. The use of viral vectors is expected to lead to the infection of a large number of different cell types in the body, and indeed infection is required for the efficacy of the vaccine. Finally, the use of adenoviral vectors may be inefficient or lead to side effects in patients sero-positive for adenovirus. There is therefore a need for a safe and immunogenic vaccine technology to induce strong and potent CTL responses against HIV.

Therefore, a further aspect of the present invention and a preferred embodiment of the present invention is to provide a composition for enhancing an immune response in an animal comprising: (a) a virus-like particle; (b) an immunostimulatory substance; and (c) at least one antigen or antigenic determinant; wherein said immunostimulatory substance is bound to said virus-like particle, and wherein said antigen comprises, alternatively consists essentially of, or alternatively consists of at least one HIV polypeptide, and wherein said at least one HIV polypeptide is bound to said virus-like particle.

A "HIV polypeptide" as used herein shall include a polypeptide, a polyprotein, a peptide, an epitope of HIV. In a preferred embodiment of the present invention the term "HIV polypeptide" as used herein shall refer to a polypeptide of HIV comprising, or alternatively consisting essentially of, or alternatively consisting of an epitope of HIV. In a further preferred embodiment of the present invention, the antigen or antigenic determinant comprises, or alternatively consists essentially of, or alternatively consists of a polyepitope of HIV. The term "polyepitope of HIV" as used herein shall refer to a combination of at least two HIV polypeptides, wherein said at least two HIV polypeptides are bound directly or by way of a linking sequence.

In a very preferred embodiment of the present invention the antigen comprises, or alternatively consists essentially of, or alternatively consists of is a combination of at least two HIV polypeptides, wherein said at least two HIV polypeptides are bound directly or by way of a linking sequence.

VLPs bound, coupled, or otherwise fused to HIV antigens are particularly suited as a safe, non-infectious and non-replicative vaccine to induce T-cells and in particular CTLs against HIV. VLPs are particularly effective when they are packaged with immunostimulatory substances and sequences, respectively. The use of a defined vaccine and thus defined doses of antigen is another advantage over the use of viral vectors, where the antigen dose is more difficult to evaluate. Finally, VLPs target preferentially dendritic cells and macrophages (Ruedl, C. et al., Eur. J. Immunol. 32: 818-825 (2002)), ensuring antigen delivery to the most relevant antigen presenting cells. VLP based vaccines have therefore a much higher specificity than viral-vector or DNA based vaccines.

Suitable HV antigens and poylpetides, respectively, for preparation of the compositions of the invention include the following HIV protein subunits: p17-GAG, p24-GAG, p15-GAG, Protease, reverse transcriptase (RT), Integrase, Vif, Vpr, Vpu, Tat, Rev, gp-41-Env, gp-120-Env and Nef (Addo, M. M. et al., J. Virol. 77: 2081-2092 (2003)). Both the whole protein subunits and fragments thereof are suitable in preparing the compositions of the invention. In particular, chemically synthesized peptides having the sequence of fragments of these subunits are also included. Polyepitopes, which may be obtained as recombinant polypeptides or as chemically synthesized long peptides, are used in a favored embodiment of the invention for binding, coupling or otherwise attachment to the VLP and preferably packaged VLP. The DNA sequence encoding a polyepitope may also be fused in frame to the sequence of a VLP subunit, leading to VLPs or packaged VLPs fused to the polyepitope. In the case where the HIV antigen is coupled to the VLP using a cross-linker containing a maleimide moiety, the HIV antigen, a peptide or recombinant polypeptide, is modified according to the disclosures of the invention to include a cysteine residue for reaction with the maleimide moiety introduced in the VLP after the derivatization step of the cross-linking procedure.

A prominent feature of HIV infection, is the ability of the virus to escape from immune control, through accumulation of mutations which are selected for by the strong CTL response elicited in the host (McMichael, A. J. & Rowland-Jones, S. L. Nature 410: 980-987 (2001)). It is therefore advantageous to immunize and induce T-cells against a diversity of epitopes, in order to limit the effect of mutations in single epitopes. A composition of the invention suitable for eliciting a T-cell response against a plurality of epitope will for example be prepared by coupling at least two, or alternatively a plurality of epitopes, in the form of chemically synthesized peptides modified accordingly for cross-linking, to a VLP or packaged VLP. As a result, VLPs or packaged VLPs each coupled to at least two, or alternatively several different HIV polypeptides and therefore epitopes are obtained. In another approach, a peptide and polypeptide, respectively, containing at least two, or alternatively several consecutive HIV epitopes either originating from the same or from different HIV antigens, i.e. a preferred polyepitope of HIV for the present invention, is coupled, bound, fused or otherwise attached to a VLP or packaged VLP. Likewise, at least two, or alternatively several different polyepitopes may also be coupled, fused or otherwise attached to one VLP or packaged VLP. In yet another embodiment of the invention, at least two, or alternatively several different HIV antigens, in the form of recombinant polypeptides, are coupled or bound to one VLP or packaged VLP. Alternatively, a polyprotein, that is a fusion protein comprising two or more HIV polypeptides, modified according to the disclosures of the present invention for coupling, binding or fusion to a VLP, is used as antigen or antigenic determinant. In a further embodiment, combination of peptides, polyepitopes and recombinant polypeptides are coupled, bound or otherwise attached to one VLP or packaged VLP. In a yet further embodiment of the invention, the HIV antigens are fused to one VLP or packaged VLP.

Immunisation of an animal or subject with a plurality of HIV antigens is also achieved in one further embodiment of the invention by mixing different particles, each coupled, bound, fused or otherwise attached to one, two or more HIV antigens, said HIV antigens being a peptide, an epitope a recombinant polypeptide or a polyepitope.

As HIV virus is constantly mutating, it has been recognized that the sequence of the antigens of a given HIV primary isolate may be more remote in sequence identity from the sequences of so called autologuous viruses present in a given population, than a consensus sequence built from the sequences available in the database (The Identification of Optimal HIV-Derived CTL Epitopes in Diverse Populations Using HIV Clade-Specific Consensus, pp. I-1-20 in HIV Molecular Immunology 2001. Edited by: Korber B T K, Brander C, Haynes B F, Koup R, Kuiken C, Moore J P, Walker B D, and Watkins D. Published by: Theoretical Biology and Biophysics Group, Los Alamos National Laboratory, Los Alamos, N. Mex., LA-UR 02-2877). The sequences of epitopes to be coupled, fused, bound or otherwise attached to a VLP or packaged VLP as peptide, polyepitope or included in a recombinant polypeptide or polyprotein are therefore preferably consensus sequences, obtained from the database (see above reference, or website: http://hiv-web.lanl.gov/seq-db.html) or obtained by aligning all sequences of a given antigen from the database. In preferred embodiments, sequences from one lade of virus are selected, in function of the most prevalent lade in the geographical region where the compositions of the invention or vaccines are intended to be injected. Aligning sequences of the database would be known to one skilled in the art. For example, the program Blast (Altschul, S. F et al., J. Mol. Biol. 215:403-410 (1990); Altschul, S. F. et al., Nature Genet. 6:119-129 (1994)) or FASTA (Pearson, W. R. Methods Enzymol. 183:63-98 (1990)) may be used to perform the sequence alignments.

The HIV antigens p24-GAG and Nef have been found to have the highest epitope density (Addo, M. M. et al., J. Virol. 77: 2081-2092 (2003)). In preferred embodiments of the invention, the antigen or antigenic determinant comprises therefore p24-GAG-CTL and/or NEF-CTL and/or Th cell epitopes. Th cell epitopes are believed to contribute to the induction and maintenance of CTL responses, and therefore, in preferred embodiments of the invention, Th cell epitopes are included in the composition of the invention. For example, Th cell epitopes may be included in a polyepitope or polyprotein. Alternatively, peptides comprising Th cell epitopes may be coupled to VLPs or packaged VLPs, or the composition of the invention may be a mixture of particles, each coupled to an individual peptide, and one or more of said peptides may comprise one or more Th cell epitopes.

In very preferred embodiments of the invention, the antigen or antigenic determinant with the second attachment site is selected from the group of the GAG polyepitopes gag-G50 (SEQ ID NO: 86), gag-G68n (SEQ ID NO: 88) and of the Nef polyepitope nef-N56 (SEQ ID NO: 87). Gag-50, gag-68n and nef-N56 comprise polyepitopes derived from the Clade B consensus sequences of gag and nef (The Identification of Optimal HIV-Derived CTL Epitopes in Diverse Populations Using HIV Clade-Specific Consensus, pp. I-1-20 in HIV Molecular Immunology 2001. Edited by: Korber B T K, Brander C, Haynes B F, Koup R, Kuiken C, Moore J P, Walker B D, and Watkins D. Published by: Theoretical Biology and Biophysics Group, Los Alamos National Laboratory, Los Alamos, N. Mex., LA-UR 02-2877; online database on HIV epitopes and consensus sequence, http://hiv-web.lanl.gov/seq-db.html).

The nef-N56 polyepitope, starting with the amino acid number 66 of the Nef-protein consensus sequence (SEQ ID NO: 96), comprises amino acids 66-99 (VGFPVRPQVPL-RPMTYKAAVDLSHFLKEKGGLEG, (SEQ ID NO: 98), followed by amino acids 131-150 (PGIRYPLTFG-WCFKLVPVEP, (SEQ ID NO: 99) of the HIV-1 clade B Nef-protein consensus sequence (SEQ ID NO: 96). The resulting polypeptide, i.e. the combination of SEQ ID NO: 98 and SEQ ID NO: 99, has the amino acid sequence of SEQ ID NO: 104. The nef-N56 polyepitope additionally comprises an N-terminal Cysteine and Glycine for coupling (SEQ ID NO: 87).

The gag-G50 polyepitope starts at the N-terminus of p24-GAG, from position 139 of the HIV-1 clade B GAG-protein consensus sequence (SEQ ID NO: 97). The sequence "KVVEE" ((SEQ ID NO: 100) which represents the amino acids 157-161 from the GAG consensus sequence (SEQ ID NO: 97)), and where the density of epitopes is lowest, is deleted. Thus, gag-G50 comprises amino acids 139-156 (QGQMVHQAISPRTLNAWV, (SEQ ID NO: 101)), followed by amino acids 162-191 (KAFSPEVIPMFSALSEG-ATPQDLNTMLNTV (SEQ ID NO: 102)) of the GAG-protein consensus sequence (SEQ ID NO: 97). The resulting polypeptide, i.e. the combination of SEQ ID NO: 101 and SEQ ID NO: 102, has the amino acid sequence of SEQ ID NO: 105. In a preferred embodiment, the gag-G50 polyepitope comprises an N-terminal Cysteine for coupling (SEQ ID NO: 106). In another preferred embodiment, in particular to improve solubility, the gag-G50 polyepitope additionally comprises a C-terminal lysine residue (SEQ ID NO: 86).

The gag-G68n epitope (SEQ ID NO: 88) is based on G50 epitope, with the addition of the more C-terminal "GEI-YKRWIILGLNKIVRMY" sequence, corresponding to aminoacids 259-277 (SEQ ID NO: 103) from GAG-protein consensus sequence (SEQ ID NO: 97) to the N-terminus of the sequence of gag-G50 (excluding the N-terminal cysteine). Therefore, the resulting HIV polypeptide, i.e. the combination of SEQ ID NO: 103, SEQ ID NO: 101 and SEQ ID NO: 102, has the amino acid sequence of SEQ ID NO: 172. In a preferred embodiment, the gag-G68n epitope comprises an N-terminal Cysteine for coupling (SEQ ID NO: 108). In another preferred embodiment, in particular to improve solubility, the gag-G68n epitope additionally comprises a C-terminal lysine residue (SEQ ID NO: 88).

In a preferred embodiment, the polyepitopes of the invention comprise a cysteine residue at the N-terminus for coupling, rather than a C-terminal cysteine, since there are more protecting strategies for N-terminal cysteines, and peptides may be further trimmed at their N-terminus for proper presentation by aminopeptidases (Goldberg A. L. et al., Mol. Immunol. 39: 147-164 (2002)). Introduction of the cysteine residue for coupling to the C-terminus rather than the N-terminus however also leads to an embodiment of this invention.

In further preferred embodiments of the invention, the polyepitopes gag-G50 (SEQ ID NO: 86), nef-N56 (SEQ ID NO: 87) or gag-G68n (SEQ ID NO: 88) are coupled to the RNA phage VLPs or packaged VLPs Qβ, AP205, GA, MS-2 and fr, or to HBcAg VLPs or packaged VLPs modified to harbour an additional lysine residue in their immunodominant region, i.e. HBcAg1-185lys described in WO 02/56905 which is incorporated hereby in its entirety by way of reference. In a further preferred embodiment of the invention, the two polyepitopes gag-G50 and nef-N56 are coupled both on a single VLP. In a yet further embodiment of the invention, the VLP is the VLP of RNA phages Qβ, AP205, GA, MS-2 and Fr, or HBcAg1-185lys being described in WO 02/56905 which is incorporated hereby in its entirety by way of reference.

In specific embodiments of the invention, the gag-G50 and gag-G68n, and the nef-N56 epitopes are fused to the N-terminus of the VLP of phage fr, or to the C-terminus of phage Qβ.

Expression and purification of the GAG protein (Berthet-Colominas, C. et al., EMBO J. 18: 1124-1136 (1999))), and the Nef protein or protein fragments (Franken, P. et al., Prot. Sci. 6: 2681-2683 (1997)) of HIV have been described, and in a further embodiment of the invention, GAG and NEF proteins, or fragments thereof, modified to include a cysteine residue for coupling according to the disclosure of the present invention, are coupled to VLPs or packaged VLPs.

The compositions of the invention comprising a polypeptide, a polyprotein, a peptide, an epitope or a polyepitope of HIV and optionally a further adjuvant, are useful as vaccines for induction of HIV specific T-cells in humans. In a preferred embodiment of the invention, the vaccine comprises a Qβ or AP205 VLP packaged with the G8-8 oligodeoxynucleotide and optionally a further adjuvant. The T-cell response induced upon vaccination is assessed in proliferation assays (for Th cell response, Belshe R. B. et al., J. Inf. Dis. 183: 1343-1352 (2001)), in ELISPOT assays (Oxenius, A. et al., Proc. Natl. Acad. Sci. USA 99: 13747-13752 (2002)), or in Cytotoxicity assays (Belshe R. B. et al., J. Inf. Dis. 183: 1343-1352 (2001)).

In a further embodiment, gag-G50, gag-G68n and nef-N56 devoid of the N-terminal cysteine are inserted between amino acid 2 and 3 (numbering of the cleaved CP, that is wherein the N-terminal methionine is cleaved) of the fr CP. In a related embodiment of the invention, gag-G50, gag-G68n and nef-N56 devoid of the N-terminal cysteine are fused to the A1 protein of Qβ VLP, as described above.

In another embodiment of the present invention, the antigen, being coupled, fused or otherwise attached to the virus-like particle, is a T cell epitope, either a cytotoxic or a Th cell epitope. In a further preferred embodiment, the antigen is a combination of at least two, preferably different, epitopes, wherein the at least two epitopes are linked directly or by way of a linking sequence. These epitopes are preferably selected from the group consisting of cytotoxic and Th cell epitopes.

It should also be understood that a mosaic virus-like particle, e.g. a virus-like particle composed of subunits attached to different antigens and epitopes, respectively, is within the scope of the present invention. Such a composition of the present invention can be, for example, obtained by transforming E. coli with two compatible plasmids encoding the subunits composing the virus-like particle fused to different antigens and epitopes, respectively. In this instance, the mosaic virus-like particle is assembled either directly in the cell or after cell lysis. Moreover, such an inventive composition can also be obtained by attaching a mixture of different antigens and epitopes, respectively, to the isolated virus-like particle.

The antigen of the present invention, and in particular the indicated epitope or epitopes, can be synthesized or recombinantly expressed and coupled to the virus-like particle, or fused to the virus-like particle using recombinant DNA techniques. Exemplary procedures describing the attachment of antigens to virus-like particles are disclosed in WO 00/32227, in WO 01/85208 and in WO 02/056905, the disclosures of which are herewith incorporated by reference in its entirety.

The invention also provides a method of producing a composition, typically and preferably for enhancing an immune response in an animal, comprising a VLP and an immunostimulatory substance, preferably an unmethylated CpG-containing oligonucleotide bound to the VLP which comprises incubating the VLP with the immunostimulatory substance and oligonucleotide, respectively, adding RNase and purifying said composition, wherein preferably the immunostimulatory substance is an unmethylated CpG-containing oligonucleotide, wherein the CpG motif of the unmethylated CpG-containing oligonucleotide is part of a palindromic sequence, and wherein the palindromic sequence is flanked at its 3'-terminus and at its 5'-terminus by less than 10 guanosine entities. Preferably, the method further comprises the step of binding an antigen or antigenic determinant to said virus-like particle. In a preferred embodiment, the anigen or antigenic determinant is bound to the virus-like particle before incubating the virus-like particle with the immunostimulatory substance. In another preferred embodiment, the anigen or antigenic determinant is bound to the virus-like particle after purifying the composition. In an equally preferred embodiment, the method comprises incubating the VLP with RNase, adding the immunostimulatory substance and oligonucleotide, respectively, and purifying the composition, wherein preferably the immunostimulatory substance is an unmethylated CpG-containing oligonucleotide, wherein the CpG motif of the unmethylated CpG-containing oligonucleotide is part of a palindromic sequence, and wherein the palindromic sequence is flanked at its 3'-terminus and at its 5'-terminus by less than 10 guanosine entities. Preferably, the method further comprises the step of binding an antigen or antigenic determinant to said virus-like particle. In a preferred embodiment, the anigen or antigenic determinant is bound to the virus-like particle before incubating the virus-like particle with the RNase. In another preferred embodiment, the anigen or antigenic determinant is bound to the virus-like particle after purifying the composition. In one embodiment, the VLP is produced in a bacterial expression system. In another embodiment, the RNase is RNase A.

The invention further provides a method of producing a composition for enhancing an immune response in an animal comprising a VLP bound to an immunostimulatory substance, preferably to an unmethylated CpG-containing oligonucleotide which comprises disassembling the VLP, adding the immunostimulatory substance and oligonucleotide, respectively, and reassembling the VLP, wherein preferably the immunostimulatory substance is an unmethylated CpG-containing oligonucleotide, wherein the CpG motif of the unmethylated CpG-containing oligonucleotide is part of a palindromic sequence, and wherein the palindromic sequence is flanked at its 3'-terminus and at its 5'-terminus by less than 10 guanosine entities. The method can further comprise removing nucleic acids of the disassembled VLP and/or purifying the composition after reassembly. Preferably, the method further comprises the step of binding an antigen or antigenic determinant to the virus-like particle. In a preferred embodiment, the anigen or antigenic determinant is bound to the virus-like particle before disassembling the virus-like particle. In another preferred embodiment, the anigen or antigenic determinant is bound to the virus-like particle after reassembling the virus-like particle and preferably after purifying the composition.

The invention also provides vaccine compositions which can be used for preventing and/or attenuating diseases or conditions. Vaccine compositions of the invention comprise, or alternatively consist of, an immunologically effective amount of the inventive immune enhancing composition together with a pharmaceutically acceptable diluent, carrier or excipient. The vaccine can also optionally comprise an adjuvant.

Thus, in a preferred embodiment, the invention provides a vaccine comprising an immunologically effective amount of the inventive immune response enhancing composition together with a pharmaceutically acceptable diluent, carrier or excipient, wherein the composition comprises, (a) a virus-like particle; (b) at least one immunostimulatory substance; and (c) at least one antigen or antigenic determinant; wherein the antigen or antigenic determinant is bound to the virus-like particle, and wherein the immunostimulatory substance is bound to the virus-like particle, and wherein the antigen comprises, alternatively consists essentially of, or alternatively consists of a human melanoma MelanA peptide analogue. Preferably, the vaccine further comprises an adjuvant.

The invention further provides vaccination methods for preventing and/or attenuating diseases or conditions in animals. In one embodiment, the invention provides vaccines for the prevention of infectious diseases in a wide range of animal species, particularly mammalian species such as human, monkey, cow, dog, cat, horse, pig, etc. Vaccines can be designed to treat infections of viral etiology such as HIV, influenza, Herpes, viral hepatitis, Epstein Bar, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

In another embodiment, the invention provides vaccines for the prevention of cancer in a wide range of species, particularly mammalian species such as human, monkey, cow, dog, cat, horse, pig, etc. Vaccines can be designed to treat all types of cancer including, but not limited to, lymphomas, carcinomas, sarcomas and melanomas.

It is well known that homologous prime-boost vaccination strategies with proteins or viruses are most often unsuccessful. Preexisting antibodies, upon re-encountering the antigen, are thought to interfere with the induction of a memory response. To our surprise, the RNA-phage derived VLPs, in particular the VLP derived from Qβ, do very efficiently induce a memory CD8$^+$ T cell response in a homologous prime-boost vaccination scheme. In contrast, as described in Example 29, live vaccinia virus immunizations are very ineffective for the induction of a primary CD8$^+$ T cell response and homologous boosting with vaccinia does hardly lead to an expansion of memory CD8$^+$ T cells.

Therefore, in a further aspect, the invention provides a method of immunizing or treating an animal comprising priming a T cell response in the animal by administering an immunologically effective amount of the inventive vaccine. Preferably, the method further comprises the step of boosting the immune response in the animal, wherein preferably the boosting is effected by administering an immunologically effective amount of a vaccine of the invention or an immunologically effective amount of a heterologous vaccine, wherein even more preferably the heterologous vaccine is a DNA vaccine, peptide vaccine, recombinant virus or a dendritic cell vaccine.

Moreover, in again another aspect, the invention further provides a method of immunizing or treating an animal comprising the steps of priming a T cell response in the animal, and boosting a T cell response in the animal, wherein the boosting is effected by administering an immunologically effective amount of the vaccine of the invention. Preferably, the primimg is effected by administering an immunologically effective amount of a vaccine of the invention or an immunologically effective amount of a heterologous vaccine, wherein even more preferably said heterologous vaccine is a DNA vaccine, peptide vaccine, recombinant virus or a dendritic cell vaccine.

Moreover, in again another aspect, the invention further provides for a composition comprising a virus-like particle, at least one immunostimulatory substance; and at least one antigen or antigenic determinant; wherein said antigen or antigenic determinant is bound to said virus-like particle, and wherein said immunostimulatory substance is bound to said virus-like particle, and wherein said antigen comprises a cytotoxic T cell epitope, a Th cell epitope or a combination of at least two of said epitopes, wherein said at least two epitopes are bound directly or by way of a linking sequence, and wherein preferably said cytotoxic T cell epitope is a viral or a tumor cytotoxic T cell epitope.

In again a further aspect, the present invention provides a composition, typically and preferably for enhancing an immune response in an animal comprising: (a) a virus-like particle; (b) an immunostimulatory substance; wherein said immunostimulatory substance (b) is bound to said virus-like particle (a); and (c) an antigen, wherein said antigen is mixed with said virus-like particle (a), and wherein said immunostimulatory substance is an unmethylated CpG-containing oligonucleotide, wherein the CpG motif of said unmethylated CpG-containing oligonucleotide is part of a palindromic sequence, and wherein said palindromic sequence is flanked at its 3'-terminus and at its 5'-terminus by less than 10 guanosine entities. As used herein, the term "mixed" refers to the combination of two or more substances, ingredients, or elements that are added together, are not chemically combined with each other and are capable of being separated. Methods of mixing antigens with virus-like particles are described in WO 04/000351, which is incorporated herein by reference in its entirety.

As would be understood by one of ordinary skill in the art, when compositions of the invention are administered to an animal, they can be in a composition which contains salts, buffers, adjuvants or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1990)).

Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS 21, QS 18, CRL1005, Aluminum salts, MF 59, and Virosomal adjuvant technology. The adjuvants can also comprise a mixture of these substances.

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention can be administered by various methods known in the art. The particular mode selected will depend of course, upon the particular composition selected, the severity of the condition being treated and the dosage required for therapeutic efficacy. The methods of the invention, generally speaking, can be practiced using any mode of administration that is medically acceptable, meaning any mode that produces effective levels of the active compounds without causing clinically unacceptable adverse effects. Such modes of administration include oral, rectal, parenteral, intracistemal, intravaginal, intraperitoneal, topical (as by powders, ointments, drops or transdermal patch), bucal, or as an oral or nasal spray. The term "parenteral" as used herein refers to modes of administration which include intravenous, intramuscular, intraperitoneal, intrasternal, subcutaneous and intraarticular injection and infusion. The composition of the invention can also be injected directly in a lymph node.

Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Combinations can be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Dosage levels depend on the mode of administration, the nature of the subject, and the quality of the carrier/adjuvant formulation. Typical amounts are in the range of about 0.1 µg to about 20 mg per subject. Preferred amounts are at least about 1 µg to about 1 mg, more preferably at least about 10 to about 400 µg per subject. Multiple administration to immunize the subject is preferred, and protocols are those standard in the art adapted to the subject in question.

The compositions can conveniently be presented in unit dosage form and can be prepared by any of the methods well-known in the art of pharmacy. Methods include the step of bringing the compositions of the invention into association with a carrier which constitutes one or more accessory ingredients. In general, the compositions are prepared by uniformly and intimately bringing the compositions of the invention into association with a liquid carrier, a finely divided solid carrier, or both, and then, if necessary, shaping the product.

Compositions suitable for oral administration can be presented as discrete units, such as capsules, tablets or lozenges, each containing a predetermined amount of the compositions of the invention. Other compositions include suspensions in aqueous liquids or non-aqueous liquids such as a syrup, an elixir or an emulsion.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art.

Other embodiments of the invention include processes for the production of the compositions of the invention and methods of medical treatment for cancer and allergies using said compositions.

Further aspects and embodiments of the present invention will become apparent in the following examples and the appended claims.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference in their entirety.

EXAMPLE 1

Generation of p33-HBcAg VLPs.

The DNA sequence of HBcAg containing peptide p33 from LCMV is given in SEQ ID NO: 15. The p33-HBcAg VLPs were generated as follows: Hepatitis B clone pEco63 containing the complete viral genome of Hepatitis B virus was purchased from ATCC. The gene encoding HBcAg was introduced into the EcoRI/HindIII restriction sites of expression vector pkk223.3 (Pharmacia) under the control of a strong tac promoter. The p33 peptide (KAVYNFATM) (SEQ ID NO: 82) derived from lymphocytic choriomeningitis virus (LCMV) was fused to the C-terminus of HBcAg (1-185) via a three leucine-linker by standard PCR methods. A clone of $E.$ $coli$ K802 selected for good expression was transfected with the plasmid, and cells were grown and resuspended in 5 ml lysis buffer (10 mM Na2HPO4, 30 mM NaCl, 10 mM EDTA, 0.25% Tween-20, pH 7.0). 200 µl of lysozyme solution (20 mg/ml) was added. After sonication, 4 µl Benzonase and 10 mM MgCl2 was added and the suspension was incubation for 30 minutes at RT, centrifuged for 15 minutes at 15,000 rpm at 4° C. and the supernatant was retained.

Next, 20% (w/v) (0.2 g/ml lysate) ammonium sulfate was added to the supernatant. After incubation for 30 minutes on ice and centrifugation for 15 minutes at 20,000 rpm at 4° C. the supernatant was discarded and the pellet resuspended in 2-3 ml PBS. 20 ml of the PBS-solution was loaded onto a Sephacryl S-400 gel filtration column (Amersham Pharmacia Biotechnology AG), fractions were loaded onto a SDS-Page gel and fractions with purified p33-VLP capsids were pooled. Pooled fractions were loaded onto a Hydroxyapatite column. Flow through (which contains purified p33-VLP capsids) was collected and loaded onto a reducing SDS-PAGE gel for monomer molecular weight analysis. Electron microscopy was performed according to standard protocols.

Thus, the structure of the p33-VLPs was assessed by electron microscopy and SDS PAGE. Recombinantly produced HBcAg wild-type VLPs (composed of HBcAg [aa 1-185] monomers) and p33-VLPs were loaded onto a Sephacryl S-400 gel filtration column (Amersham Pharmacia Biotechnology AG) for purification. Pooled fractions were loaded onto a Hydroxyapatite column. Flow through (which contains purified p33-VLPs) was collected and loaded onto a reducing SDS-PAGE gel for monomer molecular weight analysis.

Throughout the description the terms p33-HBcAg VLP, HBcAg-p33 VLP, p33-VLPs and HBc33 are used interchangeably.

EXAMPLE 2

Cloning, Expression and Purification of GA VLP

The cDNA of GA phage coat protein was amplified from GA phage by reverse transcription followed by a PCR amplification step, using the RevertAid First strand cDNA synthesis Kit (Fermentas). The cDNA was cut with the enzymes NcoI and HindIII, and cloned in vector pQβ185 previously cut with the same enzymes, leading to plasmid 355.24, harboring GA cDNA. The sequence of the inserted cDNA was checked by DNA sequencing.

Plasmid 355.24 was transformed in *E. coli* JM109. Expression was performed essentially as described for Qβ VLP. A single colony was inoculated in LB medium containing 20 mg/L Ampicillin overnight without shaking. This inoculum was transferred the next day into a larger flask containing M9 medium supplemented with 1% casaminoacids, 0.2% glucose and 20 mg/L Ampicillin, and incubated under shaking for 14-20 h.

GA VLP was isolated essentially as described for Qβ VLP. Cells were lysed, and the cleared lysate was loaded onto a Sepharose CL-4B column (Amersham Pharmacia). The eluate was concentrated by ammonium sulphate precipitation, and rechromatographed onto a Sepharose CL-6B column (Amersham Pharmacia). The final step was either an ultracentrifugation on sucrose gradient (20-50% w/v), or on CsCl. The isolated VLPs were subsequently dialysed against 20 mM Tris, 150 mM NaCl, pH 8.0.

EXAMPLE 3

Fluorescein Labeled CpG-Containing Oligonucleotides can be Packaged into BKV VLPs.

VLPs produced in yeast contain small amounts of RNA which can be easily digested and so eliminated by incubating the VLPs with RNase A. The highly active RNase A enzyme has a molecular weight of about 14 kDa and is small enough to enter the VLPs to eliminate the undesired ribonucleic acids. Recombinantly produced BKV VLPs (SEQ ID NO: 12) were concentrated to 1 mg/ml in PBS buffer pH7.2 and incubated in the absence or presence of RNase A (200 µg/ml, Roche Diagnostics Ltd, Switzerland) for 3 h at 37° C. After RNase A digestion BKV VLPs are supplemented with 75 nmol/ml 5'-fluorescein labeled phosphorothioate G8-8-FAM oligonucleotide (oligonucleotide from SEQ ID NO: 7) and incubated for 3 h at 37° C. Subsequently BKV VLPs are subjected to DNaseI digestion for 3 h at 37° C. (40 u/ml AMPD1, Sigma, Division of Fluka AG, Switzerland) or loaded without DNaseI digestion. The samples were complemented with 6-fold concentrated DNA-loading buffer (10 mM Tris pH7.5, 10% v/v glycerol, 0.4% orange G) and run for 1 h at 65 volts in a 0.8% native tris-acetate pH 7.5 agarose gel.

BKV VLPs (15 µg) was analyzed by a native 0.8% agarose gel electrophoresis after control incubation or after digestion with RNase A and subsequent incubation with CpG-oligonucleotides (with phosphate- or with phosphorothioate (pt) backbone) upon staining with ethidium bromide or Coomassie Blue.

EXAMPLE 4

CpG-Containing Oligonucleotides can be Packaged into BKV VLPs.

To introduce immunostimulatory CpG-oligonucleotides, the RNase A treated recombinant BKV VLPs (Example 3) are supplemented with 150 nmol/ml G8-8 oligonucleotides with phosphodiester backbone or G8-8 with phosphorothioate backbone and incubated for 3 h at 37° C. VLP preparations for mouse immunization are extensively dialysed (10,000-fold diluted) for 24 h against PBS pH7.2 with a 300 kDa MWCO dialysis membrane (Spectrum Medical industries Inc., Houston, USA) to eliminate RNase A and the excess of CpG-oligonucleotides. The samples are complemented with 6-fold concentrated DNA-loading buffer (10 mM Tris pH7.5, 10% v/v glycerol, 0.4% orange G) and run for 1 h at 65 volts in a 0.8% native tris-acetate pH7.5 agarose gel. BKV VLPs (15 µg) are loaded on a native 0.8% agarose gel electrophoresis and analyzed after control incubation or after digestion with RNase A and subsequent incubation with G8-8-oligonucleotides (with phosphodiester- or with phosphorothioate backbone) upon staining with ethidium bromide or Coomassie Blue in order to assess the presence of RNA/DNA or protein and the reduction of unbound CpG-oligonucleotides after dialysis.

EXAMPLE 5

Immunostimulatory Nucleic Acids can be Packaged into HBcAg VLPs Comprising Fusion Proteins with Antigens.

HBcAg VLPs, when produced in *E. coli* by expressing the Hepatitis B core antigen fusion protein p33-HBcAg (HBc33) (see Example 1) or the fusion protein to the peptide P1A (HBcP1A), contain RNA which can be digested and so eliminated by incubating the VLPs with RNase A.

The gene P1A codes for a protein that is expressed by the mastocytoma tumor cell line P815. The dominant CTL epitope, termed P1A peptide, binds to MHC class I (Ld) and the complex is recognized by specific CTL clones (Brändle et al., 1998, Eur. J. Immunol. 28: 4010-4019). Fusion of peptide P1A-1 (LPYLGWLVF) ((SEQ ID NO: 95) to the C-terminus of HBcAg (aa 185, see Example 1) was performed by PCR using appropriate primers using standard molecular biology techniques. A three leucine linker was cloned between the HBcAg and the peptide sequence. Expression was performed as described in Example 1. The fusion protein of HBcAg with P1A, termed HBcP1A, formed capsids when expressed in *E. coli* which could be purified similar to the procedure described in Example 1.

Enzymatic RNA hydrolysis: Recombinantly produced HBcAg-p33 (HBc33) and HBcAg-P1A (HBCP1A) VLPs at a concentration of 1.0 mg/ml in 1×PBS buffer (KCl 0.2 g/L, KH2PO4 0.2 g/L, NaCl 8 g/L, Na2HPO4 1.15 g/L) pH 7.4, were incubated in the presence of 300 µg/ml RNase A (Qiagen AG, Switzerland) for 3 h at 37° C. in a thermomixer at 650 rpm.

Packaging of immunostimulatory nucleic acids: After RNA digestion with RNAse A HBcAg-p33 VLPs are supplemented with 130 nmol/ml CpG-oligonucleotides G3-6, G6 and G8-8 (Table 1). The resulting plasmid, produced in *E. coli* XL 1-blue and isolated using the Qiagen Endofree plasmid Giga Kit, is digested with restriction endonucleases XhoI and XbaI and resulting restriction products are separated by agarose electrophoresis. Inserts are isolated by electro-elution and ethanol precipitation. Sequences are verified by sequencing of both strands.

DNAse I treatment: Packaged HBcAg-p33 VLPs are subsequently subjected to DNaseI digestion (5 U/ml) for 3 h at 37° C. (DNaseI, RNase free Fluka AG, Switzerland) and were extensively dialysed (2× against 200-fold volume) for 24 h against PBS pH 7.4 with a 300 kDa MWCO dialysis membrane (Spectrum Medical industries Inc., Houston, USA) to eliminate RNAse A and the excess of CpG-oligonucleotides.

Benzonase treatment: Since some single stranded oligodeoxynucleotides are partially resistant to DNaseI treatment, Benzonase treatment is used to eliminate free oligonucleotides from the preparation. 100-120 U/ml Benzonase (Merck KGaA, Darmstadt, Germany) and 5 mM MgCl2 are added and incubated for 3 h at 37° C. before dialysis.

Dialysis: VLP preparations packaged with immunostimulatroy nucleic acids used in mouse immunization experiments are extensively dialysed (2× against 200fold volume) for 24 h against PBS pH 7.4 with a 300 kDa MWCO dialysis membrane (Spectrum Medical Industries, Houston, US) to eliminate added enzymes and free nucleic acids.

Analytics of packaging: release of packaged immunostimulatory nucleic acids: To 50 μl capsid solution 1 μl of proteinase K (600 U/ml, Roche, Mannheim, Germany), 3 μl 10% SDS-solution and 6 μl 10fold proteinase buffer (0.5 M NaCl, 50 mM EDTA, 0.1 M Tris pH 7.4) are added and subsequently incubated overnight at 37° C. VLPs are completed hydrolysed under these conditions. Proteinase K was inactivated by heating for 20 min at 65° C. 1 μl RNAse A (Qiagen, 100 μg/ml, diluted 250 fold) was added to 25 μl of capsid. 2-30 μg of capsid were mixed with 1 volume of 2× loading buffer (1×TBE, 42% w/v urea, 12% w/v Ficoll, 0.01% Bromphenolblue), heated for 3 min at 95° C. and loaded on a 10% (for oligonucleotides of about 20 nt length) or 15% (for>than 40 mer nucleic acids) TBE/urea polyacrylamid gel (Invitrogen). Alternatively samples are loaded on a 1% agarose gel with 6× loading dye (10 mM Tris pH 7.5, 50 mM EDTA, 10% v/v glycerol, 0.4% orange G). TBE/urea gels are stained with SYBRGold and agarose gels with stained with ethidium bromide.

EXAMPLE 6

Immunostimulatory Nucleic Acids can be Packaged in HBcAg-wt Coupled with Antigens.

Recombinantly produced HBcAg-wt VLPs were packaged after coupling with peptide p33 (CGG-KAVYNFATM) (SEQ ID NO: 83), derived from lymphocytic choriomeningitis virus (LCMV). For coupling HBcAg-wt VLPs (2 mg/ml) were derivatized with 25× molar excess of SMPH (Succinimidyl-6-[(β-maleimido-propionamido)hexanoate], Pierce) for 1 h at 25° C. in a thermomixer. The derivatized VLPs were dialyzed to Mes buffer (2-(N-morpholino) ethanesulphonic acid) pH 7.4 for 2×2 h using MWCO 10.000 kD dialysis membranes at 4° C. VLPs (50 μM) were subsequently coupled to the N-terminal cysteine of the p33 peptide (250 μM) during a 2 h incubation in a thermomixer at 25° C. Samples were dialyzed (MWCO 300.000) extensively to 1×PBS pH 7.4 to eliminate undesired free peptide.

HBcAg-wt VLPs derivatization with SMPH and coupling to p33 peptide was analyzed on SDS-PAGE. Samples were analysed by 16% SDS PAGE and stained with Coomassie Blue. Loaded on the gel were the following samples: 1. NEB Prestained Protein Marker, Broad Range (#7708S), 10 μl; 2. p33 peptide; 3. HBcAg-wt VLP derivatized with SMPH, before dialysis; 4. HBcAg-wt VLP derivatized with SMPH, after dialysis; 5. HBcAg-wt VLP coupled with p33, supernatant; 6. HBcAg-wt VLP coupled with p33, pellet. HBcAg-wt was visible as a 21 kD protein band. Due to the low molecular weigth of SMPH is the derivatised product only slightly larger and can not be distinguished by SDS-PAGE. Peptide alone was visible as a 3 kD band and coupled product, termed HBx33, showed a strong secondary band at approximately 24 kD accounting for more than 50% of total HBcAg-wt.

Enzymatic RNA hydrolysis: HBx33 VLPs (0.5-1.0 mg/ml, 1×PBS buffer pH7.4) in the presence of RNase A (300 μg/ml, Qiagen AG, Switzerland) were diluted with 4 volumes H2O to decrease salt concentration to a final 0.2×PBS concentration and incubated for 3 h at 37° C. in a thermomixer at 650 rpm.

Packaging of immunostimulatory nucleic acids: After RNase A digestion HBx33 VLPs are concentrated using Millipore Microcon or Centriplus concentrators, then supplemented with 130 nmol/ml G3-6, G6 or G8-8 (Table 1) and incubated in a thermomixer for 3 h at 37° C. in 0.2×PBS pH 7.4. Subsequently, reaction mixtures are subjected to DNaseI digestion (5 U/ml) for 3 h at 37° C. (DNaseI, RNase free Fluka AG, Switzerland). VLP preparations for mouse immunization were extensively dialysed (2× against 200-fold volume) for 24 h against PBS pH 7.4 with a 300 kDa MWCO dialysis membrane (Spectrum Medical industries Inc., Houston, USA) to eliminate RNase A and the excess of CpG-oligonucleotides.

EXAMPLE 7

Immunostimulatory Nucleic Acids can be Packaged into Qβ VLPs Coupled with Antigens.

Coupling of p33 Peptides to Qβ VLPs:

Recombinantly produced virus-like particles of the RNA-bacteriophage Qb (Qβ VLPs) were used untreated or after coupling to p33 peptides containing an N-terminal CGG or and C-terminal GGC extension (CGG-KAVYNFATM (SEQ ID NO: 83) and KAVYNFATM-GGC (SEQ ID NO: 84)). Recombinantly produced Qβ VLPs were derivatized with a 10 molar excess of SMPH (Pierce) for 0.5 h at 25° C., followed by dialysis against 20 mM HEPES, 150 mM NaCl, pH 7.2 at 4° C. to remove unreacted SMPH. Peptides were added in a 5 fold molar excess and allowed to react for 2 h in a thermomixer at 25° C. in the presence of 30% acetonitrile. The analysis of the p33 coupling to Qb VLPs was done on SDS-PAGE after Coomassie Blue staining. Loaded were the following samples: (A) 1. NEB Prestained Protein Marker, Broad Range (#7708S), 10 μl; 2. Qb VLP, 14 μg; 3. Qb VLP derivatized with SMPH, after dialysis; 4. Qb VLP coupled with CGG-p33, supernatant. (B) 1. NEB Prestained Protein Marker, Broad Range (#7708S), 10 μl; 2. Qb VLP, 10 μg; 3. Qb VLP coupled with GGC-p33, supernatant. The SDS-PAGE analysis demonstrated multiple coupling bands consisting of one, two or three peptides coupled to the Qβ monomer. For the sake of simplicity the coupling product of the peptide p33 and Qβ VLPs was termed, in particular, throughout the example section Qbx33.

Qβ VLPs, when produced in *E. coli* by expressing the bacteriophage Qβ capsid protein, contain RNA which can be digested and so eliminated by incubating the VLPs with RNase A.

Low Ionic Strength and Low Qβ Concentration Allow RNA Hydrolysis of Qβ VLPs by RNAse A:

Qβ VLPs at a concentration of 1.0 mg/ml in 20 mM Hepes/150 mM NaCl buffer (HBS) pH 7.4 were either digested directly by addition of RNase A (300 μg/ml, Qiagen AG, Switzerland) or were diluted with 4 volumes H2O to a final 0.2×HBS concentration and then incubated with RNase A (60 μg/ml, Qiagen AG, Switzerland). Incubation was allowed for 3 h at 37° C. in a thermomixer at 650 rpm. RNA hydrolysis from Qb VLPs by RNase A under low and high ionic strength was analyzed on a 1% agarose gel stained with ethidium bromide and Coomassie Blue. Loaded on the gel were the following samples: (A, B) 1. MBI Fermentas 1 kb DNA ladder; 2. Qb VLP untreated; 3. Qb VLP treated with RNase A inlx HBS buffer pH7.2. (C, D) 1. MBI Fermentas 1 kb DNA ladder; 2. Qb VLP untreated; 3. Qb VLP treated with RNase A in 0.2×HBS buffer pH7.2. It was demonstrated that in 1×HBS only a very weak reduction of RNA content was observed (FIG. 25 A), while in 0.2×HBS most of the RNA were hydrolysed. In agreement, capsid migration was unchanged after addition of RNAse A in 1×HBS, while migration was slower after addition of RNAse in 0.2×HBS.

Low Ionic Strength Increases Nucleic Acid Packaging in Qβ VLPs:

After RNase A digestion in 0.2×HBS the Qβ VLPs are concentrated to 1 mg/ml using Millipore Microcon or Centriplus concentrators and aliquots are dialysed against 1×HBS or 0.2×HBS. Qβ VLPs are supplemented with 130 nmol/ml G3-6, G6 or G8-8 (Table 1) and incubated in a thermomixer for 3 h at 37° C. Subsequently Qβ VLPs are subjected to Benzonase digestion (100 U/ml) for 3 h at 37° C. Samples are analysed on 1% agarose gels after staining with ethidium bromide or Coomassie Blue.

Different immunostimulatory nucleic acids can be packaged in Qβ and Qbx33 VLPs:

After RNase A digestion in 0.2×HBS the Qβ VLPs or Qbx33 VLPs are concentrated to 1 mg/ml using Millipore Microcon or Centriplus concentrators and supplemented with 130 nmol/ml G3-6, G6 and G8-8 (Table 1) and incubated in a thermomixer for 3 h at 37° C. Subsequently Qβ VLPs or Qbx33 VLPs are subjected to DNAse I digestion (5 U/ml) or Benzonase digestion (100 U/ml) for 3 h at 37° C. Samples are analysed on 1% agarose gels after staining with ethidium bromide or Coomassie Blue. Packaging of G3-6, G6 or G8-8 can be analyzed by release of the nucleic acid by proteinase K digestion followed by agarose electrophoresis and ethidium bromide staining.

EXAMPLE 8

AP205 Disassembly-Purification-Reassembly and Packaging of Immunostimulatory Nucleic Acids.

A. Disassembly and Reassembly of AP205 VLP from Material Able to Reassemble without Addition of Oligonucleotide Disassembly: 40 mg of lyophilized purified AP205 VLP (SEQ-ID: 80 or 81) were resolubilized in 4 ml 6 M GuHCl, and incubated overnight at 4° C. The disassembly mixture was centrifuged at 8000 rpm (Eppendorf 5810 R, in fixed angle rotor F34-6-38, used in all the following steps). The pellet was resolubilized in 7 M urea, while the supernatant was dialyzed 3 days against NET buffer (20 mM Tris-HCl, pH 7.8 with 5 mM EDTA and 150 mM NaCl) with 3 changes of buffer. Alternatively, dialysis was conducted in continuous mode over 4 days. The dialyzed solution was centrifuged at 8000 rpm for 20 minutes, and the pellet was resolubilized in 7 M urea, while the supernatant was pelletted with ammonium sulphate (60% saturation), and resolubilized in a 7 M urea buffer containing 10 mM DTT. The previous pellets all resolubilized in 7 M urea were joined, and precipitated with ammonium sulphate (60% saturation), and resolubilized in a 7 M urea buffer containing 10 mM DTT. The materials resolubilized in the 7 M urea buffer containing 10 mM DTT were joined and loaded on a Sephadex G75 column equilibrated and eluted with the 7 M urea buffer containing 10 mM DTT at 2 ml/h. One peak eluted from the column. Fractions of 3 ml were collected. The peak fractions containing AP205 coat protein were pooled and precipitated with ammonium sulphate (60% saturation). The pellet was isolated by centrifugation at 8000 rpm, for 20 minutes. It was resolubilized in 7 M urea, 10 mM DTT, and loaded on a short Sepharose 4B column (1.5×27 cm Sepharose 4B, 2 ml/h, 7 M urea, 10 mM DTT as elution buffer). Mainly one peak, with a small shoulder eluted from the column. The fractions containing the AP205 coat protein were identified by SDS-PAGE, and pooled, excluding the shoulder. This yielded a sample of 10.3 ml. The protein concentration was estimated spectrophotometrically by measuring an aliquot of protein diluted 25-fold for the measurement, using the following formula: (1.55× OD280−0.76×OD260)×volume. The average concentration was of 1 nmol/ml of VLP (2.6 mg/ml). The ratio of absorbance at 280 nm vs. 260 nm was of 0.12/0.105.

Reassembly: 1.1 ml beta-mercaptoethanol was added to the sample, and the following reassembly reactions are set up:

1 ml of AP205 coat protein, no nucleic acids 1 ml of AP205 coat protein, rRNA (approx. 200 OD260 units, 10 nmol)

9 ml of AP205 coat protein, G8-8 (370 ul of 225 pmol/μl solution, i.e. 83 nmol).

These mixtures are dialyzed 1 hour against 30 ml of NET buffer containing 10% beta-mercaptoethanol. The mixture containing no nucleic acids is dialyzed separately. The dialysis is then pursued in a continuous mode, and 1 l of NET buffer is exchanged over 3 days. The reaction mixtures were subsequently extensively dialyzed against water (5 changes of buffer), and lyophilized. They are resolubilized in water, and analyzed by electron microscope (EM). All mixtures contained capsids, showing that AP205 VLP reassembly is independent of the presence of detectable nucleic acids, as measured by agarose gel electrophoresis using ethidium bromide staining. The EM procedure is as follows: A suspension of the proteins was absorbed on carbon-formvar coated grids and stained with 2% phosphotungstic acid (pH 6, 8). The grids were examined with a JEM 100C (JEOL, Japan) electron microscope at an accelerating voltage of 80 kV. Photographic records (negatives) are performed on Kodak electron image film and electron micrographs were obtained by printing of negatives on Kodak Polymax paper. The VLP reassembled in the presence of the G8-8 is purified over a Sepharose 4B column (1×50 cm), eluted with NET buffer (1 ml/h). The fractions are analyzed by Ouchterlony assay, and the fractions containing VLP are pooled. Samples of the reassembly reaction containing G8-8 taken after the reassembly step and before extensive dialysis are analysed on a 0.6% agarose gel stained with ethidium-bromide and Coomassie blue.

B. Reassembly of AP205 VLP using Disassembled Material which does not Reassemble in the Absence of Added oligonucleotide Disassembly: 100 mg of purified and dried recombinant AP205 VLP are used for disassembly as described above. All steps are performed essentially as described under disassembly in part A, but for the use of 8 M urea to solublize the pellets of the ammonium sulphate precipitation steps and the omission of the gel filtration step using a CL-4B column prior to reassembly. The pooled fractions of the Sephadex G-75 column containe 21 mg of protein as determined by spectroscopy using the formula described in part A. The ratio of absorbance at 280 nm to the absorbance at 260 nm of the sample is of 0.16 to 0.125. The sample is diluted 50 times for the measurement.

Reassembly: The protein preparation resulting from the Sephadex G-75 gel filtration purification step is precipitated with ammonium sulphate at 60% saturation, and the resulting pellet solubilized in 2 ml 7 M urea, 10 mM DTT. The sample is diluted with 8 ml of 10% 2-mercaptoethanol in NET buffer, and dialyzed for 1 hour against 40 ml of 10% 2-mercaptoethanol in NET buffer. Reassembly is initiated by adding 0.4 ml of a G8-8 solution (109 nmol/ml) to the protein sample in the dialysis bag. Dialysis in continous mode is set up, and NET buffer used as eluting buffer. Dialysis is pursued for two days and a sample is taken for EM analysis after completion of this dialysis step. The dialyzed reassembly solution is subsequently dialyzed against 50% v/v Glycerol in NET buffer, to achieve concentration. One change of buffer is effected after one day of dialysis. The dialysis is pursued over a total of three days.

The dialyzed and concentrated reassembly solution is purified by gel filtration over a Sepharose 4-B column (1×60 cm) at a flow rate of 1 ml/hour, in NET buffer. Fractions are tested in an Ouchterlony assay, and fractions containing capsids are dried, resuspended in water, and rechromatographed on the 4-B column equilibrated in 20 mM Hepes pH 7.6. Using each of the following three formula:

1. (183*OD230 nm−75.8*OD260 nm)*volume (ml) 2. ((OD235 nm−OD280 nm)/2.51)×volume−3. ((OD228.5 nm−OD234.5 nm)*0.37)×volume protein amounts of 6-26 mg of reassembled VLP were determined.

The reassembled AP205 VLPs are analyzed by EM as described above, agarose gel electrophoresis and SDS-PAGE under non-reducing conditions.

C. Coupling of p33 Epitope (Sequence: H2N-KAVYN-FATMGGC-COOH, with Free N— and C— Termini (SEQ ID NO: 54)) to AP205 VLPs Reassembled with G8-8

Reassembled AP205 VLP obtained as described in part B, and in 20 mM Hepes, 150 mM NaCl, pH 7.4 is reacted at a concentration of 1.4 mg/ml with a 5-fold excess of the crosslinker SMPH diluted from a 50 mM stock in DMSO for 30 minutes at 15° C. The obtained so-called derivatized AP205 VLP is dialyzed 2×2 hours against at least a 1000-fold volume of 20 mM Hepes, 150 mM NaCl, pH 7.4 buffer. The derivatized AP205 is reacted at a concentration of 1 mg/ml with either a 2.5-fold, or with a 5-fold excess of peptide, diluted from a 20 mM stock in DMSO, for 2 hours at 15° C. The sample is subsequently flash frozen in liquid nitrogen for storage.

The coupling reaction is analyzed on an SDS-PAGE.

EXAMPLE 9

Non-Enzymatic Hydrolysis of the RNA Content of VLPs and Packaging of Immunostimulatory Nucleic Acids.

ZnSO4 Dependent Degradation of the Nucleic Acid Content of a VLP:

5 mg Qβ VLP (as determined by Bradford analysis) in 20 mM HEPES, pH 7.4, 150 mM NaCl was dialysed either against 2000 ml of 50 mM Tris HCl pH 8.0, 50 mM NaCl, 5% glycerol, 10 mM MgCl2 or 2000 ml of 4 mM HEPES, pH 7.4, 30 mM NaCl for 2 h at 4° C. in SnakeSkin™ pleated dialysis tubing (Pierce, Cat. No. 68035). Each of the dialysis buffers was exchanged once and dialysis was allowed to continue for another 16 h at 4° C. The dialysed solution was clarified for 10 minutes at 14 000 rpm (Eppendorf 5417 R, in fixed angle rotor F45-30-11, used in all the following steps) and proteinconcentration was again determined by Bradford analysis. Qβ VLPs in 50 mM Tris HCl pH 8.0, 50 mM NaCl, 5% glycerol, 10 mM MgCl2 were diluted with the corresponding buffer to a final protein concentration of 1 mg/ml whereas Qβ VLPs in 4 mM HEPES pH 7.4, 30 mM NaCl were diluted with the corresponding buffer to a final protein concentration of 0.5 mg/ml. This capsid-containing solutions were centrifuged again for 10 minutes at 14 000 rpm at 4° C. The supernatants were than incubated with ZnSO4 which was added to a final concentration of 2.5 mM for 24 h at 60° C. in an Eppendorf Thermomixer comfort at 550 rpm. After 24 h the solutions were clarified for 10 minutes at 14000 rpm and the sediment was discarded. The efficiency of the ZnSO4-dependent degradation of nucleic acids was confirmed by agarose gelelectrophoresis. The supernatants were dialysed against 5000 ml of 4 mM HEPES pH 7.4, 30 mM NaCl for 2 h at 4° C. 5000 ml buffer was exchanged once and dialysis continued over night at 4° C. The dialysed solution was clarified for 10 minutes at 14 000 rpm and 4° C., a negligible sediment was discarded and the protein concentration of the supernatants were determined by Bradford analysis. Similar results were obtained with copper chloride/phenanthroline/hydrogen peroxide treatment of capsids. Those skilled in the art know alternative non-enzymatic procedures for hydrolysis or RNA.

ZnSO4-treated Qβ VLPs was analyzed by agarose gelelectrophoresis: Qβ VLPs which had been purified from *E. coli* and dialysed either against buffer 1 (50 mM Tris HCl pH 8.0, 50 mM NaCl, 5% glycerol, 10 mM MgCl2) or buffer 2 (4 mM HEPES, pH 7.4, 30 mM NaCl) were incubated either without or in the presence of 2.5 mM zinc sulfate (ZnSO4) for 24 hrs at 60° C. After this treatment equal amounts of the indicated samples (5 μg protein) were mixed with loading dye and loaded onto a 0.8% agarose gel. After the run the gel was stained with ethidium bromide. Treatment of VLPs with ZnSO4 caused degradation of the nucleic acid content, while the mock-treated controls were unaffected.

Packaging of Oligodeoxynucleotides into ZnSO4-Treated VLPs:

ZnSO4-treated and dialysed Qβ capsids with a protein concentration (as determined by Bradford analysis) beween 0.4 mg/ml and 0.9 mg/ml (which corresponds to a concentration of capsids of 159 nM and 357.5 nM, respectively) were used for the packaging of the oligodeoxynucleotides. The oligodeoxynucleotides were added at a 300-fold molar excess to the of Qβ-VLP capsids and incubated for 3 h at 37° C. in an Eppendorf Thermomixer comfort at 550 rpm. After 3 h the reactions were centrifuged for 10 minutes at 14 000 rpm and 4° C. The supernatants were dialysed in Spectra/Por®CE DispoDialyzer with a MWCO 300'000 (Spectrum, Cat. No. 135 526) against 5000 ml of 20 mM HEPES pH 7.4, 150 mM NaCl for 8 h at 4° C. 5000 ml buffer was exchanged once and dialysis continued over night at 4° C. The protein concentration of the dialysed samples were determined by Bradford analysis. Qβ capsids and their nucleic acid contents were analyzed as described in Examples 5 and 7.

Packaging of oligodeoxynucleotides into ZnSO4-treated VLPs was analyzed by agarose gelelectrophoresis. Qβ VLPs which had been treated with 2.5 mM zinc sulfate (+ZnSO4) were dialysed against 4 mM HEPES, pH 7.4, 30 mM NaCl and incubated for 3 hrs at 37° C. with an excess of oligodeoxynucleotides (due to the dialysis the concentration of ZnSO4 was decreased by an order of 106, therefore its indicated only in parenthesis) After this incubation in presence of oligodeoxynucleotides, equal amounts of the indicated samples (5 μg protein) were mixed with loading dye and loaded onto a 0.8% agarose gel. After the run the gel was stained with ethidium bromide. Adding of oligodeoxynucleotides to ZnSO4-treated Qβ VLPs could restore the electrophoretical behaviour of the so treated capsids when compared to untreated Qβ capsids which had been purified from *E. coli*.

The nucleic acid content of ZnSO4- and oligodeoxynucleotide treated Qβ VLPs was analyzed by Benzonase and proteinase K digestion and polyacrylamide TBE/Urea gelelectrophoresis: Oligodeoxynucleotides were packaged into ZnSO4-treated Qβ VLPs as described above. 25 μg of these VLPs were digested with 25 μl Benzonase (Merck, Cat. No. 1.01694.0001) according to the manufactures instructions. After heat-inactivation of the nuclease (30 minutes at 80° C.) the VLPs were treated with Proteinase K (final enzyme concentration was 0.5 mg/ml) according to the manufactures instructions. After 3 hrs the equivalent of 2 ug Qβ VLPs which had been digested by Benzonase and proteinase K were mixed with TBE-Urea sample buffer and loaded on a 15% polyacrylamide TBE-Urea gel (Novex®, Invitrogen Cat. No. EC6885). The capsids loaded in lane 2 were treated with 2.5 mM ZnSO4 in presence of buffer 1 (see above), while the capsids loaded in lane 3 were treated with 2.5 mM ZnSO4 in presence of buffer 2 (see above). As qualitative as well as quantitative standard, 1 pmol, 5 pmol and 10 pmol of the oligodeoxynucleotide which was used for the reassembly reaction, was loaded onto the same gel (lanes 4-6). As control, Qβ capsids which had been purified from *E. coli* were treated exactly the same and analyzed on the same polyacrylamide TBE-Urea gel (lane 1). After the run was completed, the gel was fixed, equilibrated to neutral pH and stained with SYBR-Gold (Molecular Probes Cat. No. S-11494). Intact Qβ VLPs (which had been purified from *E. coli*) did not contain nucleic acids of similar size than those which had been extracted from ZnSO4- and oligodeoxynucleotide treated Qβ capsids. In addition, nucleic acids isolated from the latter VLPs were comigrating with the oligodeoxynucleotides which had been used in the reassembly reaction. These results confirmed that the used oligodeoxynucleotides were packaged into ZnSO4-treated Qβ capsids.

EXAMPLE 10

VLPs Containing Containing Immunostimulatory Nucleic Acids Induce T Cell Responses that can be Boosted by Viral Vectors: LCMV.

Mice were subcutaneously primed with 20 μg p33-VLPs (see EXAMPLE 1) containing immunostimulatory nucleic acids. Before immunization, p33-VLP preparations were extensively purified from unbound CpG-oligonucleotides via dialysis. 12 days later, blood was taken and frequencies of p33-specific T cells were determined by tetramer staining. The mice were boosted with 200 pfu of live LCMV strain WE and frequencies of specific T cells were determined 5 days later. Frequencies before boost were 3.5%+/−1.8% and after boost 15.5%+/−1.9%.

EXAMPLE 11

VLPs Containing Immunostimulatory Nucleic Acids Induce T Cell Responses that can be Boosted by Viral Vectors: Recombinant Vaccinia Virus.

Mice are subcutaneously primed with 20 μg p33-VLPs (see EXAMPLE 1) containing immunostimulatory nucleic acids. Before immunization, p33-VLP preparations are extensively purified from unbound CpG-oligonucleotides via dialysis. 12 days later, blood is taken and frequencies of p33-specific T cells are determined by tetramer staining. The mice are boosted with 106 pfu of recombinant vaccina virus expressing LCMV-GP and frequencies of specific T cells are determined 5 days later.

EXAMPLE 12

VLPs Containing Immunostimulatory Nucleic Acids Induce T Cell Responses that can be Boosted by Viral Vectors: Recombinant Canary Pox Virus.

Mice are subcutaneously primed with 20 μg p33-VLPs containing immunostimulatory nucleic acids. Before immunization, p33-VLP preparations are extensively purified from unbound CpG-oligonucleotides via dialysis. 12 days later, blood is taken and frequencies of p33-specific T cells are determined by tetramer staining. The mice are boosted with 107 pfu of recombinant canary pox virus expressing LCMV-GP and frequencies of specific T cells are determined 5 days later.

EXAMPLE 13

VLPs Containing Containing Immunostimulatory Nucleic Acids can Boost T Cell Responses.

Mice are infected intravenously with recombinant vaccina virus expressing LCMV-GP. 20 days later, blood is taken and frequencies of p33-specific T cells are determined by tetramer staining. The mice are boosted the same day with p33-VLP preparations containing immunostimulatory nucleic acids and frequencies of specific T cells are determined 5 days later.

EXAMPLE 14

Coupling of Antigenic Peptides After Packaging of Immunostimulatory Nucleic Acids into VLPs.

RNaseA and ZnSO4 Mediated Degradation of the Nucleic Acid Content of a VLP.

Qβ VLPs were treated with RNaseA as described in Example 7 under low ionic strength conditions (20 mM Hepes pH 7.4 or 4 mM Hepes, 30 mM NaCl, pH 7.4). Similarly, other VLPs such as described in Examples 2, 3, 5, and 8, i.e. GA, BKV, HBcAg, and AP205 are treated. Alternatively, Qβ VLPs and AP205 VLPs were treated with ZnSO4 under low ionic strength conditions (20 mM Hepes pH 7.4 or 4 mM Hepes, 30 mM NaCl pH 7.4) as described in Example 9. AP205 VLP (1 mg/ml) in either 20 mM Hepes pH 7.4 or 20 mM Hepes, 1 mM Tris, pH 7.4 was treated for 48 h with 2.5 mM ZnSO4 at 50° C. in an Eppendorf Thermomixer comfort at 550 rpm. Qβ and AP205 VLP samples were clarified as described in Example 9 and supernatants were dialysed in 10.000 MWCO Spectra/Por® dialysis tubing (Spectrum, Cat. nr. 128 118) against first 2 l 20 mM Hepes, pH 7.4 for 2 h at 4° C. and, after buffer exchange, overnight. Samples were clarified after dialysis as described in Example 9 and protein concentration in the supernatants was determined by Bradford analysis.

Packaging of ISS into RnaseA and ZnSO4 Treated VLPs.

After RNA hydrolysis and dialysis, Qβ and AP205 VLPs (1-1.5 mg/ml) were mixed with 130 μl of CpG oligonucleotides (G3-6, G8-8-cf. Table 1; 1 mM oligonucleotide stock in 10 mM Tris pH 8) per ml of VLPs. Samples were incubated for 3 h at 37° C. in a thermoshaker at 650 rpm. Subsequently, samples were treated with 125 U Benzonase/ml VLPs (Merck KGaA, Darmstadt, Germany) in the presence of 2 mM MgCl2 and incubated for 3 h at 37° C. before dialysis. Samples were dialysed in 300.000 MWCO Spectra/Por® dialysis tubing (Spectrum, Cat. nr. 131 447) against 20 mM Hepes, pH 7.4 for 2 h at 4° C., and after buffer exchange overnight against the same buffer. After dialysis samples were clarified as described in Example 9 and protein concentration in the supernatants were determined by Bradford analysis.

Coupling of Immunogenic Peptides to ISS Packaged VLPs.

Qβ VLPs, packaged with ISS were coupled to p33 peptides containing a C-terminal GGC extension KAVYNFATM-GGC) (SEQ ID NO: 84), resulting in Qb VLPs termed Qb-ISS-33 VLPs. Packaged Qβ VLPs in 20 mM Hepes, pH 7.4 were derivatized with a 10-fold molar excess of SMPH (Pierce) for 0.5 h at 25° C., followed by two dialysis steps of 2 hours each against 20 mM HEPES pH 7.4 at 4° C. to remove unreacted SMPH. Peptides were added in a 5-fold molar excess to the dialysed derivatization mixture, and allowed to react for 2 h in a thermomixer at 25° C. Samples were dialysed in 300.000 MWCO Spectra/Por® dialysis tubing against 20 mM Hepes pH 7.4 for 2 h at 4° C., and after buffer exchange overnight against the same buffer. After dialysis samples were clarified as described in Example 9 and protein concentration in the supernatants were determined by Bradford analysis. Coupling of peptide p33 to Qβ was analysed by SDS-PAGE on 16% PAGE Tris-Glycine gels (Novex® by Invitrogen, Cat.

No. EC64952), using a sample buffer containing 2% SDS and β-mercapto ethanol or DTT. Packaging was analysed on 1% agarose gels and, after proteinase K digestion, on TBE/urea gels as described in Example 5.

AP205 VLPs (1.24 mg/ml) packaged with G8-8 oligonucleotide as described above were derivatized and coupled to HIVp17 (71-85) containing a N-terminal GGC extension (CGG-GSEEIRSLYNTVATL) (SEQ ID NO: 85), resulting in AP205-G8-8-HIVp17 VLPs. AP205 VLPs (packaged with G8-8), in 20 mM Hepes pH 7.4, were derivatized with a 20-fold molar excess of SMPH for 0.5 h at 25° C., and subsequently dialysed two times against 20 mM HEPES, pH 7.4 at 4° C. to remove unreacted SMPH. Peptide was added to the dialyzed derivatization mixture in a 10-fold molar excess and allowed to react for 2 h in a thermomixer at 25° C. Samples were dialysed in 10.000 MWCO dialysis tubing against 20 mM Hepes pH 7.4 for 2 h at 4° C., and after buffer exchange, overnight against the same buffer. After dialysis, samples were clarified as described in Example 9 and protein concentration in the supernatants were determined by Bradford analysis. Coupling efficiency of peptide HIVp17 to AP205 was analysed by SDS-PAGE on 16% PAGE Tris-Glycine gels. G8-8 oligonucleotide packaging in AP205 was analysed on 1% agarose gels and, after proteinase K digestion, G8-8 oligonucleotide amount in AP205-G8-8-HIVp17 was analysed on TBE/urea gels as described in Example 5.

Packaging of G8-8 oligonucleotides into Qβ VLPs and subsequent coupling to p33 peptide was analyzed by agarose gelelectrophoresis. Qβ VLPs containing G8-8 oligonucleotides and subsequently coupled to p33 peptide were termed Qb-G8-8-33 VLPs. Ethidium bromide staining of G8-8 packaged Qβ VLPs can be seen on a 1% agarose gel stained with ethidium bromide. Comigration of the ethidium bromide fluorescent band with the Qβ VLP protein band visible on the same gel subsequently stained with Coomassie Blue demonstrates packaging. Coupling efficiency can be estimated to be 30% by SDS-PAGE analysis on a 16% PAGE Tris-Glycine gel. Analysis of the G8-8 content of Qb-G8-8-33 VLPs after coupling was done on a 1% agarose gel, where the amount of oligonucleotide packaged was of approximately 1 nmol/100 μg Qb-G8-8-33 VLPs.

Packaging of G8-8 oligonucleotides into AP205 VLPs was analyzed by gelelectrophoresis. Staining of G8-8 packaged AP205 VLPs can be seen on a 1% agarose gel stained with ethidium bromide. Comigration of the AP205 VLPs protein band detected on the same gel subsequently stained with Coomassie Blue demonstrated packaging. Coupling efficiency with the HIVp17 peptide could be estimated from the SDS-PAGE analysis on a 16% PAGE Tris-Glycine gel where multiple coupling bands migrating slower than the residual AP205 VLP monomer subunits, which did not react with peptide, are visible. Coupling efficiency was comparable to the coupling efficiency obtained for the Qb-G8-8-33 VLPs. Analysis of the 08-8 oligonucleotide content of AP205 VLPs after coupling to HIVp17 can be seen on TBE/urea gel electrophoresis indicating a packaged amount of 0.5-1 nmol/100 μg AP205-G8-8-HIVp17 VLPs.

EXAMPLE 15

Packaging of Immunostimulatory Guanosine Flanked Oligonucleotides into VLPs.

Qbx33 VLPs (Qβ VLPs coupled to peptide p33, see Example 7) were treated with RNaseA under low ionic conditions (20 mM Hepes pH 7.4) as described in Example 7 to hydrolyse RNA content of the Qbx33 VLP. After dialysis against 20 mM Hepes pH 7.4, Qbx33 VLPs were mixed with guanosine flanked oligonucleotides (Table 1: G3-6, G7-7, G8-8, G9-9 or G6, from a 1 mM oligonucleotide stock in 10 mM Tris pH 8) and incubated as described in Example 14. Subsequently, Qbx33 VLPs were treated with Benzonase and dialysed in 300.000 MWCO tubing. Samples with oligos G7-7, G8-8 and G9-9 were extensively dialysed over 3 days with 4 buffer exchanges to remove free oligo. Packaging was analysed on 1% agarose gels and, after proteinase K digestion, on TBE/urea gels as described in Example 5.

TABLE 1

Sequences of immunostimulatory nucleic acids used in the Examples.

| ISS name | 5'-3' sequence | SEQ ID NO |
|---|---|---|
|  | GACGATCGTC | 1 |
| G3-6 | GGGGACGATCGTCGGGGGG | 2 |
| G4-6 | GGGGGACGATCGTCGGGGGG | 3 |
| G5-6 | GGGGGGACGATCGTCGGGGGG | 4 |
| G6-6 | GGGGGGGACGATCGTCGGGGGG | 5 |
| G7-7 | GGGGGGGGACGATCGTCGGGGGGG | 6 |
| G8-8 | GGGGGGGGGACGATCGTCGGGGGGGG | 7 |
| G9-9 | GGGGGGGGGGACGATCGTCGGGGGGGGG | 8 |
| G6 | GGGGGGCGACGACGATCGTCGTCGGGGGGG | 9 |

Small letters indicate deoxynucleotides connected via phosphorothioate bonds while larger letters indicate deoxynucleotides connected via phosphodiester bonds Packaging of G3-6, G6 and G8-8 oligonucleotides in RNaseA treated Qbx33 VLPs was analyzed by agarose gelelectrophoresis. Upon oligonucleotide packaging, a fluorescent band migrating slightly slower than reference untreated Qβ VLP becomes visible on the 1% agarose gel stained with ethidium bromide indicating the presence of oligonucleotides. The signal is maintained after treatment with Benzonase, indicating packaging of the oligonucleotides within the Qbx33 VLPs. The packaging efficiency can be estimated from the TBE/urea gel electrophoresis. The amount of the G3-6 oligonucleotide (approximately 4 nmol/100 μg Qbx33 VLPs) packaged is much higher than the amount of packaged G8-8 oligonucleotide (approximately 1 nmol/100 μg Qbx33 VLPs). This indicates a dependence of packaging ability on the length of the guanosine nucleotides tail flanking the CpG motif.

EXAMPLE 16

Packaging Ribonucleic Acid into VLPs.
ZnSO4 Dependent Degradation of the Nucleic Acid Content of a VLP.

Qβ VLPs were treated with ZnSO4 under low ionic strength conditions (20 mM Hepes pH 7.4 or 4 mM Hepes, 30 mM NaCl, pH 7.4) as described in Example 9. AP205 VLPs (1 mg/ml) in either 20 mM Hepes pH 7.4 or 20 mM Hepes, 1 mM Tris, pH 7.4 were treated for 48 h with 2.5 mM ZnSO4 at 50° C. in an Eppendorf Thermomixer comfort at 550 rpm. Qβ and AP205 VLP samples were clarified as in Example 9 and dialysed against 20 mM Hepes, pH 7.4 as in Example 14.

Packaging of Poly (I:C) into ZnSO4-Treated VLPs:
The immunostimulatory ribonucleic acid poly (I:C), (Cat. nr. 27-4732-01, poly(I)•poly(C), Pharmacia Biotech) was dissolved in PBS (Invitrogen cat. nr. 14040) or water to a concentration of 4 mg/ml (9 μM). Poly (I:C) was incubated for 10 minutes at 60° C. and then cooled to 37° C. Incubated poly (I:C) was added in a 10-fold molar excess to either ZnSO4-treated Qβ or AP205 VLPs (1-1.5 mg/ml) and the mixtures were incubated for 3 h at 37° C. in a thermomixer at 650 rpm. Subsequently, excess of free poly (I:C) was enzymatically hydrolysed by incubation with 125 U Benzonase per ml VLP mixture in the presence of 2 mM MgCl2 for 3 h at 37° C. in a thermomixer at 300 rpm. Upon Benzonase hydrolysis samples were clarified as described in Example 9 and supernatants were dialysed in 300.000 MWCO Spectra/Por® dialysis tubing (Spectrum, Cat. nr. 131 447) against 2 l 20 mM Hepes, pH 7.4 for 2 h at 4° C., and after buffer exchange overnight against the same buffer. After dialysis, samples were clarified as described in Example 9 and protein concentration in the supernatants were determined by Bradford analysis.

Coupling of Immunogenic Peptides to Poly (I:C) Packaged VLPs.

Qβ VLPs (1 mg/ml) packaged with poly (I:C) were derivatized and coupled either to p33 peptide (KAVYNFATM-GGC) (SEQ ID NO: 84) as described in Example 14, or to MelanA peptide (MelanA 16-35A/L CGHGHSYTTAEELA-GIGILTV) (SEQ ID NO: 40), resulting in Qb-pIC-33 and Qb-pIC-MelanA VLPs, respectively. For coupling to MelanA peptide, the packaged Qβ VLP was derivatized with a 2.1-fold molar excess of SMPH (Pierce) for 0.5 h at 25° C., followed by two dialysis steps against 20 mM HEPES, pH 7.4 at 4° C. to remove unreacted SMPH. Peptides were added in a 2.1-fold molar excess and allowed to react for 1.5 h in a thermomixer at 25° C. Samples were dialysed in 300.000 MWCO Spectra/Por® CE Dispo Dialyzer against 20 mM Hepes, pH 7.2 for 3 h at 4° C., and after buffer exchange, overnight against the same buffer. After dialysis samples were clarified as described in Example 9 and protein concentration in the supernatants were determined by Bradford analysis. Coupling of peptide p33 and peptide MelanA to Qβ was analysed by SDS-PAGE on 16% PAGE Tris-Glycine gels. Packaging was analysed on 1% agarose gels and, after proteinase K digestion, on TBE/urea gels as described in Example 5.

AP205 VLPs (1 mg/ml) packaged with poly (I:C) were derivatized and coupled to HIVp17 (71-85) containing a N-terminal GGC extension (CGG-GSEEIRSLYNTVATL) (SEQ ID NO: 85), resulting in AP205-pIC-HIVp17 VLPs. AP205 VLPs, in 20 mM Hepes, pH 7.4 were derivatized with a 20-fold molar excess of SMPH for 0.5 h at 25° C., and subsequently dialysed two times against 20 mM HEPES, pH 7.4 at 4° C. to remove unreacted SMPH. Peptide was added to the dialyzed derivatization mixture in a 10-fold molar excess and allowed to react for 2 h in a thermomixer at 25° C. Samples were dialysed in 10.000 MWCO dialysis tubing against 20 mM Hepes pH 7.4 for 2 h at 4° C., and after buffer exchange, overnight against the same buffer. After dialysis, samples were clarified as described in Example 9 and protein concentration in the supernatants were determined by Bradford analysis. Coupling efficiency of peptide HIVp17 to AP205 was analysed by SDS-PAGE on 16% PAGE Tris-Glycine gels. Poly (I:C) packaging was analysed on 1% agarose gels and, after proteinase K digestion, on TBE gels as described in Example 5.

Packaging of poly (I:C) into ZnSO4 treated Qβ VLPs and coupling with MelanA peptide resulting in Qb-pIC-MelanA VLPs was analyzed by agarose gelelectrophoresis. The fluorescent signal visible on an ethidium bromide stained 1% agarose gel, indicating presence of nucleic acid, co-migrates with the protein band that became visible upon Coomassie Blue staining of the gel, demonstrating packaging. Coupling efficiency of the MelanA peptide was estimated by SDS-PAGE analysis on a 16% PAGE Tris-Glycine gel. Multiple coupling products were visible as bands migrating slower than the Qβ VLP monomer subunits, which had not reacted with peptide. Coupling efficiency of MelanA was overall comparable to the coupling efficiency obtained for the Qb-G8-8-33 VLPs and the AP205-G8-8-HIVp17 VLPS of Example 14, albeit slightly lower. The packaging efficiency into Qb-pIC-MelanA could be estimated from the TBE/urea gel; the packaged amount of poly (I:C) in Qβ was approximately 25 pmol and remained the same upon MelanA coupling.

Packaging of poly (I:C) into ZnSO4 treated AP205 VLPs and in the coupling product AP205-pIC-HIVp17 after coupling to HIVp17 was analyzed by agarose gelelectrophoresis. The fluorescent band visible on an ethidium bromide stained 1% agarose gel, indicating presence of nucleic acid, co-migrates with the protein band that became visible upon Coomassie Blue staining of the gel both before and after coupling to HIVp17. Coupling efficiency of the HIVp17 peptide is estimated from the appearance of multiple coupling products visible as bands migrating slower than AP205 VLP subunit monomer, which did not react with peptide, after SDS-PAGE analysis on a 16% PAGE Tris-Glycine gel electrophoresis. Coupling efficiency was overall comparable to the coupling efficiency obtained for the Qb-G8-8-33 VLPs and the AP205-G8-8-HIVp17 VLPs (Example 14). The packaging efficiency could be estimated from the TBE gel, which showed that the packaged amounts of poly (I:C) in the AP205-pIC-HIVp17 VLP is approximately 10 pmol/100 μg VLP.

Packaging of G8-8 into ZnSO4-treated VLPs and coupling of immunogenic peptides to G8-8 packaged VLP can be performed accordingly.

EXAMPLE 17

Packaging of Immunostimulatory Guanosine Flanked Oligonucleotides into HBcAg VLPs.

HBcAg VLPs are treated with RNaseA under low ionic strength conditions (20 mM Hepes pH 7.4) as described in Example 7 to hydrolyse RNA content of the VLP. After dialysis against 20 mM Hepes, pH 7.4, VLPs are mixed with guanosine flanked oligonucleotides (Table 1; G3-6, G7-7, G8-8, G9-9, or G6, 1 mM stock in 10 mM Tris pH 8) and incubated as described in Example 14. Subsequently, VLPs are treated with Benzonase and dialysed in 300.000 MWCO tubing. Packaging is analysed on 1% agarose gels and on TBE/urea gels after proteinase K digestion as described in Example 5.

EXAMPLE 18

Packaging of Immunostimulatory Guanosine Flanked Oligonucleotides into GA VLPs.

GA VLPs are treated with RNaseA under low ionic conditions (20 mM Hepes pH 7.4) as described in Example 7 to hydrolyse RNA content of the VLP. After dialysis against 20 mM Hepes pH 7.4, VLPs are mixed with guanosine flanked oligonucleotides (Table 1; G3-6, G7-7, G8-8, G9-9, or G6, 1 mM stock in 10 mM Tris pH8) and incubated as described in Example 14. Subsequently, VLPs are treated with Benzonase and dialysed in 300.000 MWCO tubing. Packaging is analysed on 1% agarose gels and on TBE/urea gels after proteinase K digestion as described in Example 5.

EXAMPLE 19

Packaging Ribonucleic Acid into HBcAg VLPs.

HBcAg VLPs are treated with ZnSO4 under low ionic strength conditions (20 mM Hepes pH 7.4 or 4 mM Hepes, 30 mM NaCl, pH 7.4) as described in Example 9 and are dialysed against 20 mM Hepes pH 7.4 as in Example 14. G8-8 is added in a 10-fold molar excess to HBcAg VLPs (1-1.5 mg/ml) and incubated for 3 h at 37° C. in a thermomixer at excess to HBcAg VLPs (1-1.5 mg/ml) and incubated for 3 h at 37° C. in a thermomixer at hydrolysed by incubation with 125 U Benzonase per ml VLP mixture in the presence of 2 mM MgCl2 for 3 h at 37° C. in a thermomixer at 300 rpm. Samples are clarified after Benzonase hydrolysis as described in Example 9 and dialysed as in Example 16. After dialysis, samples are clarified as described in Example 9 and protein concentration in the supernatants are determined by Bradford analysis. HBcAg VLPs (1 mg/ml) packaged with G8-8 are derivatized and coupled either to MelanA or to HIVp17 peptide, and dialysed as in Example 16.

EXAMPLE 20

Packaging Ribonucleic Acid into GA VLPs.

GA VLPs are treated with ZnSO4 under low ionic strength conditions (20 mM Hepes pH 7.4 or 4 mM Hepes, 30 mM NaCl, pH 7.4) as described in Example 9 and are dialysed against 20 mM Hepes, pH 7.4 as in Example 14. G8-8 is added in a 10-fold molecular excess to GA VLPs (1-1.5 mg/ml) and incubated for 3 h at 37° C. in a thermomixer at 650 rpm as described in Example 16. Subsequently, excess of free G8-8 is enzymatically hydrolysed by incubation with 125 U Benzonase per ml VLP mixture in the presence of 2 mM MgCl2 for 3 h at 37° C. in a thermomixer at 300 rpm. Samples are clarified after Benzonase hydrolysis as described in Example 9 and dialysed as in Example 16. After dialysis, samples are clarified as described in Example 9 and protein concentration in the supernatants are determined by Bradford analysis. GA VLPs (1 mg/ml) packaged with G8-8 are derivatized and coupled either to MelanA or to HIVp17 peptide, and dialysed as in Example 16.

EXAMPLE 21

Qβ Disassembly, Reassembly and Packaging of Oligodeoxynucleotides.

Disassembly and Reassembly of Qβ VLP

Disassembly: 45 mg Qβ VLP (2.5 mg/ml, as determined by Bradford analysis) in PBS (20 mM Phosphate, 150 mM NaCl, pH 7.5), was reduced with 10 mM DTT for 15 min at RT under stirring conditions. A second incubation of 15 min at RT under stirring conditions followed after addition of magnesium chloride to a final concentration of 700 mM, leading to precipitation of the encapsulated host cell RNA and concomitant disintegration of the VLPs. The solution was centrifuged 10 min at 4000 rpm at 4° C. (Eppendorf 5810 R, in fixed angle rotor A-4-62 used in all following steps) in order to remove the precipitated RNA from the solution. The supernatant, containing the released, dimeric Qβ coat protein, was used for the chromatography purification steps.

Two-step purification method for Qβ coat protein by cation exchange chromatography and size exclusion chromatography: The supernatant of the disassembly reaction, containing dimeric coat protein, host cell proteins and residual host cell RNA, was applied onto a SP-Sepharose FF column (xk16/20, 6 ml, Amersham Bioscience). During the run, which was carried out at RT with a flow rate of 5 ml/min, the absorbance at 260 nm and 280 nm was monitored. The column was equilibrated with 20 mM sodium phosphate buffer pH 7 and the sample was diluted 1:15 in water to adjust a conductivity below 10 mS/cm in order to achieve proper binding of the coat protein to the column. The elution of the bound coat protein was accomplished by a step gradient to 20 mM sodium phosphate/500 mM sodium chloride and the protein was collected in a fraction volume of approx. 25 ml. The column was regenerated with 0.5 M NaOH.

In the second step, the isolated Qβ coat protein dimer (the eluted fraction from the cation exchange column) was applied (in two runs) onto a Sephacryl S-100 HR column (xk26/60, 320 ml, Amersham Bioscience) equilibrated with 20 mM sodium phosphate/250 mM sodium chloride; pH 6.5. Chromatography was performed at RT with a flow rate of 2.5 ml/min. Absorbance was monitored at 260 nm and 280 nm. Fractions of 5 ml were collected. The column was regenerated with 0.5 M NaOH.

Reassembly by dialysis: A stock solution of purified Qβ coat protein dimer at a concentration of 2 mg/ml was used for the reassembly of Qβ VLP in the presence of the oligodeoxynucleotide G8-8. The concentration of oligodeoxynucleotide in the reassembly mixture was 10 μM. The concentration of coat protein dimer in the reassembly mixture was 40 μM (approx. 1.13 mg/ml). Stock solutions of urea and DTT were added to the solution to give final concentrations of 1 M urea and 5 mM DTT respectively. The oligodeoxynucleotide was added as last component, together with $H_2O$, giving a final volume of the reassembly reaction of 3 ml. This solution was dialysed at 4° C. for 72 h against 1500 ml buffer containing 20 mM Tris HCl, 150 mM NaCl, pH 8.0. The dialysed reassembly mixture was centrifuged at 14 000 rpm for 10 minutes at 4° C. A negligible sediment was discarded while the supernatant contained the reassembled and packaged VLPs. Reassembled and packaged VLPs were concentrated with centrifugal filter devices (Millipore, UFV4BCC25, 5K NMWL) to a final protein concentration of 3 mg/ml. Protein concentration was determined by Bradford analysis.

Purification of reassembled and packaged VLPs by size exclusion chromatography: Up to 10 mg total protein was loaded onto a Sepharose™ CL-4B column (xk16/70, Amersham Biosciences) equilibrated with 20 mM HEPES, 150 mM NaCl, pH 7.4. The chromatography was performed at room temperature at a flow-rate of 0.4 ml/min. Absorbance was monitored at 260 nm and 280 nm. Two peaks were observed, collected in fractions of 0.5 ml size and analysed by SDS-PAGE. The disulfide-bond pattern in reassembled and purified Qβ capsids was analyzed by non-reducing SDS-PAGE. 5 μg of the indicated capsids were mixed with sample buffer (containing SDS) that contained no reducing agent and loaded onto a 16% Tris-Glycine gel. After the run was completed the gel was stained with Coomassie blue. When compared to "intact" capsids purified from *E. coli*, the reassembled Qβ VLP displayed the same disulfide bond pattern with the bands corresponding to dimer, trimer, tetramer, pentamer and hexamers of the Qb coat protein. Calibration of the column with intact and highly purified Qβ capsids from *E. coli*, revealed that the apparent molecular weight of the major first peak was consistent with Qβ capsids.

Reassembly by diafiltration (optimized method): 20 ml of a stock solution of purified coat protein (1.5 mg/ml) is mixed with stock solutions of urea, DTT, oligodeoxynucleotide G8-8 and water. The oligodeoxynucleotide is added as last component. The volume of the mixture is 30 ml and the final concentrations of the components are 35 μM dimeric coat protein (reflecting 1 mg/ml), 35 μM oligodeoxynucleotide, 1 M urea and 2.5 mM DTT. The mixture is then diafiltrated against 300 ml of 20 mM sodium phosphate/250 mM sodium chloride, pH 7.2, in a tangential flow filtration apparatus at RT, using a Pellicon XL membrane cartridge (Biomax 5K, Millipore). The total flow rate is set to 10 ml/min and the permeate flow rate set to 2.5 ml/min. After completion of the diafiltration step, $H_2O_2$ is added to the solution to a final concentration of 7 mM and the solution is further incubated at RT for 60 min, to accelerate the formation of the structural disulfide bonds in the formed VLPs. The removal of non-incorporated oligodeoxynucleotide and coat protein is achieved by a $2^{nd}$ diafiltration against 600 ml of 20 mM sodium phosphate/250 mM sodium chloride, pH 7.2, using a Pellicon XL membrane cartridge (PLCMK 300K, Millipore).

Analysis of Qβ VLPs which had been reassembled in the presence of oligodeoxynucleotides:

A) Hydrodynamic size of reassembled capsids: Qβ capsids, which had been reassembled in the presence of oligodeoxynucleotide G8-8, were analyzed by dynamic light scattering (DLS) and compared to intact Qβ VLPs, which had been purified from *E. coli*. Reassembled capsids showed the same hydrodynamic size (which depends both on mass and conformation) as the intact Qβ VLPs.

B) Disulfide-bond formation in reassembled capsids: Reassembled Qβ VLPs were analyzed by non-reducing SDS-PAGE and compared to intact Qβ VLPs, which had been purified from *E. coli*. Reassembled capsids displayed a band pattern, with the presence of disulfide-linked pentameric and hexameric forms of the coat protein, similar to the intact Qβ VLPs (as described above).

C) Analysis of nucleic acid content of the Qβ VLPs which had been reassembled in the presence of oligodeoxynucleotides by denaturing polyacrylamide TBE-Urea gelelectrophoresis: Reassembled Qβ VLPs (0.4 mg/ml) containing G8-8 oligodeoxynucleotides were incubated for 2 h at 37° C. with 125 U benzonase per ml Qβ VLPs in the presence of 2 mM $MgCl_2$. Subsequently the benzonase treated Qβ VLPs were treated with proteinase K (PCR-grade, Roche Molecular Biochemicals, Cat. No. 1964364) as described in Example 7. The reactions were then mixed with a TBE-Urea sample buffer and loaded on a 15% polyacrylamide TBE-Urea gel (Novex®, Invitrogen Cat. No. EC6885). As a qualitative as well as quantitative standard, 1 pmol, 5 pmol and 10 pmol of the oligodeoxynucleotide which was used for the reassembling reaction, was loaded on the same gel. This gel was stained with SYBR®-Gold (Molecular Probes Cat. No. S-11494). The SYBR®-Gold stain showed that the reassembled Qβ capsids contained nucleic acid co-migrating with the oligodeoxynucleotides which were used in the reassembly reaction. Taken together, resistance to benzonase digestion of the nucleic acid content of the Qβ VLPs which had been reassembled in the presence of oligodeoxynucleotides and isolation of the oligodeoxynucleotide from purified particles by proteinase K digestion, demonstrate packaging of the oligodeoxynucleotide.

EXAMPLE 22

Coupling of Peptides Derived from MelanA Melanoma Antigen to Qb

TABLE 2

The following MelanA peptide moieties were chemically synthesized:

| Abbreviation* | Sequence** | SEQ ID NO: |
|---|---|---|
|  | ELAGIGILTV | 35 |
|  | GHGHSYTTAE ELAGIGILTV | 36 |
|  | SYTTAEELAGIGILTV ILGVL | 37 |
|  | ELAGIGILTVILGVL | 38 |
| MelanA 16-35 | c GHGHSYTTAE EAAGIGILTV | 39 |
| MelanA 16-35 A/L | c GHGHSYTTAE ELAGIGILTV | 40 |
| MelanA 26-35 | cgg EAAGIGILTV | 41 |
| MelanA 26-35 A/L | cgg ELAGIGILTV | 42 |
| MelanA 20-40 A/L | c SYTTAEELAGIGILTV ILGVL | 43 |
| MelanA 26-40 A/L | cgg ELAGIGILTVILGVL | 44 |
| MelanA 26-35-C A/L | ELAGIGILTV ggc | 45 |
| A 26-35 A/L | L CSPKSL-MelanA | CSPKSLE-110 LAGIG-ILTV |
| MelanA 26-40-C A/L | ELAGIGILTVILGVLGGC | 111 |

*A/L indicates alanin to lysine exchange compared to the original wildtype MelanA peptide
**amino acids from the linker sequence are indicated in small letters The following procedures were used for chemical coupling of the MelanA peptide moieties to Qb VLPs:

For peptide MelanA 16-35, MelanA 16-35 A/L and MelanA 26-35-C A/L: A solution of 2 ml of 3.06 mg/ml Qb VLPs in 20 mM Hepes, pH 7.2 was reacted for 30 minutes with 18.4 μl of a solution of 50 mM SMPH (succinimidyl-6-(β-maleimidopropionoamido hexanoate, Pierce) in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 18.4 μl of 50 mM peptide stock solution (in DMSO) for two hours at 25° C. on a rocking shaker. The reaction mixture was subsequently dialyzed 2×2 hours against 2 liters of 20 mM Hepes, pH 7.2 at 4° C. The coupled products were named Qb-MelanA 16-35 (SEQ ID NO: 39), Qb-MelanA 16-35 A/L (SEQ ID NO: 40) and Qb-MelanA 26-35-C A/L (SEQ ID NO: 55). For MelanA 26-35: A solution of 2 ml of 3.06 mg/ml Qb capsid protein in 20 mM Hepes, pH 7.2 was reacted for 30 minutes with 75.3 μl of a solution of 50 mM SMPH in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 37.7 μl of 50 mM peptide stock solution (in DMSO) for 4 hours at 25° C. on a rocking shaker. The reaction mixture was subsequently dialyzed 2×2 hours against 2 liters of 20 mM Hepes, pH 7.2 at 4° C. The coupled product was named Qb-MelanA 26-35.

For MelanA 26-35 A/L (SEQ ID NO: 42): A solution of 2 ml of 3.06 mg/ml Qb VLPs in 20 mM Hepes, pH 7.2 was reacted for 30 minutes with 37.7 μl of a solution of 50 mM SMPH in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 18.4 μl of 50 mM peptide stock solution (in DMSO) for 4 hours at 25° C. on a rocking shaker. The reaction mixture was subsequently dialyzed 2×2 hours against 2 liters of 20 mM Hepes, pH 7.2 at 4° C. The coupled product was named Qb-MelanA 26-35 A/L.

For MelanA 20-40 A/L (SEQ ID NO: 43): A solution of 2 ml of 3.06 mg/ml Qb VLPs in 20 mM Hepes, pH 7.2 was reacted for 30 minutes with 18.4 µl of a solution of 50 mM SMPH in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 184 µl of 5 mM peptide stock solution (in DMSO) for 4 hours at 25° C. on a rocking shaker. The reaction mixture was subsequently dialyzed 2×2 hours against 2 liters of 20 mM Hepes, pH 7.2 at 4° C. The coupled product was named Qb-MelanA 20-40 A/L.

For MelanA 26-40 A/L (SEQ ID NO: 44): A solution of 2 ml of 3.06 mg/ml Qb VLPs in 20 mM Hepes, pH 7.2 was reacted for 30 minutes with 37.7 µl of a solution of 50 mM SMPH in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 184 µl of 5 mM peptide stock solution (in DMSO) for 4 hours at 25° C. on a rocking shaker. The reaction mixture was subsequently dialyzed 2×2 hours against 2 liters of 20 mM Hepes, pH 7.2 at 4° C. The coupled product was named Qb-MelanA 26-40 A/L.

Coupling efficiency was checked by SDS-PAGE analysis. FIG. 1 shows the SDS-PAGE analysis of Qb-MelanA VLPs. MelanA-peptides were coupled to Qb VLPs. The final products were mixed with sample buffer and separated under reduced conditions on 16% Novex®Tris-Glycine gels for 1.5 hours at 125 V. The separated proteins were stained by soaking the gel in Coomassie blue solution. Background staining was removed by washing the gel in 50% methanol, 8% acetic acid. The Molecular weight marker (P 77085, New England BioLabs, Beverly, USA) was used as reference for Qb-MelanA migration velocity (lane 1). 14 µg of either Qb alone (lane 2) or Qb derivatized with SMPH (lane 3) were loaded for comparison with 8 µg of each final product: Qb-MelanA 16-35 (lane 4), Qb-MelanA 16-35 A/L (lane 5), Qb-MelanA 26-35 (lane 6) and Qb-MelanA 26-35 A/L (lane7).

The MelanA 16-35 A/L peptide contains the cytotoxic T lymphocyte (CTL) epitope MelanA 26-35 and Qb-MelanA 16-35 A/L was further studied for its immunogenicity in vitro and in vivo.

EXAMPLE 23

Capacity of Immunostimulatory Sequences (ISS) to Activate Human Cells in Vitro

In order to select for the optimal ISS to be loaded in Qb-MelanA vaccine, series of CpG with different number of flanking Gs were tested for their ability to upregulate CD69 on human CD8 T cells and to induce secretion of IFN alpha and IL-12 in human PBMC.

Human PBMC were isolated from buffy coats and treated with the indicated ISS in RPMI medium containing 10% FCS for 18 h. IFN alpha in the supernatants was measured by ELISA, using an antibody set provided by PBL Biomedical Laboratories. PBMC were stained with mouse anti-human CD8-FITC, mouse anti-human CD19-PE and anti-human CD69-APC and analyzed by flow cytometry. G9-9 and G8-8 induced high levels of IFN alpha secretion (FIG. 2A). Decreasing the number of flanking Gs in the other oligonucleotides resulted in lower IFN alpha secretion.

Treatment of PBMC with G9-9 and G8-8 upregulated CD69 on the cell membrane of CD8 T cells to a nearly similar extend. Decreasing the number of flanking Gs (below 7) in the other oligonucleotides reduced their activity to induce secretion of IFN alpha (FIG. 2A) and to upregulate CD69 on T cells (FIG. 2B). These data show that G9-9 and G8-8 have comparable high activity on human cells, therefore they can be used as ISS in Qb-MelanA vaccine.

EXAMPLE 24

Qbx33 VLPs Loaded with G3-6, or G6 Induces Protection Against p33-Recombinant Vaccinia Virus Challenge B6 mice were subcutaneously immunized with Qbx33 alone or loaded with G3-6 or G6 (see Examples 14 and 16). Eight days later, mice were challenged with 1.5×106 pfu of recombinant Vaccinia virus, expressing the LCMV-p33 antigen. After 4 days, mice were sacrificed and the viral titers in ovaries were measured as previously described (Bachmann et al, Eur. J. Imunol. 1994, 24:2228). As depicted in FIG. 3, all mice receiving the Qbx33 vaccine loaded with either G3-6 or G6 were protected from viral challenge. In contrast, naïve mice and mice immunized with Qbx33 alone did not eliminate the virus from the ovaries. These data demonstrate that VLP alone is not sufficient to induce protective CTL immune response, whereas VLP loaded with CpG are very efficient in priming naïve CTL.

Similarly, immunization of mice with Qbx33 loaded with G8-8 is priming p33-specific CTL, as well as is inducing protection from recombinant Vaccinia virus challenge.

EXAMPLE 25

Qβ̃ MelanA 16-35 A/L VLPs are processed and presented by the human MHC class I allele HLA-A0201 and induces expansion of functional MelanA-specific CD8+T cells in HLA-A2 transgenic mice HHD mice express a chimeric monochain class I molecule with a human β2-microglobulin covalently linked to the N-terminus of A2 α1 and α2 domains fused with Db α3 domain (Firat, H. et al 1999, Eur. J. Immunol., 29:3112). The HLA-A2 transgene expression in these mice allows investigating the capacity of Qβ̃MelanA 16-35 A/L VLPs to be processed and presented as the CTL epitope MelanA 26-35 and to prime CTL in vivo. Furthermore, the effect of adjuvants, as ISS can be studied in vivo.

HHD mice were either left untreated or immunized by injecting subcutaneously with 100 µg Qb-MelanA 16-35 A/L or with Qb-pIC-MelanA 16-35 A/L. Eight days later spleenocytes were isolated, resuspended in FACS buffer (PBS, 2% FCS, 5M EDTA, pH 8.2) and stained with HLA-A2-MelanA-PE labelled tetramers for 30 min at room temperature. In a second step, rat anti-mouse CD8-APC (BD PharMingen, San Jose, USA) and anti mouse Mel14-FITC (BD PharMingen, San Jose, USA) were added for 30 min at 4° C. After washing, erythrocytes were lysed with BD-Lyzing Solution (BD Biosciences, San Jose, USA) for 10 min at room temperature. Finally, the spleen cells were analysed on a FACS Calibur using CellQuest software. First of all, the cells were acquired in the forward scatter and side scatter and the lymphocytes were gated. From this lymphocyte population, only the CD8 positive T cells were selected for further analyses. The HLA-A2-MelanA-PE and Mel14-FITC labelled cells were measured with the FL2 and FL1 detector, respectively. The amount of MelanA-specific, activated CD8+ T cells was calculated as percent HLA-A2-MelanA positive, Mel14 negative cells on total CD8+ lymphocytes.

Flow cytometry analysis showed that Qb-pIC-MelanA 16-35 A/L induced a surprisingly high expansion of MelanA-specific activated CD8+Mel14-T cells (2.43% and 0.73%), which was higher compared to untreated animals (0.22% and 0.37%). It should be noted that the capacity of the vaccine increased significantly only when Qb-MelanA was loaded with poly (I:C).

The human HLA-A2-MelanA tetramer does not bind very efficiently to mouse MelanA-specific T cells, as the protein is chimeric. Therefore we could assume a much higher degree of antigen specific T cells in these mice.

In a similar experimental setting, immunization of HHD mice with Qb-MelanA 16-35 A/L or Qb-MelanA 26-35 A/L loaded with G8-8 induces expansion of HLA-A2-MelanA-positive and Mel14 negative CD8 T cells.

Taken together these findings demonstrate the ability of ISS loaded Qb-peptide vaccines to very efficiently prime CTL against foreign and self antigens.

EXAMPLE 26

Coupling of gag-G50, nef-N56 and gag-G68n Peptide Antigen to Qβ VLP

The peptide gag-G50 (sequence: CQGQMVHQAISPRTLNAWVKA FSPEVIPMFSALSEGATPQDLNTMLNTVK) (SEQ ID NO: 86) and nef-N56 (sequence: CGVGFPVRPQVPLRPMTYKAAVDLSHFLKEKGGLE GPGIRYPLTFGWCFKLVPVEP) (SEQ ID NO: 87) and gag-G68n (sequence: CGEIYKRWIILGLNKIVRMYQGQM-VHQAISPRTLNAWVK AFSPEVIPMFSALSEGAT-PQDLNTMLNTVK) (SEQ ID NO: 88) were chemically synthesized. The peptides were ordered from the company SynPep, P.O. Box 2999, Dublin, Calif. 94568, USA. Qβ VLP (Seq-ID No. 10) was then reacted at a concentration of 1.2 mg/ml (determined in a Bradford assay), with 0.85 mM SMPH (Pierce) for 30 minutes at room temperature (RT). The reaction mixture was then diafiltrated against 20 mM phosphate buffer pH 7.2 and 50 mM MES pH 6.0 was added for gag-G50 coupling reactions, and 50 mM Tris pH 8.5 for nef-N56 coupling reactions. A 5 mM stock of peptide was dissolved in DMSO and an equimolar amount TCEP was added to the peptide in order to have reducing reaction conditions. Then, the derivatised Qβ particles reacted at a concentration of 1 mg/ml with 0.214 mM gag-G50, 0.214 mM nef-N56 or 0.535 mM gag-G68n. Both peptides, gag-G50 and nef-N56, were also coupled under the same conditions, but for the buffer, which was 50 mM Tris pH 8.5. The coupling reaction was left to proceed for 2 hours at 25° C.; samples were taken for SDS-PAGE analysis, and the reaction mixtures dialyzed 2×2 hours against a 1000-fold volume 20 mM phosphate, 0.05% Tween, pH 7.2. The dialyzed samples were flash frozen in liquid nitrogen in aliquots for storage at −80° C. until further use. An aliquot was thawed, and coupling of the antigen to a Qβ subunit assessed by SDS-PAGE. The results of the coupling reactions analyzed before the dialysis are shown in FIG. 4 and FIG. 5. Analysis of the dialyzed coupling reaction showed a similar picture.

Coupling bands corresponding to one gag-G50 or nef-N56 peptide coupled per Qβ monomer or dimer are clearly visible demonstrating coupling of both peptides to the Qβ VLP.

EXAMPLE 27

Coupling of HIV Peptides to Packaged Qβ VLP

Qβ VLP packaged with G8-8 oligonucleotide made as described in Example 14 is coupled to HIV peptides as described in Example 26. The sequences of the coupled peptides are gag-G50 (sequence: CQGQMVHQAISPRTL-NAWVKAFSPEVIPMFSALSE GATPQDLNTMLNTVK) (SEQ ID NO: 86) and nef-N56 (sequence: CGVGFPVRPQV-PLRPMTYKAAVDLSHFLKEKGGLEGP-GIRYPLTFGWCFKLVPV EP) (SEQ ID NO: 87) and gag-G68n (sequence: CGEIYKRWIILGLNKIVRMYQGQM-VHQAISPRTLNAWVKAFSPEVIPMFSALSEG ATPQDLNTMLNTVK) (SEQ ID NO: 88). The resulting packaged and coupled Qβ VLP are analysed as described in Example 7 and in Example 14.

EXAMPLE 28

Packaging of Qβ VLP Coupled to HIV Peptides

Qβ VLP is coupled to HIV peptides gag-G50, gag-G68n, or nef-N56 as described in Example 26. Qβ VLP coupled either to gag-G50, gag-G68n, or nef-N56 is packaged with G8-8 oligonucleotide and analysed as described in Example 7.

EXAMPLE 29

Qbx33 loaded with CpG can be used in homologous as well in heterologous prime-boost regimen for the induction of a long lasting memory CD8+ T cell response Mice were immunized with 150 ug Qbx33/NKCpG and 8 days later the frequencies of p33-specific T cells increased from 0.4%+/−0.2% in naïve mice to 7.5%+/−2.2% in immunized animals as measured with antigen specific MHC/peptide tetramers. 20 days later the peptide specific CD8+ T population dropped down to 1.6%+/−0.7%. A second-imunisaiton of these mice 30 days after the first immunisation with 150 ug Qbx33/NKPS could boost the memory T cell response to up to 8.4%+/−1.9% specific T cells. This response dropped slowly down but could be boosted again 4 months after the first boost with 150 ug Qbx33/NKPS reaching T cell levels of 23.8%+/−5.2%.

When 3 mice were primed with 50 ug p33 peptide mixed with 20 nmol NKPS and IFA only 0.6%+/−_0.4% specific CD8+ T cells could be induced until day 8 post-immunisation. Nevertheless, this low response could be boosted efficiently 7 weeks later with Qbx33/NKPS to levels of 28.5%+/−9.8%.

Immunisation with 1×10exp6 plaque forming units of recombinant vaccinia virus expressing the p33-peptide could hardly induce any T cell response (1.1%+/−0.5%) but was boosted very efficiently boosted 6 months later with 150 ug Qbx33/NKPS to T cells levels of 28.1+/−_4.2%.

These results show, that Qb loaded with CpG very efficiently boosts any pre-existing T cell reponse in heterologous as well as homologous prime boost regimens. It should be noted, that Qb/NKPS can even boost a very inefficiently primed T cell response with peptides or recombinant virusus. In addition, when a strong T cell response was established with Qbx33/NKPS we were able to boost this reponse using an immunologically effective amount of a heterologous vaccine such as the p33 peptide alone, recombinant virus expressing p33, or p33 fused or coupled to a VLP. In the latter, the used VLP is not a VLP derived from RNA phage Qb but e.g. HBcAg or VLP derived from AP205.

What is claimed is:

1. A composition comprising:
   (a) a virus-like particle; and
   (b) at least one immunostimulatory substance;
   wherein said immunostimulatory substance is packaged into said virus-like particle, and wherein said immunostimulatory substance is an unmethylated CpG-containing oligonucleotide, wherein the CpG motif of said unmethylated CpG-containing oligonucleotide is part of a palindromic sequence, and wherein said palindromic sequence is flanked at its 3'-terminus and at its 5'-terminus by less than 10 guanosine entities.

2. The composition of claim 1 further comprising at least one antigen or antigenic determinant, wherein said antigen or antigenic determinant is bound to said virus-like particle.

3. The composition of claim 2, wherein said antigen or antigenic determinant is bound to said virus-like particle by at least one non-peptide covalent bond.

4. The composition of claim 2, wherein said virus-like particle comprises at least one first attachment site and wherein said antigen or antigenic determinant further comprises at least one second attachment site being selected from the group consisting of:

(a) an attachment site not naturally occurring with said antigen or antigenic determinant; and
(b) an attachment site naturally occurring with said antigen or antigenic determinant;
and wherein said binding of said antigen or antigenic determinant to said virus-like particle is effected through association between said first attachment site and said second attachment site, wherein said association is through at least one non-peptide covalent bond; and wherein said antigen or antigenic determinant and said virus-like particle interact through said association to form an ordered and repetitive antigen array.

5. The composition of claim 4, wherein said first attachment site comprises an amino group.

6. The composition of claim 4, wherein said second attachment site comprises a sulfhydryl group.

7. The composition of claim 4, wherein said first attachment site is an amino group and said second attachment site is a sulfhydryl group.

8. The composition of claim 2, wherein said antigen is derived from the group consisting of:
(a) viruses;
(b) bacteria;
(c) parasites;
(d) prions;
(e) tumors;
(f) self-molecules;
(g) non-peptidic hapten molecules
(h) allergens; and
(i) hormones.

9. The composition of claim 2, wherein said antigen is a tumor antigen, wherein said tumor antigen is selected from the group consisting of:
(a) Her2;
(b) GD2;
(c) EGF-R;
(d) CEA;
(e) CD52;
(f) CD21;
(g) human melanoma protein gp100;
(h) human melanoma protein melan-A/MART-1;
(i) tyrosinase;
(j) NA17-A nt protein;
(k) MAGE-3 protein;
(l) p53 protein;
(m) HPV16 E7 protein;
(n) human melanoma MelanA peptide;
(o) human melanoma MelanA peptide analogue; and
(p) antigenic fragments of any of the tumor antigens from (a) to (o).

10. The composition of claim 2, wherein said antigen is bound to said virus-like particle by way of a linking sequence.

11. The composition of claim 2, wherein said antigen comprises a cytotoxic T cell epitope, a Th cell epitope or a combination of at least two of said epitopes, wherein said at least two epitopes are bound directly or by way of a linking sequence, and wherein said cytotoxic T cell epitope is a viral or a tumor cytotoxic T cell epitope.

12. The composition of claim 1, wherein said unmethylated CpG-containing oligonucleotide comprises 10 to 30 nucleotides.

13. The composition of claim 1, wherein said palindromic sequence is GACGATCGTC (SEQ ID NO:1).

14. The composition of claim 1, wherein said palindromic sequence is flanked at its 5'-terminus by at least 3 and at most 9 guanosine entities and wherein said palindromic sequence is flanked at its 3'-terminus by at least 6 and at most 9 guanosine entities.

15. The composition of claim 13, wherein said unmethylated CpG-containing oligonucleotide has a nucleic acid sequence selected from
(a) GGGGACGATCGTCGGGGGG (SEQ ID NO:2);
(b) GGGGGACGATCGTCGGGGGG (SEQ ID NO:3);
(c) GGGGGGACGATCGTCGGGGGG (SEQ ID NO:4);
(d) GGGGGGGACGATCGTCGGGGGG (SEQ ID NO:5);
(e) GGGGGGGGACGATCGTCGGGGGGG (SEQ ID NO:6);
(f) GGGGGGGGGACGATCGTCGGGGGGGG (SEQ ID NO:7);
(g) GGGGGGGGGGGACGATCGTCGGGGGGGGG (SEQ ID NO:8); and
(h) GGGGGGGCGACGACGATCGTCGTCGGGGGGG (SEQ TD NO:9).

16. The composition of claim 1, wherein said virus-like particle comprises recombinant proteins of an RNA-phage, wherein said RNA-phage is selected from the group consisting of:
(a) bacteriophage Qβ;
(b) bacteriophage R17;
(c) bacteriophage fr;
(d) bacteriophage GA;
(e) bacteriophage SP;
(f) bacteriophage MS2;
(g) bacteriophage M11;
(h) bacteriophage MX1;
(i) bacteriophage NL95;
(j) bacteriophage f2;
(k) bacteriophage PP7; and
(l) bacteriophage AP205.

17. The composition of claim 1, wherein said virus-like particle comprises recombinant proteins of bacteriophage Qβ or bacteriophage AP205.

18. A vaccine comprising an immunologically effective amount of the composition of claim 1 together with a pharmaceutically acceptable diluent, carrier or excipient.

19. The composition of claim 2, wherein said antigen is an HIV polypeptide.

20. The composition of claim 2, wherein said antigen is a recombinant HIV polypeptide.

21. The composition of claim 2, wherein said antigen is HIV antigen gp 160 or an antigenic fragment thereof.

22. The composition of claim 2, wherein said antigen is HIV antigen gp 140 or an antigenic fragment thereof.

23. The composition of claim 2, wherein said antigen is HIV antigen gp 140.

24. The composition of claim 2, wherein said antigen or antigenic determinant is bound to said virus-like particle by at least one peptide bond.

25. The composition of claim 4, wherein said palindromic sequence is flanked at its 5'-terminus by at least 3 and at most 9 guanosine entities and wherein said palindromic sequence is flanked at its 3'-terminus by at least 6 and at most 9 guanosine entities.

26. The composition of claim 2, wherein said antigen is a tumor antigen.

27. The composition of claim 26, wherein said tumor antigen is derived from breast cancer.

28. The composition of claim 26, wherein said tumor antigen is a recombinant polypeptide of breast cancer cells.

29. The composition of claim 2, wherein said antigen is Her2 or an antigenic fragment thereof.

30. The composition of claim 2, wherein said antigen is Her2.

31. The composition of claim 2, wherein said antigen is a human melanoma MelanA/MART-1 peptide analogue.

32. The composition of claim 2, wherein said antigen consists of the sequence ELAGIGILTV (SEQ ID NO:35).

33. The composition of claim 2, wherein said antigen is a viral antigen.

34. The composition of claim 2, wherein said antigen is derived from a Pneumovirus, wherein said Pneumovirus is the respiratory syncytial virus (RSV).

35. The composition of claim 2, wherein said antigen is a recombinant polypeptide of Influenza virus.

36. The composition of claim 2, wherein said antigen is the influenza antigen M2 protein or an antigenic fragment thereof.

37. The composition of claim 36, wherein said antigen is fused to said virus-like particle, and wherein said virus-like particle is a virus-like particle of an RNA-phage AP205.

38. The composition of claim 2, wherein said antigen is the influenza antigen hemagglutinin or an antigenic fragment thereof.

39. The composition of claim 38, wherein said antigen is fused to said virus-like particle, and wherein said virus-like particle is a virus-like particle of an RNA-phage AP205.

40. The composition of claim 2, wherein said antigen is an allergen.

41. The composition of claim 2, wherein said antigen is Bet v I or an antigenic fragment thereof.

42. The composition of claim 2, wherein said antigen is Bet v I.

43. The composition of claim 1, wherein said unmethylated CpG-containing oligonucleotide consists of the nucleic acid sequence GGGGGGGGGGACGATCGTCGGGGGGGG (SEQ ID NO:6).

44. The composition of claim 1, wherein said unmethylated CpG-containing oligonucleotide consists of the nucleic acid sequence GGGGGGGGGGACGATCGTCGGGGGGGG (SEQ ID NO:7).

45. The composition of claim 1, wherein said virus-like particle is a virus-like particle of an RNA-phage.

46. The composition of claim 45, wherein said RNA-phage is bacteriophage Qβ.

47. The composition of claim 46, wherein said palindromic sequence is flanked at its 5'-terminus by at least 3 and at most 9 guanosine entities and wherein said palindromic sequence is flanked at its 3'-terminus by at least 6 and at most 9 guanosine entities.

48. The composition of claim 45, wherein said RNA-phage is bacteriophage AP205.

49. The composition of claim 48, wherein said palindromic sequence is flanked at its 5'-terminus by at least 3 and at most 9 guanosine entities and wherein said palindromic sequence is flanked at its 3'-terminus by at least 6 and at most 9 guanosine entities.

50. The composition of claim 1, wherein said virus-like particle comprises recombinant proteins, and wherein said recombinant proteins consist of coat proteins consisting of the amino acid sequence of SEQ ID NO: 10.

* * * * *

SEQUENCE LISTING

<160> NUMBER OF SEQ ID NOS: 111

<210> SEQ ID NO 1
<211> LENGTH: 10
<212> TYPE: DNA
<213> ORGANISM: Artificial sequence
<220> FEATURE:
<223> OTHER INFORMATION: oligonucleotide ISS

<400> SEQUENCE: 1
gacgatcgtc                                                          10

<210> SEQ ID NO 2
<211> LENGTH: 19
<212> TYPE: DNA
<213> ORGANISM: Artificial Sequence
<220> FEATURE:
<223> OTHER INFORMATION: oligonucleotide G3-6

<400> SEQUENCE: 2
ggggacgatc gtcggggggg                                               19

<210> SEQ ID NO 3
<211> LENGTH: 20
<212> TYPE: DNA
<213> ORGANISM: Artificial Sequence
<220> FEATURE:
<223> OTHER INFORMATION: oligonucleotide G4-6

<400> SEQUENCE: 3
gggggacgat cgtcggggggg                                              20

<210> SEQ ID NO 4
<211> LENGTH: 21
<212> TYPE: DNA
<213> ORGANISM: Artificial sequence
<220> FEATURE:
<223> OTHER INFORMATION: oligonucleotide G5-6

<400> SEQUENCE: 4 gggggggacga tcgtcggggg g                                            21

<210> SEQ ID NO 5
<211> LENGTH: 22
<212> TYPE: DNA
<213> ORGANISM: Artificial sequence
<220> FEATURE:
<223> OTHER INFORMATION: oligonucleotide G6-6

<400> SEQUENCE: 5 ggggggggacg atcgtcgggg gg                                           22

<210> SEQ ID NO 6
<211> LENGTH: 24
<212> TYPE: DNA
<213> ORGANISM: Artificial sequence
<220> FEATURE:
<223> OTHER INFORMATION: oligonucleotide G7-7

<400> SEQUENCE: 6 gggggggggac gatcgtcggg gggg                                         24

<210> SEQ ID NO 7
<211> LENGTH: 26

```
<212> TYPE: DNA
<213> ORGANISM: Artificial sequence
<220> FEATURE:
<223> OTHER INFORMATION: oligonucleotide G8-8

<400> SEQUENCE: 7 gggggggggga cgatcgtcgg gggggg                                           26

<210> SEQ ID NO 8
<211> LENGTH: 28
<212> TYPE: DNA
<213> ORGANISM: Artificial Sequence
<220> FEATURE:
<223> OTHER INFORMATION: oligonucleotide G9-9

<400> SEQUENCE: 8 ggggggggggg acgatcgtcg gggggggg                                         28

<210> SEQ ID NO 9
<211> LENGTH: 30
<212> TYPE: DNA
<213> ORGANISM: Artificial sequence
<220> FEATURE:
<223> OTHER INFORMATION: oligonucleotide G6

<400> SEQUENCE: 9 gggggggcgac gacgatcgtc gtcggggggg                                       30

<210> SEQ ID NO 10
<211> LENGTH: 132
<212> TYPE: PRT
<213> ORGANISM: Bacteriophage Q-beta

<400> SEQUENCE: 10

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 11
<211> LENGTH: 328
<212> TYPE: PRT
<213> ORGANISM: Bacteriophage Q-beta

<400> SEQUENCE: 11

Met Ala Lys Leu Glu Thr Val Thr Leu Gly Asn Ile Gly Lys Asp Gly
1               5                   10                  15
```

```
Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
            35                  40                  45

Val Thr Val Ser Val Ser Gln Pro Ser Arg Asn Arg Lys Asn Tyr Lys
            50                  55                  60

Val Gln Val Lys Ile Gln Asn Pro Thr Ala Cys Thr Ala Asn Gly Ser
 65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
                115                 120                 125

Leu Asn Pro Ala Tyr Trp Leu Leu Ile Ala Gly Gly Ser Gly Ser
                130                 135                 140

Lys Pro Asp Pro Val Ile Pro Asp Pro Ile Asp Pro Pro Gly
145                 150                 155                 160

Thr Gly Lys Tyr Thr Cys Pro Phe Ala Ile Trp Ser Leu Glu Glu Val
                165                 170                 175

Tyr Glu Pro Pro Thr Lys Asn Arg Pro Trp Pro Ile Tyr Asn Ala Val
                180                 185                 190

Glu Leu Gln Pro Arg Glu Phe Asp Val Ala Leu Lys Asp Leu Leu Gly
                195                 200                 205

Asn Thr Lys Trp Arg Asp Trp Asp Ser Arg Leu Ser Tyr Thr Thr Phe
                210                 215                 220

Arg Gly Cys Arg Gly Asn Gly Tyr Ile Asp Leu Asp Ala Thr Tyr Leu
225                 230                 235                 240

Ala Thr Asp Gln Ala Met Arg Asp Gln Lys Tyr Asp Ile Arg Glu Gly
                245                 250                 255

Lys Lys Pro Gly Ala Phe Gly Asn Ile Glu Arg Phe Ile Tyr Leu Lys
                260                 265                 270

Ser Ile Asn Ala Tyr Cys Ser Leu Ser Asp Ile Ala Ala Tyr His Ala
                275                 280                 285

Asp Gly Val Ile Val Gly Phe Trp Arg Asp Pro Ser Ser Gly Gly Ala
                290                 295                 300

Ile Pro Phe Asp Phe Thr Lys Phe Asp Lys Thr Lys Cys Pro Ile Gln
305                 310                 315                 320

Ala Val Ile Val Val Pro Arg Ala
                325

<210> SEQ ID NO 12
<211> LENGTH: 362
<212> TYPE: PRT
<213> ORGANISM: BK virus

<400> SEQUENCE: 12

Met Ala Pro Thr Lys Arg Lys Gly Glu Cys Pro Gly Ala Ala Pro Lys
 1               5                  10                  15

Lys Pro Lys Glu Pro Val Gln Val Pro Lys Leu Leu Ile Lys Gly Gly
                20                  25                  30

Val Glu Val Leu Glu Val Lys Thr Gly Val Asp Ala Ile Thr Glu Val
                35                  40                  45

Glu Cys Phe Leu Asn Pro Glu Met Gly Asp Pro Asp Asp Asn Leu Arg
                50                  55                  60
```

Gly Tyr Ser Gln His Leu Ser Ala Glu Asn Ala Phe Glu Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Lys Pro
    130                 135                 140

Val Gln Gly Ser Asn Phe His Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360

<210> SEQ ID NO 13
<211> LENGTH: 130
<212> TYPE: PRT
<213> ORGANISM: Bacteriophage fr

<400> SEQUENCE: 13

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Asn Asn Arg Lys Tyr Thr Val Lys Val Glu
        50                  55                  60

Val Pro Lys Val Ala Thr Gln Val Gln Gly Gly Val Glu Leu Pro Val

```
                65                  70                  75                  80
Ala Ala Trp Arg Ser Tyr Met Asn Met Glu Leu Thr Ile Pro Val Phe
                    85                  90                  95

Ala Thr Asn Asp Asp Cys Ala Leu Ile Val Lys Ala Leu Gln Gly Thr
                100                 105                 110

Phe Lys Thr Gly Asn Pro Ile Ala Thr Ala Ile Ala Ala Asn Ser Gly
        115                 120                 125

Ile Tyr
    130

<210> SEQ ID NO 14
<211> LENGTH: 130
<212> TYPE: PRT
<213> ORGANISM: Bacteriophage GA

<400> SEQUENCE: 14

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
                20                  25                  30

Leu Ser Asn Asn Ser Arg Ser Gln Ala Tyr Arg Val Thr Ala Ser Tyr
            35                  40                  45

Arg Ala Ser Gly Ala Asp Lys Arg Lys Tyr Ala Ile Lys Leu Glu Val
        50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                    85                  90                  95

Ala Thr Asp Asp Val Thr Val Ile Ser Lys Ser Leu Ala Gly Leu Phe
                100                 105                 110

Lys Val Gly Asn Pro Ile Ala Glu Ala Ile Ser Ser Gln Ser Gly Phe
            115                 120                 125

Tyr Ala
    130

<210> SEQ ID NO 15
<211> LENGTH: 594
<212> TYPE: DNA
<213> ORGANISM: Artificial Sequence
<220> FEATURE:
<223> OTHER INFORMATION: HBcAg containing p33 from LCMV
<220> FEATURE:
<221> NAME/KEY: CDS
<222> LOCATION: (1)..(591)

<400> SEQUENCE: 15 atg gac att gac cct tat aaa gaa ttt gga gct act gtg gag tta ctc         48
Met Asp Ile Asp Pro Tyr Lys Glu Phe Gly Ala Thr Val Glu Leu Leu
1               5                   10                  15 tcg

```
Leu Met Thr Leu Ala Thr Trp Val Gly Asn Asn Leu Glu Asp Pro Ala
 65                  70                  75                  80 tcc agg gat cta gta gtc aat tat gtt aat act aac atg ggt tta aag          288
Ser Arg Asp Leu Val Val Asn Tyr Val Asn Thr Asn Met Gly Leu Lys
                     85                  90                  95 atc agg caa cta ttg tgg ttt cat ata tct tgc ctt act ttt gga aga          336
Ile Arg Gln Leu Leu Trp Phe His Ile Ser Cys Leu Thr Phe Gly Arg
                    100                 105                 110 gag act gta ctt gaa tat ttg gtc tct ttc gga gtg tgg att cgc act          384
Glu Thr Val Leu Glu Tyr Leu Val Ser Phe Gly Val Trp Ile Arg Thr
                115                 120                 125 cct cca gcc tat aga cca cca aat gcc cct atc tta tca aca ctt ccg          432
Pro Pro Ala Tyr Arg Pro Pro Asn Ala Pro Ile Leu Ser Thr Leu Pro
            130                 135                 140 gaa act act gtt gtt aga cga cgg gac cga ggc agg tcc cct aga aga          480
Glu Thr Thr Val Val Arg Arg Arg Asp Arg Gly Arg Ser Pro Arg Arg
145                 150                 155                 160 aga act ccc tcg cct cgc aga cgc aga tct caa tcg ccg cgt cgc aga          528
Arg Thr Pro Ser Pro Arg Arg Arg Arg Ser Gln Ser Pro Arg Arg Arg
                165                 170                 175 aga tct caa tct cgg gaa tct caa tgt ctt ctc ctt aaa gct gtt tac          576
Arg Ser Gln Ser Arg Glu Ser Gln Cys Leu Leu Leu Lys Ala Val Tyr
            180                 185                 190 aac ttc gct acc atg taa                                                  594
Asn Phe Ala Thr Met
            195

<210> SEQ ID NO 16
<211> LENGTH: 197
<212> TYPE: PRT
<213> ORGANISM: Artificial Sequence
<220> FEATURE:
<223> OTHER INFORMATION: HBcAg containing p33 from LCMV

<400> SEQUENCE: 16

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys Leu Leu Leu Lys Ala Val Tyr
```

Asn Phe Ala Thr Met
        195

<210> SEQ ID NO 17
<211> LENGTH: 246
<212> TYPE: DNA
<213> ORGANISM: Artificial Sequence
<220> FEATURE:
<223> OTHER INFORMATION: dsDNA fragment for packaging and stabilization
      of BKV

<400> SEQUENCE: 17
ggcggtggtg tcagatctac aatgatcgtc atcaccttgg tgatgctgaa gaagaaacag      60
tacacatcca ttcatcatgg tgtggtggag gttgacgccg ctgtcacccc agaggagcgc     120
cacctgtcca agatgcagca gaacggctac gaaaatccaa cctacaagtt ctttgagcag     180
atgcagaacg ctagctatcc atacgatgtc cctgattacg cctaacgcga attcgccagc     240
acagtg                                                                246

<210> SEQ ID NO 18
<211> LENGTH: 5
<212> TYPE: PRT
<213> ORGANISM: Artificial Sequence
<220> FEATURE:
<223> OTHER INFORMATION: GGKGG Linker

<400> SEQUENCE: 18

Gly Gly Lys Gly Gly
1               5

<210> SEQ ID NO 19
<211> LENGTH: 128
<212> TYPE: PRT
<213> ORGANISM: Bacteriophage PP7

<400> SEQUENCE: 19

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

<210> SEQ ID NO 20
<211> LENGTH: 132
<212> TYPE: PRT
<213> ORGANISM: Bacteriophage Q-beta

<400> SEQUENCE: 20

```
Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 21
<211> LENGTH: 132
<212> TYPE: PRT
<213> ORGANISM: Bacteriophage Q-beta

<400> SEQUENCE: 21

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 22
<211> LENGTH: 132
<212> TYPE: PRT
<213> ORGANISM: Bacteriophage Q-beta

<400> SEQUENCE: 22

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45
```

```
Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65              70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
    130

<210> SEQ ID NO 23
<211> LENGTH: 132
<212> TYPE: PRT
<213> ORGANISM: Bacteriophage Q-beta

<400> SEQUENCE: 23

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65              70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
    130

<210> SEQ ID NO 24
<211> LENGTH: 132
<212> TYPE: PRT
<213> ORGANISM: Bacteriophage Q-beta

<400> SEQUENCE: 24

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65              70                  75                  80

Asp Pro Ser Val Thr Arg Gln Lys Tyr Ala Asp Val Thr Phe Ser Phe
                85                  90                  95
```

```
Thr Gln Tyr Ser Thr Asp Glu Glu Arg Ala Phe Val Arg Thr Glu Leu
                100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 25
<211> LENGTH: 184
<212> TYPE: PRT
<213> ORGANISM: Hepatitis B virus

<400> SEQUENCE: 25

Met Asp Ile Asp Pro Tyr Glu Phe Gly Ala Thr Val Glu Leu Leu Ser
1               5                   10                  15

Phe Leu Pro Ser Asp Phe Phe Pro Ser Val Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Thr Leu Ala Thr Trp Val Gly Asn Asn Leu Glu Asp Pro Ala Ser
65                  70                  75                  80

Arg Asp Leu Val Val Asn Tyr Val Asn Thr Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
        115                 120                 125

Pro Ala Tyr Arg Pro Pro Asn Ala Pro Ile Leu Ser Thr Leu Pro Glu
    130                 135                 140

Thr Thr Val Val Arg Arg Arg Asp Arg Gly Arg Ser Pro Arg Arg Arg
145                 150                 155                 160

Thr Pro Ser Pro Arg Arg Arg Arg Ser Gln Ser Pro Arg Arg Arg Arg
                165                 170                 175

Ser Gln Ser Arg Glu Ser Gln Cys
            180

<210> SEQ ID NO 26
<211> LENGTH: 213
<212> TYPE: PRT
<213> ORGANISM: Hepatitis B virus

<400> SEQUENCE: 26

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Asn
                85                  90                  95
```

```
Leu Ala Thr Trp Val Gly Gly Asn Leu Glu Asp Pro Val Ser Arg Asp
            100                 105                 110

Leu Val Val Gly Tyr Val Asn Thr Thr Val Gly Leu Lys Phe Arg Gln
            115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Pro Arg Arg Arg Arg Ser Gln Ser Pro Arg Arg Arg Arg Ser Gln Ser
            195                 200                 205

Arg Glu Ser Gln Cys
    210

<210> SEQ ID NO 27
<211> LENGTH: 188
<212> TYPE: PRT
<213> ORGANISM: Hepatitis B virus

<400> SEQUENCE: 27

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Pro Ser Thr Asn Cys
            180                 185

<210> SEQ ID NO 28
<211> LENGTH: 185
<212> TYPE: PRT
<213> ORGANISM: Hepatitis B virus

<400> SEQUENCE: 28

Met Asp Ile Asp Pro Tyr Lys Glu Phe Gly Ala Thr Val Glu Leu Leu
1               5                   10                  15
```

```
Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 29
<211> LENGTH: 152
<212> TYPE: PRT
<213> ORGANISM: Hepatitis B virus

<400> SEQUENCE: 29

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val
145                 150

<210> SEQ ID NO 30
<211> LENGTH: 3635
<212> TYPE: DNA
<213> ORGANISM: Artificial Sequence
<220> FEATURE:
<223> OTHER INFORMATION: plasmid pAP283-58
```

```
<400> SEQUENCE: 30
cgagctcgcc cctggcttat cgaaattaat acgactcact atagggagac cggaattcga      60
gctcgcccgg ggatcctcta gaattttctg cgcacccatc ccgggtggcg cccaaagtga     120
ggaaaatcac atggcaaata agccaatgca accgatcaca tctacagcaa ataaaattgt     180
gtggtcggat ccaactcgtt tatcaactac attttcagca agtctgttac gccaacgtgt     240
taaagttggt atagccgaac tgaataatgt ttcaggtcaa tatgtatctg tttataagcg     300
tcctgcacct aaaccggaag gttgtgcaga tgcctgtgtc attatgccga tgaaaaccca     360
atccattcgc acagtgattt cagggtcagc cgaaaacttg gctaccttaa agcagaatg     420
ggaaactcac aaacgtaacg ttgacacact cttcgcgagc ggcaacgccg gtttgggttt     480
ccttgaccct actgcggcta tcgtatcgtc tgatactact gcttaagctt gtattctata     540
gtgtcaccta aatcgtatgt gtatgataca aaggttatg tattaattgt agccgcgttc     600
taacgacaat atgtacaagc ctaattgtgt agcatctggc ttactgaagc agaccctatc     660
atctctctcg taaactgccg tcagagtcgg tttggttgga cgaaccttct gagtttctgg     720
taacgccgtt ccgcaccccg gaaatggtca ccgaaccaat cagcagggtc atcgctagcc     780
agatcctcta cgccggacgc atcgtggccg gcatcaccgg cgcacacagt gcggttgctg     840
gcgcctatat cgccgacatc accgatgggg aagatcgggc tcgccacttc gggctcatga     900
gcgcttgttt cggcgtgggt atggtggcag gccccgtggc cggggggactg ttgggcgcca     960
tctccttgca tgcaccattc cttgcggcgg cggtgcttca acggcctcaa cctactactg    1020
ggctgcttcc taatgcagga gtcgcataag ggagagcgtc gatatggtgc actctcagta    1080
caatctgctc tgatgccgca tagttaagcc aactccgcta tcgctacgtg actgggtcat    1140
ggctgcgccc cgacacccgc caacacccgc tgacgcgccc tgacgggctt gtctgctccc    1200
ggcatccgct tacagacaag ctgtgaccgt ctccgggagc tgcatgtgtc agaggttttc    1260
accgtcatca ccgaaacgcg cgaggcagct tgaagacgaa agggcctcgt gatacgccta    1320
ttttttatagg ttaatgtcat gataataatg gtttcttaga cgtcaggtgg cacttttcgg    1380
ggaaatgtgc gcggaacccc tatttgttta tttttctaaa tacattcaaa tatgtatccg    1440
ctcatgagac aataaccctg ataaatgctt caataatatt gaaaaaggaa gagtatgagt    1500
attcaacatt tccgtgtcgc ccttattccc ttttttgcgg cattttgcct tcctgttttt    1560
gctcacccag aaacgctggt gaaagtaaaa gatgctgaag atcagttggg tgcacgagtg    1620
ggttacatcg aactggatct caacagcggt aagatccttg agagttttcg ccccgaagaa    1680
cgttttccaa tgatgagcac ttttaaagtt ctgctatgtg gcgcggtatt atcccgtatt    1740
gacgccgggc aagagcaact cggtcgccgc atacactatt ctcagaatga cttggttgag    1800
tactcaccag tcacagaaaa gcatcttacg gatggcatga cagtaagaga attatgcagt    1860
gctgccataa ccatgagtga taacactgcg gccaacttac ttctgacaac gatcggagga    1920
ccgaaggagc taaccgcttt tttgcacaac atgggggatc atgtaactcg ccttgatcgt    1980
tgggaaccgg agctgaatga agccatacca aacgacgagc gtgacaccac gatgcctgta    2040
gcaatggcaa caacgttgcg caaactatta actggcgaac tacttactct agcttcccgg    2100
caacaattaa tagactggat ggaggcggat aaagttgcag gaccacttct gcgctcggcc    2160
cttccggctg gctggtttat tgctgataaa tctggagccg gtgagcgtgg gtctcgcggt    2220
atcattgcag cactggggcc agatggtaag ccctcccgta tcgtagttat ctacacgacg    2280
gggagtcagg caactatgga tgaacgaaat agacagatcg ctgagatagg tgcctcactg    2340
```

```
attaagcatt ggtaactgtc agaccaagtt tactcatata tactttagat tgatttaaaa    2400
cttcattttt aatttaaaag gatctaggtg aagatccttt ttgataatct catgaccaaa    2460 atccctttaac gtgagttttc gttccactga gcgtcagacc ccgtagaaaa gatcaaagga   2520
tcttcttgag atcctttttt tctgcgcgta atctgctgct tgcaaacaaa aaaaccaccg    2580
ctaccagcgg tggtttgttt gccggatcaa gagctaccaa ctcttttttcc gaaggtaact   2640 ggcttcagca gagcgcagat accaaatact gtccttctag tgtagccgta gttaggccac    2700
cacttcaaga actctgtagc accgcctaca tacctcgctc tgctaatcct gttaccagtg    2760
gctgctgcca gtggcgataa gtcgtgtctt accgggttgg actcaagacg atagttaccg    2820
gataaggcgc agcggtcggg ctgaacgggg ggttcgtgca cacagcccag cttggagcga    2880
acgacctaca ccgaactgag atacctacag cgcgagcatt gagaaagcgc cacgcttccc    2940
gaagggagaa aggcggacag gtatccggta agcggcaggg tcggaacagg agagcgcacg    3000
agggagcttc caggggggaaa cgcctggtat ctttatagtc ctgtcgggtt cgccacctc    3060 tgacttgagc gtcgatttttt gtgatgctcg tcagggggggc ggagcctatg gaaaaacgcc   3120
agcaacgcgg cctttttacg gttcctggcc ttttgctggc cttttgctca catgttcttt    3180
cctgcgttat cccctgattc tgtgataac cgtattaccg cctttgagtg agctgatacc    3240
gctcgccgca gccgaacgac gagcgcagcg agtcagtgag cgaggaagcg gaagagcgcc    3300
caatacgcaa accgcctctc cccgcgcgtt ggccgattca ttaatgcagc tgtggtgtca    3360
tggtcggtga tcgccagggt gccgacgcgc atctcgactg catggtgcac caatgcttct    3420
ggcgtcaggc agccatcgga agctgtggta tggccgtgca ggtcgtaaat cactgcataa    3480
ttcgtgtcgc tcaaggcgca ctcccgttct ggataatgtt ttttgcgccg acatcataac    3540
ggttctggca aatattctga aatgagctgt tgacaattaa tcatcgaact agttaactag    3600
tacgcaagtt cacgtaaaaa gggtatcgcg gaatt                              3635
```

<210> SEQ ID NO 31
<211> LENGTH: 131
<212> TYPE: PRT
<213> ORGANISM: Artificial Sequence
<220> FEATURE:
<223> OTHER INFORMATION: AP205 coat protein

<400> SEQUENCE: 31

```
Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125
```

Thr Thr Ala
    130

<210> SEQ ID NO 32
<211> LENGTH: 131
<212> TYPE: PRT
<213> ORGANISM: Artificial Sequence
<220> FEATURE:
<223> OTHER INFORMATION: AP205 coat protein

<400> SEQUENCE: 32

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 33
<211> LENGTH: 3607
<212> TYPE: DNA
<213> ORGANISM: Artificial Sequence
<220> FEATURE:
<223> OTHER INFORMATION: plasmid pAP281-32

<400> SEQUENCE: 33
cgagctcgcc cctggcttat cgaaattaat acgactcact atagggagac cggaattcga      60
gctcgcccgg ggatcctcta gattaaccca acgcgtagga gtcaggccat ggcaaataag     120
acaatgcaac cgatcacatc tacagcaaat aaaattgtgt ggtcggatcc aactcgttta     180
tcaactacat tttcagcaag tctgttacgc caacgtgtta agttggtat agccgaactg      240 aataatgttt caggtcaata tgtatctgtt tataagcgtc ctgcacctaa accgaaggtc     300
agatgcctgt gtcattatgc cgaatgaaaa ccaatccatt cgcacagtga tttcagggtc     360
agccgaaaac ttggctacct taaaagcaga atgggaaact cacaaacgta acgttgacac     420
actcttcgcg agcggcaacg ccggtttggg tttccttgac cctactgcgg ctatcgtatc     480
gtctgatact actgcttaag cttgtattct atagtgtcac ctaaatcgta tgtgtatgat     540
acataaggtt atgtattaat ggtagccgcg ttctaacgac aatatgtaca agcctaattg     600
tgtagcatct ggcttactga agcagaccct atcatctctc tcgtaaactg ccgtcagagt     660
cggttgggtt ggacagacct ctgagtttct ggtaacgccg ttccgcaccc cggaaatggt     720
caccgaacca ttcagcaggg tcatcgctag ccagatcctc tacgccggac gcatcgtggc     780
ccgcatcacc ggcgccacag gtgcggtgct ggcgcctata tcgccgacat caccgatggg     840
gaagatcggg ctcgccactt cgggctcatg atcgctggtt ccgcctgggg tatggtggca     900

```
ggccccgtgg cccggggac tgttgggcgc catctccttg catgcaccat tccttgcggc    960
ggcggtgctc aacggcctca acctactact gggctgcttc ctaatgcagg agtcgcataa   1020
gggagagcgt cgatatggtg cactctcagt acaatctgct ctgatgccgc atagttaagc   1080
caactccgct atcgctacgt gactgggtca tggctgcgcc ccgacacccg ccaacacccg   1140
ctgacgcgcc ctgacgggct tgtctgcttc cggcatccgc ttacagacaa gctgtgaccg   1200
tctccgggag ctgcatgtgt cagaggtttt caccgtcatc accgaaacgc gcgaggcagc   1260
ttgaagacga aagggcctcg tgatacgcct attttatag gttaatgtca tgataataat    1320
ggtttcttag acgtcaggtg cacttttcg gggaaatgtg cgcggacccc ctattggttt    1380
attttctaa atacattcaa atatgtatcc gctcatgaga caataaccct gataaatgct    1440
tcaataatat tgaaaagga agagtatgag tattcaacat ttccgtgtcg cccttattcc    1500
cttttttgcg cattttgcc ttcctgtttt tgctcaccca gaaacgctgg tgaaagtaaa    1560
agatgctgaa gatcagttgg gtgcacgagt gggttacatc gaactggatc tcaacagcgg   1620
taagatcctt gagagttttc gccccgaaga acgttttca atgatgagca cttttaaagt    1680
tctgctatgt gtcgcggtat tatcccgtat tgacgccggg caagagcaac tcggtcgccg   1740
catacactat tctcagaatg acttggtggt acctaccagt cacagaaaag catcttacgg   1800
atggcatgac agtaagagaa ttatgcagtg ctgccataac catgagtgat aacactgcgg   1860
ccaacttact tctgacaacg atcggaggac cgaaggagct aaccgctttt ttgcacaaca   1920
tgggggatca tgtaactcgc cttgatcgtt gggaaccgga gctgaatgaa gccataccaa   1980
acgacgagcg tgacaccacg atgcctgtac aacggcaac aacgttgcgc aaactattaa    2040
ctggcgaact acttactcta gcttcccggc aacaattaat agactggatg gaggcggata   2100
aagttgcagg accacttctg cgctcggccc ttccggctgg ctggtttatt gctgataaat   2160
ctggagccgt gagcgtgggt ctcgcggta tcattgcagc actggggcca gatggtaagc    2220
cctcccgtat cgtagttatc tacacgacgg ggagtcaggc aactatggat gaacgaaata   2280
gacagatcgc tgagataggt gcctcactga ttaagcattg gtaactgtca gaccaagttt   2340
actcatatat actttagatt gatttaaaac ttcattttta atttaaaagg atctaggtga   2400
agatcctttt tgataatctc atgaccaaaa tcccttaacg tgagttttcg ttccactgag   2460
cggtcagacc ccgtagaaag atcaaggat cttcttgaga tcctttttt ctgcgcgtaa     2520
tctgctgctt gcaaacaaaa aaaccaccgc taccagcggt ggtttgtttg ccggatcaag   2580
agctaccaac tctttttccg aaggtaactg gcttcagcag agcgcagata ccaaatactg   2640
tccttctagt gtagccgtag ttaggccacc acttcaagaa ctctgtagca ccgcctacat   2700
acctcgctct gctaatcctg ttaccagtgg ctgctgccag tggcgataag tcgtgtctta   2760
ccgggttgga ctcaagacga taggtaccgg ataaggcgca gcggtcgggc tgaacggggg   2820
gttcgtgcac acagcccagc ttggagcgaa cgacctacac cgaactgaga tacctacagc   2880
gcgagcattg agaaagcgcc acgcttcccg aagggagaaa ggcggacagg tatccggtaa   2940
gcggcagggt cggaacaaga gcgcacga gggagcttcc agggggaaac gcctggtatc     3000
tttatagtcc tgtcgggttt cgccacctct gacttgagcg tcgatttttg tgatgctcgt   3060
caggggggcg gagcctatgg aaaaacgcca gcaacgcggc cttttacgg ttcctggcct    3120
ttggctggcc ttttgctcac atgttctttc ctgcgttatc ccctgattct gtggataacc   3180
gtattaccgc ctttgagtga gctgataccg ctcgccgcag ccgaacgacc gacggcgcag   3240
```

-continued

```
cgagtcagtg agcgaggaag cggaagagcg cccaatacgc aaaccgcctc tccccgcgcg    3300
ttggccgatt cattaatgca gctgtggtgt catggtcggt gatcgccagg gtgccgacgc    3360
gcatctcgac tgcatggtgc accaatgctt ctggcgtcag gcagccatcg gaagctgtgg    3420
tatggccgtg caggtcgtaa atcactgcat aattcgtgtc gctcaaggcg cactcccgtt    3480
ctggataatg ttttttgcgg cgacatcata acggttctgg caaatattct gaaatgagct    3540
ggtgacaatt aatcatcgaa ctagttaact agtacgcaag ttcacgtaaa aagggtatcg    3600
cggaatt                                                              3607
```

<210> SEQ ID NO 34
<211> LENGTH: 21
<212> TYPE: DNA
<213> ORGANISM: Artificial sequence
<220> FEATURE:
<223> OTHER INFORMATION: CyCpG

<400> SEQUENCE: 34

```
tccatgacgt tcctgaataa t                                                21
```

<210> SEQ ID NO 35
<211> LENGTH: 10
<212> TYPE: PRT
<213> ORGANISM: Artificial sequence
<220> FEATURE:
<223> OTHER INFORMATION: Melan A 26-35 A/L

<400> SEQUENCE: 35

```
Glu Leu Ala Gly Ile Gly Ile Leu Thr Val
1               5                   10
```

<210> SEQ ID NO 36
<211> LENGTH: 20
<212> TYPE: PRT
<213> ORGANISM: Artificial sequence
<220> FEATURE:
<223> OTHER INFORMATION: Melan A 16-35 A/L

<400> SEQUENCE: 36

```
Gly His Gly His Ser Tyr Thr Thr Ala Glu Glu Leu Ala Gly Ile Gly
1               5                   10                  15

Ile Leu Thr Val
            20
```

<210> SEQ ID NO 37
<211> LENGTH: 21
<212> TYPE: PRT
<213> ORGANISM: Artificial sequence
<220> FEATURE:
<223> OTHER INFORMATION: MelanA 20-40 A/L

<400> SEQUENCE: 37

```
Ser Tyr Thr Thr Ala Glu Glu Leu Ala Gly Ile Gly Ile Leu Thr Val
1               5                   10                  15

Ile Leu Gly Val Leu
            20
```

<210> SEQ ID NO 38
<211> LENGTH: 14
<212> TYPE: PRT
<213> ORGANISM: Artificial Sequence
<220> FEATURE:
<223> OTHER INFORMATION: MelanA 26-40 A/L

```
<400> SEQUENCE: 38

Glu Leu Ala Gly Ile Gly Ile Leu Thr Val Ile Leu Gly Val
1               5                   10

<210> SEQ ID NO 39
<211> LENGTH: 21
<212> TYPE: PRT
<213> ORGANISM: Artificial Sequence
<220> FEATURE:
<223> OTHER INFORMATION: MelanA 16-35

<400> SEQUENCE: 39

Cys Gly His Gly His Ser Tyr Thr Thr Ala Glu Glu Ala Ala Gly Ile
1               5                   10                  15

Gly Ile Leu Thr Val
            20

<210> SEQ ID NO 40
<211> LENGTH: 21
<212> TYPE: PRT
<213> ORGANISM: Artificial sequence
<220> FEATURE:
<223> OTHER INFORMATION: MelanA 16-35 A/L

<400> SEQUENCE: 40

Cys Gly His Gly His Ser Tyr Thr Thr Ala Glu Glu Leu Ala Gly Ile
1               5                   10                  15

Gly Ile Leu Thr Val
            20

<210> SEQ ID NO 41
<211> LENGTH: 13
<212> TYPE: PRT
<213> ORGANISM: Artificial Sequence
<220> FEATURE:
<223> OTHER INFORMATION: MelanA 26-35

<400> SEQUENCE: 41

Cys Gly Gly Glu Ala Ala Gly Ile Gly Ile Leu Thr Val
1               5                   10

<210> SEQ ID NO 42
<211> LENGTH: 13
<212> TYPE: PRT
<213> ORGANISM: Artificial Sequence
<220> FEATURE:
<223> OTHER INFORMATION: MelanA 26-35 A/L

<400> SEQUENCE: 42

Cys Gly Gly Glu Leu Ala Gly Ile Gly Ile Leu Thr Val
1               5                   10

<210> SEQ ID NO 43
<211> LENGTH: 22
<212> TYPE: PRT
<213> ORGANISM: Artificial sequence
<220> FEATURE:
<223> OTHER INFORMATION: MelanA 20-40 A/L

<400> SEQUENCE: 43

Cys Ser Tyr Thr Thr Ala Glu Glu Leu Ala Gly Ile Gly Ile Leu Thr
1               5                   10                  15

Val Ile Leu Gly Val Leu
            20
```

```
<210> SEQ ID NO 44
<211> LENGTH: 18
<212> TYPE: PRT
<213> ORGANISM: Artificial sequence
<220> FEATURE:
<223> OTHER INFORMATION: MelanA 26-40 A/L

<400> SEQUENCE: 44

Cys Gly Gly Glu Leu Ala Gly Ile Gly Ile Leu Thr Val Ile Leu Gly
1               5                   10                  15

Val Leu

<210> SEQ ID NO 45
<211> LENGTH: 13
<212> TYPE: PRT
<213> ORGANISM: Artificial sequence
<220> FEATURE:
<223> OTHER INFORMATION: MelanA 26-35-C

<400> SEQUENCE: 45

Glu Leu Ala Gly Ile Gly Ile Leu Thr Val Gly Gly Cys
1               5                   10

<210> SEQ ID NO 46
<211> LENGTH: 35
<212> TYPE: DNA
<213> ORGANISM: Artificial Sequence
<220> FEATURE:
<223> OTHER INFORMATION: sequence of vector pAb185

<400> SEQUENCE: 46
tctagattaa cccaacgcgt aggagtcagg ccatg                              35

<210> SEQ ID NO 47
<211> LENGTH: 9
<212> TYPE: PRT
<213> ORGANISM: Artificial Sequence
<220> FEATURE:
<223> OTHER INFORMATION: N terminal glycine serine linkers
<220> FEATURE:
<221> NAME/KEY: REPEAT
<222> LOCATION: (1)..(1)
<223> OTHER INFORMATION: Glycine can be repeated from zero to five times
<220> FEATURE:
<221> NAME/KEY: REPEAT
<222> LOCATION: (3)..(3)
<223> OTHER INFORMATION: Glycine can be repeated from zero to ten times
<220> FEATURE:
<221> NAME/KEY: REPEAT
<222> LOCATION: (4)..(4)
<223> OTHER INFORMATION: Serine can be repeated from zero to two times
<220> FEATURE:
<221> NAME/KEY: REPEAT
<222> LOCATION: (5)..(9)
<223> OTHER INFORMATION: These residues can be repeated from zero to
      three times as a group

<400> SEQUENCE: 47

Gly Cys Gly Ser Gly Gly Gly Gly Ser
1               5

<210> SEQ ID NO 48
<211> LENGTH: 10
<212> TYPE: PRT
<213> ORGANISM: Artificial Sequence
<220> FEATURE:
<223> OTHER INFORMATION: C terminal glycine serine linkers
<220> FEATURE:
<221> NAME/KEY: REPEAT
```

```
<222> LOCATION: (1)..(1)
<223> OTHER INFORMATION: Glycine can be repeated from zero to ten times
<220> FEATURE:
<221> NAME/KEY: REPEAT
<222> LOCATION: (2)..(2)
<223> OTHER INFORMATION: Serine can be repeated from zero to two times
<220> FEATURE:
<221> NAME/KEY: REPEAT
<222> LOCATION: (3)..(7)
<223> OTHER INFORMATION: These residues can be repeated from zero to
      three times as a group
<220> FEATURE:
<221> NAME/KEY: REPEAT
<222> LOCATION: (8)..(8)
<223> OTHER INFORMATION: Glycine can be repeated from zero to eight
      times
<220> FEATURE:
<221> NAME/KEY: REPEAT
<222> LOCATION: (10)..(10)
<223> OTHER INFORMATION: Glycine can be repeated from zero to five times

<400> SEQUENCE: 48

Gly Ser Gly Gly Gly Gly Ser Gly Cys Gly
1               5                   10

<210> SEQ ID NO 49
<211> LENGTH: 5
<212> TYPE: PRT
<213> ORGANISM: Artificial Sequence
<220> FEATURE:
<223> OTHER INFORMATION: Glycine serine linker

<400> SEQUENCE: 49

Gly Gly Gly Gly Ser
1               5

<210> SEQ ID NO 50
<211> LENGTH: 10
<212> TYPE: PRT
<213> ORGANISM: Artificial Sequence
<220> FEATURE:
<223> OTHER INFORMATION: N-terminal gamma1

<400> SEQUENCE: 50

Cys Gly Asp Lys Thr His Thr Ser Pro Pro
1               5                   10

<210> SEQ ID NO 51
<211> LENGTH: 10
<212> TYPE: PRT
<213> ORGANISM: Artificial Sequence
<220> FEATURE:
<223> OTHER INFORMATION: C-terminal gamma 1

<400> SEQUENCE: 51

Asp Lys Thr His Thr Ser Pro Pro Cys Gly
1               5                   10

<210> SEQ ID NO 52
<211> LENGTH: 17
<212> TYPE: PRT
<213> ORGANISM: Artificial Sequence
<220> FEATURE:
<223> OTHER INFORMATION: N-terminal gamma 3

<400> SEQUENCE: 52

Cys Gly Gly Pro Lys Pro Ser Thr Pro Pro Gly Ser Ser Gly Gly Ala
1               5                   10                  15

Pro
```

```
<210> SEQ ID NO 53
<211> LENGTH: 18
<212> TYPE: PRT
<213> ORGANISM: Artificial Sequence
<220> FEATURE:
<223> OTHER INFORMATION: C-terminal gamma 3

<400> SEQUENCE: 53

Pro Lys Pro Ser Thr Pro Pro Gly Ser Ser Gly Gly Ala Pro Gly Gly
1               5                   10                  15

Cys Gly

<210> SEQ ID NO 54
<211> LENGTH: 6
<212> TYPE: PRT
<213> ORGANISM: Artificial Sequence
<220> FEATURE:
<223> OTHER INFORMATION: N-terminal glycine linker

<400> SEQUENCE: 54

Gly Cys Gly Gly Gly Gly
1               5

<210> SEQ ID NO 55
<211> LENGTH: 6
<212> TYPE: PRT
<213> ORGANISM: Artificial Sequence
<220> FEATURE:
<223> OTHER INFORMATION: C-terminal glycine linker

<400> SEQUENCE: 55

Gly Gly Gly Gly Cys Gly
1               5

<210> SEQ ID NO 56
<211> LENGTH: 6
<212> TYPE: PRT
<213> ORGANISM: Artificial Sequence
<220> FEATURE:
<223> OTHER INFORMATION: C-terminal glycine-lysine linker

<400> SEQUENCE: 56

Gly Gly Lys Lys Gly Cys
1               5

<210> SEQ ID NO 57
<211> LENGTH: 6
<212> TYPE: PRT
<213> ORGANISM: Artificial Sequence
<220> FEATURE:
<223> OTHER INFORMATION: N-terminal glycine-lysine linker

<400> SEQUENCE: 57

Cys Gly Lys Lys Gly Gly
1               5

<210> SEQ ID NO 58
<211> LENGTH: 6
<212> TYPE: PRT
<213> ORGANISM: Artificial Sequence
<220> FEATURE:
<223> OTHER INFORMATION: N-terminal linker 1

<400> SEQUENCE: 58

Cys Gly Lys Lys Gly Gly
```

```
<210> SEQ ID NO 59
<211> LENGTH: 6
<212> TYPE: PRT
<213> ORGANISM: Artificial Sequence
<220> FEATURE:
<223> OTHER INFORMATION: N-terminal linker 2

<400> SEQUENCE: 59

Cys Gly Asp Glu Gly Gly
1               5

<210> SEQ ID NO 60
<211> LENGTH: 6
<212> TYPE: PRT
<213> ORGANISM: Artificial Sequence
<220> FEATURE:
<223> OTHER INFORMATION: C-terminal liker

<400> SEQUENCE: 60

Gly Gly Lys Lys Gly Cys
1               5

<210> SEQ ID NO 61
<211> LENGTH: 6
<212> TYPE: PRT
<213> ORGANISM: Artificial Sequence
<220> FEATURE:
<223> OTHER INFORMATION: C-terminal linker 2

<400> SEQUENCE: 61

Gly Gly Glu Asp Gly Cys
1               5

<210> SEQ ID NO 62
<211> LENGTH: 4
<212> TYPE: PRT
<213> ORGANISM: Artificial Sequence
<220> FEATURE:
<223> OTHER INFORMATION: C-terminal linker 3

<400> SEQUENCE: 62

Gly Gly Cys Gly
1

<210> SEQ ID NO 63
<211> LENGTH: 9
<212> TYPE: PRT
<213> ORGANISM: Homo sapiens

<400> SEQUENCE: 63

Lys Thr Trp Gly Gln Tyr Trp Gln Val
1               5

<210> SEQ ID NO 64
<211> LENGTH: 9
<212> TYPE: PRT
<213> ORGANISM: Homo sapiens

<400> SEQUENCE: 64

Ile Thr Asp Gln Val Pro Phe Ser Val
1               5

<210> SEQ ID NO 65
<211> LENGTH: 9
```

```
<212> TYPE: PRT
<213> ORGANISM: Homo Sapiens

<400> SEQUENCE: 65

Tyr Leu Glu Pro Gly Pro Val Thr Ala
1               5

<210> SEQ ID NO 66
<211> LENGTH: 10
<212> TYPE: PRT
<213> ORGANISM: Homo sapiens

<400> SEQUENCE: 66

Leu Leu Asp Gly Thr Ala Thr Leu Arg Leu
1               5                   10

<210> SEQ ID NO 67
<211> LENGTH: 10
<212> TYPE: PRT
<213> ORGANISM: Homo sapiens

<400> SEQUENCE: 67

Val Leu Tyr Arg Tyr Gly Ser Phe Ser Val
1               5                   10

<210> SEQ ID NO 68
<211> LENGTH: 10
<212> TYPE: PRT
<213> ORGANISM: Homo sapiens

<400> SEQUENCE: 68

Glu Ala Ala Gly Ile Gly Ile Leu Thr Val
1               5                   10

<210> SEQ ID NO 69
<211> LENGTH: 9
<212> TYPE: PRT
<213> ORGANISM: Homo sapiens

<400> SEQUENCE: 69

Ala Ala Gly Ile Gly Ile Leu Thr Val
1               5

<210> SEQ ID NO 70
<211> LENGTH: 9
<212> TYPE: PRT
<213> ORGANISM: Homo sapiens

<400> SEQUENCE: 70

Ile Leu Thr Val Ile Leu Gly Val Leu
1               5

<210> SEQ ID NO 71
<211> LENGTH: 9
<212> TYPE: PRT
<213> ORGANISM: Homo sapiens

<400> SEQUENCE: 71

Met Leu Leu Ala Val Leu Tyr Cys Leu
1               5

<210> SEQ ID NO 72
<211> LENGTH: 9
<212> TYPE: PRT
<213> ORGANISM: Homo sapiens
```

```
<400> SEQUENCE: 72

Tyr Met Asp Gly Thr Met Ser Gln Val
1               5

<210> SEQ ID NO 73
<211> LENGTH: 9
<212> TYPE: PRT
<213> ORGANISM: Homo sapiens

<400> SEQUENCE: 73

Val Leu Pro Asp Val Phe Ile Arg Cys
1               5

<210> SEQ ID NO 74
<211> LENGTH: 9
<212> TYPE: PRT
<213> ORGANISM: Homo sapiens

<400> SEQUENCE: 74

Phe Leu Trp Gly Pro Arg Ala Leu Val
1               5

<210> SEQ ID NO 75
<211> LENGTH: 9
<212> TYPE: PRT
<213> ORGANISM: Homo sapiens

<400> SEQUENCE: 75

Tyr Leu Ser Gly Ala Asn Leu Asn Leu
1               5

<210> SEQ ID NO 76
<211> LENGTH: 8
<212> TYPE: PRT
<213> ORGANISM: Homo sapiens

<400> SEQUENCE: 76

Arg Met Pro Glu Ala Ala Pro Pro
1               5

<210> SEQ ID NO 77
<211> LENGTH: 9
<212> TYPE: PRT
<213> ORGANISM: Homo sapiens

<400> SEQUENCE: 77

Ser Thr Pro Pro Pro Gly Thr Arg Val
1               5

<210> SEQ ID NO 78
<211> LENGTH: 9
<212> TYPE: PRT
<213> ORGANISM: Homo sapiens

<400> SEQUENCE: 78

Leu Leu Gly Arg Asn Ser Phe Glu Val
1               5

<210> SEQ ID NO 79
<211> LENGTH: 9
<212> TYPE: PRT
<213> ORGANISM: Homo sapiens

<400> SEQUENCE: 79
```

Lys Ile Phe Gly Ser Leu Ala Phe Leu
1               5

<210> SEQ ID NO 80
<211> LENGTH: 9
<212> TYPE: PRT
<213> ORGANISM: Homo sapiens

<400> SEQUENCE: 80

Ile Ile Ser Ala Val Val Gly Ile Leu
1               5

<210> SEQ ID NO 81
<211> LENGTH: 8
<212> TYPE: PRT
<213> ORGANISM: Homo sapiens

<400> SEQUENCE: 81

Thr Leu Gly Ile Val Cys Pro Ile
1               5

<210> SEQ ID NO 82
<211> LENGTH: 9
<212> TYPE: PRT
<213> ORGANISM: Homo sapiens

<400> SEQUENCE: 82

Lys Ala Val Tyr Asn Phe Ala Thr Met
1               5

<210> SEQ ID NO 83
<211> LENGTH: 12
<212> TYPE: PRT
<213> ORGANISM: Homo sapiens

<400> SEQUENCE: 83

Cys Gly Gly Lys Ala Val Tyr Asn Phe Ala Thr Met
1               5                   10

<210> SEQ ID NO 84
<211> LENGTH: 12
<212> TYPE: PRT
<213> ORGANISM: Homo sapiens

<400> SEQUENCE: 84

Lys Ala Val Tyr Asn Phe Ala Thr Met Gly Gly Cys
1               5                   10

<210> SEQ ID NO 85
<211> LENGTH: 18
<212> TYPE: PRT
<213> ORGANISM: Homo sapiens

<400> SEQUENCE: 85

Cys Gly Gly Gly Ser Glu Glu Ile Arg Ser Leu Tyr Asn Thr Val Ala
1               5                   10                  15

Thr Leu

<210> SEQ ID NO 86
<211> LENGTH: 50
<212> TYPE: PRT
<213> ORGANISM: Artificial Sequence
<220> FEATURE:
<223> OTHER INFORMATION: HIV Gag-G50

```
<400> SEQUENCE: 86

Cys Gln Gly Gln Met Val His Gln Ala Ile Ser Pro Arg Thr Leu Asn
1               5                   10                  15

Ala Trp Val Lys Ala Phe Ser Pro Glu Val Ile Pro Met Phe Ser Ala
                20                  25                  30

Leu Ser Glu Gly Ala Thr Pro Gln Asp Leu Asn Thr Met Leu Asn Thr
        35                  40                  45

Val Lys
    50

<210> SEQ ID NO 87
<211> LENGTH: 56
<212> TYPE: PRT
<213> ORGANISM: Artificial Sequence
<220> FEATURE:
<223> OTHER INFORMATION: HIV Nef-N56

<400> SEQUENCE: 87

Cys Gly Val Gly Phe Pro Val Arg Pro Gln Val Pro Leu Arg Pro Met
1               5                   10                  15

Thr Tyr Lys Ala Ala Val Asp Leu Ser His Phe Leu Lys Glu Lys Gly
                20                  25                  30

Gly Leu Glu Gly Pro Gly Ile Arg Tyr Pro Leu Thr Phe Gly Trp Cys
        35                  40                  45

Phe Lys Leu Val Pro Val Glu Pro
    50                  55

<210> SEQ ID NO 88
<211> LENGTH: 69
<212> TYPE: PRT
<213> ORGANISM: Artificial Sequence
<220> FEATURE:
<223> OTHER INFORMATION: Gag-G68n

<400> SEQUENCE: 88

Cys Gly Glu Ile Tyr Lys Arg Trp Ile Ile Leu Gly Leu Asn Lys Ile
1               5                   10                  15

Val Arg Met Tyr Gln Gly Gln Met Val His Gln Ala Ile Ser Pro Arg
                20                  25                  30

Thr Leu Asn Ala Trp Val Lys Ala Phe Ser Pro Glu Val Ile Pro Met
        35                  40                  45

Phe Ser Ala Leu Ser Glu Gly Ala Thr Pro Gln Asp Leu Asn Thr Met
    50                  55                  60

Leu Asn Thr Val Lys
65

<210> SEQ ID NO 89
<211> LENGTH: 9
<212> TYPE: PRT
<213> ORGANISM: Homo sapiens

<400> SEQUENCE: 89

Leu Ala Gly Ile Gly Ile Leu Thr Val
1               5

<210> SEQ ID NO 90
<211> LENGTH: 9
<212> TYPE: PRT
<213> ORGANISM: Homo sapiens
```

```
<400> SEQUENCE: 90

Met Ala Gly Ile Gly Ile Leu Thr Val
1               5

<210> SEQ ID NO 91
<211> LENGTH: 10
<212> TYPE: PRT
<213> ORGANISM: Homo sapiens

<400> SEQUENCE: 91

Glu Ala Met Gly Ile Gly Ile Leu Thr Val
1               5                   10

<210> SEQ ID NO 92
<211> LENGTH: 10
<212> TYPE: PRT
<213> ORGANISM: Homo sapiens

<400> SEQUENCE: 92

Glu Met Ala Gly Ile Gly Ile Leu Thr Val
1               5                   10

<210> SEQ ID NO 93
<211> LENGTH: 10
<212> TYPE: PRT
<213> ORGANISM: Homo sapiens

<400> SEQUENCE: 93

Tyr Ala Ala Gly Ile Gly Ile Leu Thr Val
1               5                   10

<210> SEQ ID NO 94
<211> LENGTH: 10
<212> TYPE: PRT
<213> ORGANISM: Homo sapiens

<400> SEQUENCE: 94

Phe Ala Ala Gly Ile Gly Ile Leu Thr Val
1               5                   10

<210> SEQ ID NO 95
<211> LENGTH: 9
<212> TYPE: PRT
<213> ORGANISM: Homo sapiens

<400> SEQUENCE: 95

Leu Pro Tyr Leu Gly Trp Leu Val Phe
1               5

<210> SEQ ID NO 96
<211> LENGTH: 206
<212> TYPE: PRT
<213> ORGANISM: Human immunodeficiency virus

<400> SEQUENCE: 96

Met Gly Gly Lys Trp Ser Lys Ser Val Val Gly Trp Pro Thr Val
1               5                   10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Asn Asn Ala Asp Cys Ala Trp Leu Glu Ala Gln Glu Glu Glu
        50                  55                  60
```

```
Glu Val Gly Phe Pro Val Arg Pro Gln Val Pro Leu Arg Pro Met Thr
 65                  70                  75                  80

Tyr Lys Ala Ala Val Asp Leu Ser His Phe Leu Lys Glu Lys Gly Gly
                 85                  90                  95

Leu Glu Gly Leu Ile Tyr Ser Gln Lys Arg Gln Asp Ile Leu Asp Leu
            100                 105                 110

Trp Val Tyr His Thr Gln Gly Tyr Phe Pro Asp Trp Gln Asn Tyr Thr
            115                 120                 125

Pro Gly Pro Gly Ile Arg Tyr Pro Leu Thr Phe Gly Trp Cys Phe Lys
            130                 135                 140

Leu Val Pro Val Glu Pro Glu Lys Val Glu Glu Ala Asn Glu Gly Glu
145                 150                 155                 160

Asn Asn Ser Leu Leu His Pro Met Ser Leu His Gly Met Asp Asp Pro
                165                 170                 175

Glu Arg Glu Val Leu Val Trp Lys Phe Asp Ser Arg Leu Ala Phe His
            180                 185                 190

His Met Ala Arg Glu Leu His Pro Glu Tyr Tyr Lys Asp Cys
            195                 200                 205

<210> SEQ ID NO 97
<211> LENGTH: 500
<212> TYPE: PRT
<213> ORGANISM: Human immunodeficiency virus

<400> SEQUENCE: 97

Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
 65                 70                  75                  80

Thr Val Ala Thr Leu Tyr Cys Val His Gln Lys Ile Glu Val Lys Asp
                 85                 90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Ser Ser Gln Val
            115                 120                 125

Ser Gln Asn Tyr Pro Ile Val Gln Asn Leu Gln Gly Gln Met Val His
            130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Leu His Pro Val His Ala Gly Pro Ile Ala
        210                 215                 220

Pro Gly Gln Met Arg Glu Pro Arg Gly Ser Asp Ile Ala Gly Thr Thr
```

```
            225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
        290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Asn Asp
                485                 490                 495

Pro Ser Ser Gln
            500

<210> SEQ ID NO 98
<211> LENGTH: 34
<212> TYPE: PRT
<213> ORGANISM: Human immunodeficiency virus

<400> SEQUENCE: 98

Val Gly Phe Pro Val Arg Pro Gln Val Pro Leu Arg Pro Met Thr Tyr
1               5                   10                  15

Lys Ala Ala Val Asp Leu Ser His Phe Leu Lys Glu Lys Gly Gly Leu
                20                  25                  30

Glu Gly

<210> SEQ ID NO 99
<211> LENGTH: 20
<212> TYPE: PRT
<213> ORGANISM: Human immunodeficiency virus

<400> SEQUENCE: 99

Pro Gly Ile Arg Tyr Pro Leu Thr Phe Gly Trp Cys Phe Lys Leu Val
1               5                   10                  15
```

-continued

```
Pro Val Glu Pro
         20

<210> SEQ ID NO 100
<211> LENGTH: 5
<212> TYPE: PRT
<213> ORGANISM: Human immunodeficiency virus

<400> SEQUENCE: 100

Lys Val Val Glu Glu
1               5

<210> SEQ ID NO 101
<211> LENGTH: 18
<212> TYPE: PRT
<213> ORGANISM: Human immunodeficiency virus

<400> SEQUENCE: 101

Gln Gly Gln Met Val His Gln Ala Ile Ser Pro Arg Thr Leu Asn Ala
1               5                   10                  15

Trp Val

<210> SEQ ID NO 102
<211> LENGTH: 30
<212> TYPE: PRT
<213> ORGANISM: Human immunodeficiency virus

<400> SEQUENCE: 102

Lys Ala Phe Ser Pro Glu Val Ile Pro Met Phe Ser Ala Leu Ser Glu
1               5                   10                  15

Gly Ala Thr Pro Gln Asp Leu Asn Thr Met Leu Asn Thr Val
            20                  25                  30

<210> SEQ ID NO 103
<211> LENGTH: 19
<212> TYPE: PRT
<213> ORGANISM: Human immunodeficiency virus

<400> SEQUENCE: 103

Gly Glu Ile Tyr Lys Arg Trp Ile Ile Leu Gly Leu Asn Lys Ile Val
1               5                   10                  15

Arg Met Tyr

<210> SEQ ID NO 104
<211> LENGTH: 54
<212> TYPE: PRT
<213> ORGANISM: Human immunodeficiency virus

<400> SEQUENCE: 104

Val Gly Phe Pro Val Arg Pro Gln Val Pro Leu Arg Pro Met Thr Tyr
1               5                   10                  15

Lys Ala Ala Val Asp Leu Ser His Phe Leu Lys Glu Lys Gly Gly Leu
            20                  25                  30

Glu Gly Pro Gly Ile Arg Tyr Pro Leu Thr Phe Gly Trp Cys Phe Lys
        35                  40                  45

Leu Val Pro Val Glu Pro
        50

<210> SEQ ID NO 105
<211> LENGTH: 48
<212> TYPE: PRT
```

<213> ORGANISM: Human immunodeficiency virus

<400> SEQUENCE: 105

Gln Gly Gln Met Val His Gln Ala Ile Ser Pro Arg Thr Leu Asn Ala
1               5                   10                  15

Trp Val Lys Ala Phe Ser Pro Glu Val Ile Pro Met Phe Ser Ala Leu
            20                  25                  30

Ser Glu Gly Ala Thr Pro Gln Asp Leu Asn Thr Met Leu Asn Thr Val
        35                  40                  45

<210> SEQ ID NO 106
<211> LENGTH: 49
<212> TYPE: PRT
<213> ORGANISM: Artificial Sequence
<220> FEATURE:
<223> OTHER INFORMATION: HIV C_Gag-G50

<400> SEQUENCE: 106

Cys Gln Gly Gln Met Val His Gln Ala Ile Ser Pro Arg Thr Leu Asn
1               5                   10                  15

Ala Trp Val Lys Ala Phe Ser Pro Glu Val Ile Pro Met Phe Ser Ala
            20                  25                  30

Leu Ser Glu Gly Ala Thr Pro Gln Asp Leu Asn Thr Met Leu Asn Thr
        35                  40                  45

Val

<210> SEQ ID NO 107
<211> LENGTH: 67
<212> TYPE: PRT
<213> ORGANISM: Human immunodeficiency virus

<400> SEQUENCE: 107

Gly Glu Ile Tyr Lys Arg Trp Ile Ile Leu Gly Leu Asn Lys Ile Val
1               5                   10                  15

Arg Met Tyr Gln Gly Gln Met Val His Gln Ala Ile Ser Pro Arg Thr
            20                  25                  30

Leu Asn Ala Trp Val Lys Ala Phe Ser Pro Glu Val Ile Pro Met Phe
        35                  40                  45

Ser Ala Leu Ser Glu Gly Ala Thr Pro Gln Asp Leu Asn Thr Met Leu
    50                  55                  60

Asn Thr Val
65

<210> SEQ ID NO 108
<211> LENGTH: 68
<212> TYPE: PRT
<213> ORGANISM: Artificial Sequence
<220> FEATURE:
<223> OTHER INFORMATION: HIV C_Gag-G68n

<400> SEQUENCE: 108

Cys Gly Glu Ile Tyr Lys Arg Trp Ile Ile Leu Gly Leu Asn Lys Ile
1               5                   10                  15

Val Arg Met Tyr Gln Gly Gln Met Val His Gln Ala Ile Ser Pro Arg
            20                  25                  30

Thr Leu Asn Ala Trp Val Lys Ala Phe Ser Pro Glu Val Ile Pro Met
        35                  40                  45

Phe Ser Ala Leu Ser Glu Gly Ala Thr Pro Gln Asp Leu Asn Thr Met
    50                  55                  60

```
Leu Asn Thr Val
65

<210> SEQ ID NO 109
<211> LENGTH: 118
<212> TYPE: PRT
<213> ORGANISM: homo sapiens

<400> SEQUENCE: 109

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 110
<211> LENGTH: 16
<212> TYPE: PRT
<213> ORGANISM: Artificial Sequence
<220> FEATURE:
<223> OTHER INFORMATION: CSPKSL-MelanA 26-35 A/L

<400> SEQUENCE: 110

Cys Ser Pro Lys Ser Leu Glu Leu Ala Gly Ile Gly Ile Leu Thr Val
1               5                   10                  15

<210> SEQ ID NO 111
<211> LENGTH: 18
<212> TYPE: PRT
<213> ORGANISM: Artificial Sequence
<220> FEATURE:
<223> OTHER INFORMATION: MelanA 26-40-C A/L

<400> SEQUENCE: 111

Glu Leu Ala Gly Ile Gly Ile Leu Thr Val Ile Leu Gly Val Leu Gly
1               5                   10                  15

Gly Cys
```